(12) United States Patent
Gaufreteau et al.

(10) Patent No.: US 10,519,140 B2
(45) Date of Patent: Dec. 31, 2019

(54) INDOLIN-2-ONE DERIVATIVES

(71) Applicant: Hoffmann-La Roche Inc., Little Falls, NJ (US)

(72) Inventors: Delphine Gaufreteau, Basel (CH); Sabine Kolczewski, Basel (CH); Jean-Marc Plancher, Basel (CH); Theodor Stoll, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/971,368

(22) Filed: May 4, 2018

(65) Prior Publication Data

US 2018/0251450 A1    Sep. 6, 2018

Related U.S. Application Data

(63) Continuation of application No. PCT/EP2016/076315, filed on Nov. 2, 2016.

(30) Foreign Application Priority Data

Nov. 6, 2015 (EP) ..................................... 15193355

(51) Int. Cl.
| | | |
|---|---|---|
| *C07D 403/14* | (2006.01) | |
| *C07D 401/14* | (2006.01) | |
| *C07D 405/14* | (2006.01) | |
| *C07D 413/14* | (2006.01) | |
| *C07D 491/08* | (2006.01) | |
| *C07D 417/14* | (2006.01) | |
| *C07D 471/04* | (2006.01) | |
| *C07D 487/04* | (2006.01) | |
| *C07D 491/04* | (2006.01) | |
| *A61P 25/36* | (2006.01) | |
| *A61P 25/28* | (2006.01) | |
| *A61P 25/22* | (2006.01) | |
| *A61P 25/32* | (2006.01) | |
| *A61P 25/18* | (2006.01) | |

(Continued)

(52) U.S. Cl.
CPC ............ *C07D 403/14* (2013.01); *A61P 25/08* (2018.01); *A61P 25/16* (2018.01); *A61P 25/18* (2018.01); *A61P 25/22* (2018.01); *A61P 25/24* (2018.01); *A61P 25/28* (2018.01); *A61P 25/32* (2018.01); *A61P 25/36* (2018.01); *C07D 401/14* (2013.01); *C07D 405/14* (2013.01); *C07D 413/14* (2013.01); *C07D 417/14* (2013.01); *C07D 471/04* (2013.01); *C07D 487/04* (2013.01); *C07D 491/04* (2013.01); *C07D 491/08* (2013.01); *C07D 498/04* (2013.01); *A61K 45/06* (2013.01); *A61K 2300/00* (2013.01)

(58) Field of Classification Search
CPC .. C07D 401/14; C07D 403/14; C07D 405/14; C07D 413/14; C07D 417/14; C07D 471/04; C07D 487/04; C07D 491/04; C07D 491/08; C07D 498/04
See application file for complete search history.

(56) References Cited

U.S. PATENT DOCUMENTS

| 6,090,818 A | 7/2000 | Foulon et al. |
| 9,616,053 B2 | 4/2017 | Brunner et al. |

(Continued)

FOREIGN PATENT DOCUMENTS

| CA | 2196809 | 7/1995 |
| EP | 2895476 | 6/2016 |

(Continued)

OTHER PUBLICATIONS (ISR and Written Opinion of PCT/EP2015/064016 (dated Aug. 4, 2015)).

(Continued)

*Primary Examiner* — Valerie Rodriguez-Garcia
(74) *Attorney, Agent, or Firm* — Todd M. Crissey

(57) ABSTRACT

The present invention is concerned with indolin-2-one derivatives of general formula

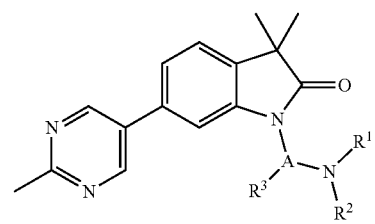

I wherein the substituents are defined in claim 1.

The compounds may be used in the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, effects in arthritis, autoimmune disease, viral and fungal infections, cardiovascular diseases, ophthalmology and inflammatory retinal diseases and balance problems, epilepsy and neurodevelopmental disorders with co-morbid epilepsy.

20 Claims, No Drawings

(51) Int. Cl.
*A61P 25/24* (2006.01)
*A61P 25/08* (2006.01)
*A61P 25/16* (2006.01)
*C07D 498/04* (2006.01)
*A61K 45/06* (2006.01)

(56) References Cited

U.S. PATENT DOCUMENTS

| | | |
|---|---|---|
| 2006/0253263 A1 | 11/2006 | Meshkin |
| 2008/0039496 A1 | 2/2008 | Blackburn et al. |
| 2011/0053936 A1 | 3/2011 | Eastwood et al. |
| 2016/0095844 A1* | 4/2016 | Brunner .............. C07D 405/14 424/715 |
| 2017/0101409 A1* | 4/2017 | Hilpert ................. A61K 45/06 |
| 2018/0251449 A1 | 9/2018 | Gaufreteau et al. |
| 2018/0251450 A1 | 9/2018 | Gaufreteau et al. |
| 2018/0251451 A1 | 9/2018 | Gaufreteau et al. |
| 2018/0251455 A1 | 9/2018 | Gaufreteau et al. |

FOREIGN PATENT DOCUMENTS

| | | |
|---|---|---|
| JP | H10-503503 A | 3/1998 |
| JP | 2004-501192 A | 1/2004 |
| JP | 2008-536941 A | 9/2008 |
| JP | 2009-541493 A | 11/2009 |
| TW | 201504223 A | 2/2015 |
| WO | 91/06545 A1 | 5/1991 |
| WO | 94/10171 | 5/1994 |
| WO | 96/04272 | 2/1996 |
| WO | 98/25901 A1 | 6/1998 |
| WO | 00/40581 | 7/2000 |
| WO | 02/00217 A1 | 1/2002 |
| WO | 2004/060902 A2 | 7/2004 |
| WO | 2005/108388 A1 | 11/2005 |
| WO | 2006/113864 A2 | 10/2006 |
| WO | 2006/113875 A2 | 10/2006 |
| WO | 2008/002946 A2 | 1/2008 |
| WO | 2008/046083 A2 | 4/2008 |
| WO | 2008/080970 A1 | 7/2008 |
| WO | 2008/080973 | 7/2008 |
| WO | 2009/124692 A1 | 10/2009 |
| WO | 2009/132774 A1 | 11/2009 |
| WO | 2010/066684 A2 | 6/2010 |
| WO | 2014/040969 A1 | 3/2014 |
| WO | 2014/202493 A1 | 12/2014 |
| WO | 2015/197567 | 12/2015 |
| WO | 2017/076842 | 5/2017 |
| WO | 2017/076852 | 5/2017 |
| WO | 2017/076931 | 5/2017 |
| WO | 2017/076932 | 5/2017 |

OTHER PUBLICATIONS

Anne E. King et al., "Nucleoside transporters: from scavengers to novel therapeutic targets" Trends in Pharmacological Science 27(8):416-425 ( 2006), Epub: Jul. 2006.

Daniela Alberati et al., "Pharmacological evaluation of a novel assay for detecting glycine transporter 1 inhibitors and their antipsychotic potential" Pharmacology, Biochemistry and Behavior 97:185-191 ( 2010), Dec. 2010.

Elena P. Calandre et al., "The Role of Antipsychotics in the Management of Fibromyalgia" CNS Drugs 26(2):135-153 ( 2012), Feb. 2012.

Gregory I Liou et al., "Diabetic retinopathy: Role of inflammation and potential therapies for anti-inflammation" World Journal of Diabetes 1(1):12-18 (Mar. 15, 2010).

ISR and Written Opinion of PCT/EP2016/076332 (dated Dec. 8, 2016).

ISR and Written Opinion of PCT/EP2016/076472 (dated Dec. 12, 2016).

ISR of PCT/EP2016/076315 (dated Jan. 4, 2017).

ISR of PCT/EP2016/076473 (dated Dec. 21. 2016).

* cited by examiner

INDOLIN-2-ONE DERIVATIVES
The present invention is concerned with indolin-2-one derivatives of general formula
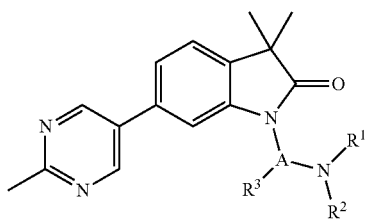
I
wherein
A is phenyl or a six membered heteroaryl group, containing one or two N atoms, selected from
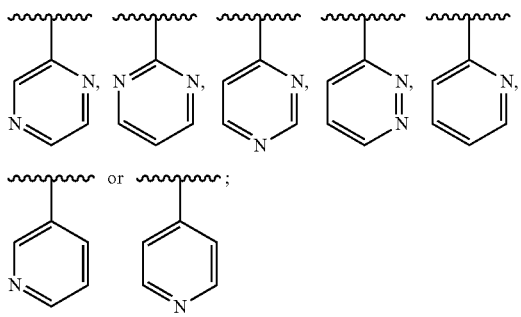
or the amine group —NR$^1$R$^2$ may form together with two neighboring carbon atoms from the group A an additional fused ring, selected from
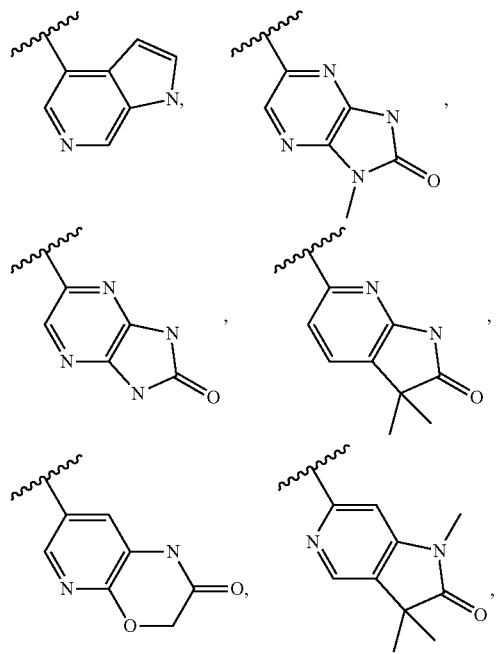
-continued
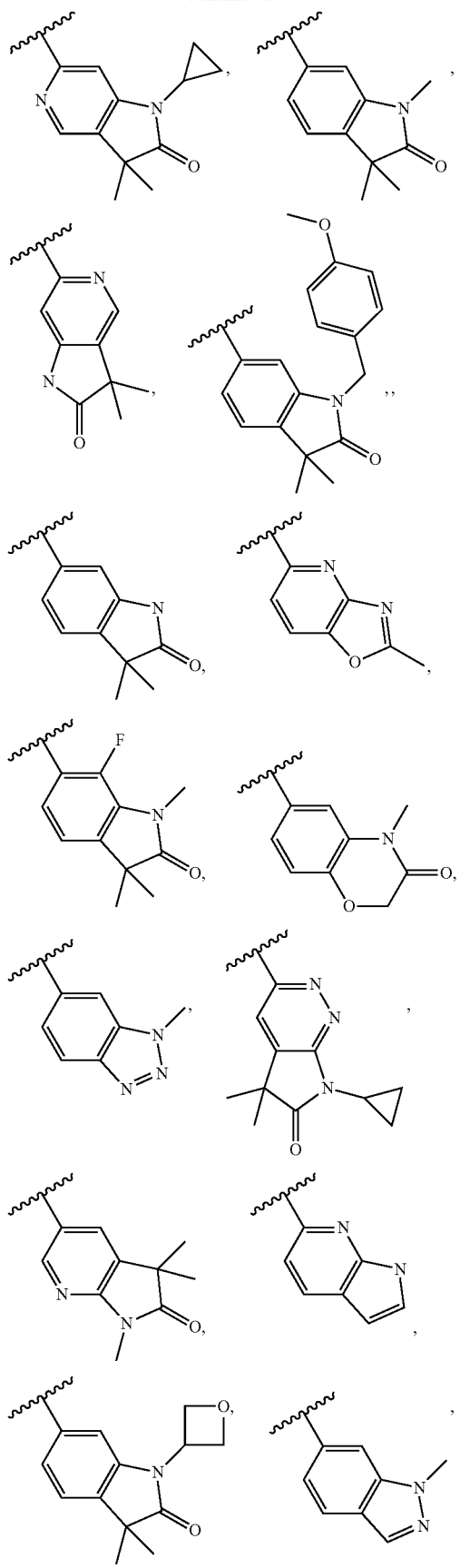

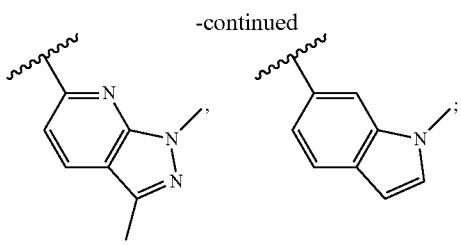

$R^1/R^2$ are independently from each other hydrogen, C(O)-lower alkyl, cycloalkyl, —(CH$_2$)$_2$-lower alkoxy, lower alkyl or oxetanyl;

or $R^1$ and $R^2$ may form together with the N atom to which they are attach the group

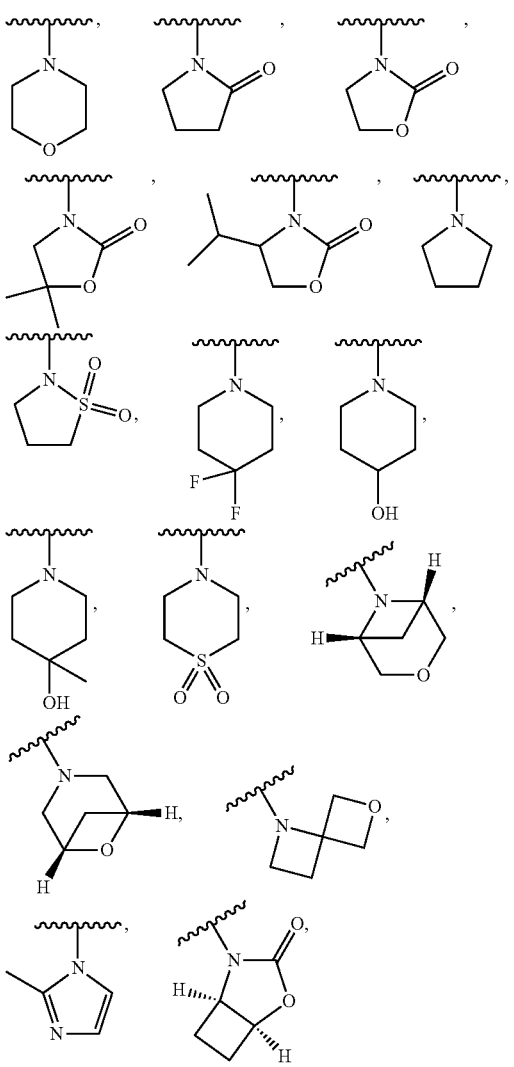

$R^3$ is hydrogen or lower alkyl;

as well as with a pharmaceutically acceptable salt thereof, with a racemic mixture, or with its corresponding enantiomer and/or optical isomer and/or stereoisomer thereof.

The amine group NR$^1$R$^2$ and R$^3$ may have different positions on A.

Now it has been found that the compounds of formula I may be used for the treatment of CNS diseases. The described compounds have been shown to reverse the L-687,414 ((3R,4R)-3 amino-1-hydroxy-4-methyl-pyrrolidin-2-one, a NMDA glycine site antagonist) induced hyperlocomotion, a behavioral pharmacodynamic mouse model for schizophrenia, described by D. Alberati et al. in *Pharmacology, Biochemistry and Behavior*, 97 (2010), 185-191. The authors described that hyperlocomotion induced by L-687,414 was inhibited by a series of known antipsychotic drugs. The compounds of formula I demonstrate marked activity in this model. These findings predict antipsychotic activity for the present compounds, making them useful for the treatment of positive (psychosis) and negative symptoms of schizophrenia, substance abuse, alcohol and drug addiction, obsessive-compulsive disorders, cognitive impairment, bipolar disorders, mood disorders, major depression, resistant depression, anxiety disorders, Alzheimer's disease, autism, Parkinson's disease, chronic pain, borderline personality disorder, sleep disturbances, chronic fatigue syndrome, stiffness, antiinflammatory effects in arthritis and balance problems, and treatment of epilepsy and neurodevelopmental disorders with co-morbid epilepsy.

In addition to the reversal of L-687,414 induced hyperlocomotion experiment as described above, some compounds of the present invention have been tested in SmartCube®, an automated system in which the behaviors of compound-treated mice in response to multiple challenges are captured by digital video and analyzed with computer algorithms (Roberds et al., *Frontiers in Neuroscience*, 2011, Vol. 5, Art. 103, 1-4; Vadim Alexandrov, Dani Brunner, Taleen Hanania, Emer Leahy *Eur. J Pharmacol.* 2015, 750, 82-99). In this way, the neuro-pharmacological effects of a test compound can be predicted by similarity to major classes of compounds, such as antipsychotics, anxiolytics and antidepressants. Examples 1, 3, 15, 18, 20, 39, 50 and 54 show similarity to atypical antipsychotics. The results are shown in Table 3.

In addition to the above-mentioned experiments, it has been shown that some of the compounds of formula I are also ENT1 inhibitors (equilibrative nucleoside transporter 1 protein). Therapeutic potential of ENT1 inhibitors is directly or indirectly (via effects of adenosine and/or adenosine receptor modulation) described in the literature for the treatment of the following diseases:

autoimmune disease (US 2006/253263), cancer (WO9857643), viral infections and fungal infections (WO2004060902), neurodegenerative disease, Parkinson's disease, Alzheimer's disease, Huntington's disease, amyotrophic lateral sclerosis, psychiatric diseases, substance abuse, ADHD, depression, epilepsy, anxiety, schizophrenia (WO0168105, EP 1252910, EP1612210, WO2009018275), autism spectrum disorders (Susan A. Masinoa, Masahito Kawamura Jr., Jessica L. Cotea, Rebecca B. Williams, David N. Ruskina, *Neuropharmacology*, 2013, 68, 116-121, pain (WO2009062990, WO2009064497), inflammation, asthma, (US 2007213296, *Inflammation research*, 2011, 60, 75-76), cardiovascular diseases (*Trends in Pharmacological science*, 2006, 27, 416-425), sleep disorders, (*Psychopharmacology*, 1987, 91, 434-439), and ophthalmology and inflammatory retinal diseases (*World Journal of Diabetes*, vol. 1, 12-18), epilepsy and neurodevelopmental disorders with co-morbid epilepsy (*ENT1 Inhibition Attenuates Epileptic Seizure Severity Via Regulation of Glutamatergic Neurotransmission*, Xu et al, *Neuromol Med* (2015) 17:1-11 and *Epigenetic changes induced by adenosine augmentation*

*therapy prevent epileptogenesis*, Williams-Karneshy et al *J Clin Invest.* 2013 August; 123(8):3552-63.

Schizophrenia is a complex mental disorder typically appearing in late adolescence or early adulthood with a world-wide prevalence of approximately 1% of the adult population, which has enormous social and economic impact. The criteria of the Association of European Psychiatrists (ICD) and the American Psychiatric Association (DSM) for the diagnosis of schizophrenia require two or more characteristic symptoms to be present: delusions, hallucinations, disorganized speech, grossly disorganized or catatonic behavior (positive symptoms), or negative symptoms (alogia, affective flattening, lack of motivation, anhedonia). As a group, people with schizophrenia have functional impairments that may begin in childhood, continue throughout adult life and make most patients unable to maintain normal employment or otherwise have normal social function. They also have a shortened lifespan compared to the general population, and suffer from an increased prevalence of a wide variety of other neuropsychiatric syndromes, including substance abuse, obsessive-compulsive symptoms and abnormal involuntary movements. Schizophrenia is also associated with a wide range of cognitive impairments, bipolar disorders, major depression and anxiety disorders, the severity of which limits the functioning of patients, even when psychotic symptoms are well controlled. The primary treatment of schizophrenia is antipsychotic medications. Antipsychotics, for example risperidone and olanzapine, however, fail to significantly ameliorate the negative symptoms and cognitive dysfunction.

Antipsychotic drugs have shown clinical efficacy for the treatment of the following diseases:
Fibromyalgia, which is a syndrome characterized by chronic generalized pain associated with different somatic symptoms, such as sleep disturbances, fatigue, stiffness, balance problems, hypersensitivity to physical and psychological environmental stimuli, depression and anxiety (*CNS Drugs*, 2012, 26, 2, 135-53).
Schizoaffective disorders: includes psychotic and affective symptoms, this disorder falls on a spectrum between bipolar disorders (with depressive and manic episodes, alcohol and drug addiction, substance abuse) and schizophrenia. *J. Clin. Psychiatry,* 2010, 71, S2, 14-9, Pediatr. Drugs 2011, 13, 5, 291-302
Major depression: *BMC Psychiatry* 2011, 11, 86
Treatment resistent depression: *Journal of Psychopharmacology,* 0(0) 1-16
Anxiety: *European Neuropsychopharmacology,* 2011, 21, 429-449
Bipolar disorders: *Encephale, International J. of Neuropsychopharmacology,* 2011, 14, 1029-104, *International J. of Neuropsychopharmacology,* 2012, 1-12; *J. of Neuropsychopharmacology,* 2011, 0, 0, 1-15
Mood disorders: *J. Psychopharmacol.* 2012, January 11, *CNS Drugs,* 2010, 2, 131-61
Autism: *Current opinion in pediatrics,* 2011, 23, 621-627; *J. Clin. Psychiatry,* 2011, 72, 9, 1270-1276
Alzheimer's disease: *J. Clin. Psychiatry,* 2012, 73, 1, 121-128
Parkinson's disease: *Movement Disorders,* 2011, 26, 6
Chronic fatigue syndrome: *European Neuropsychopharmacology,* 2011, 21, 282-286
Borderline Personality disorder: *J. Clin. Psychiatry,* 2011, 72, 10, 1363-1365 *J. Clin. Psychiatry,* 2011, 72, 10, 1353-1362
Anti-inflammatory effects in arthritis: *European J. of Pharmacology,* 2012, 678, 55-60

Objects of the present invention are novel compounds of formula I and the use of compounds of formula I and their pharmaceutically acceptable salts for the treatment of CNS diseases related to positive (psychosis) and negative symptoms of schizophrenia, substance abuse, alcohol and drug addiction, obsessive-compulsive disorders, cognitive impairment, bipolar disorders, mood disorders, major depression, treatment resistant depression, anxiety disorders, Alzheimer's disease, autism, Parkinson's disease, chronic pain, borderline personality disorder, neurodegenerative disease, sleep disturbances, chronic fatigue syndrome, stiffness, inflammatory disease, asthma, Huntington's disease, ADHD, amyotrophic lateral sclerosis, arthritis, autoimmune disease, viral and fungal infections, cardiovascular diseases, ophthalmology and inflammatory retinal diseases and balance problems, epilepsy and neurodevelopmental disorders with co-morbid epilepsy.

Further objects of the present invention are medicaments containing such novel compounds as well as methods for preparation of compounds of formula I, a combination of compounds of formula I with marketed antipsychotics, antidepressants, anxiolytics or mood stabilizers, and methods for the treatment of CNS disorders as mentioned above.

Encompassed by the present invention are corresponding prodrugs of compounds of formula I.

A common antipsychotic drug for the treatment of schizophrenia is olanzapine. Olanzapine (Zyprexa) belongs to a drug class known as atypical antipsychotics. Other members of this class include for example clozapine (Clozaril), risperidone (Risperdal), aripiprazole (Abilify) and ziprasidone (Geodon).

Olanzapine is approved for the treatment of psychotic disorders, long term treatment of bipolar disorders and in combination with fluoxetine for the treatment of depressive episodes associated with bipolar disorders and for the treatment of resistant depression. The compounds of the present invention may be combined with antipsychotic drugs like olanzapine (Zyprexa), clozapine (Clozaril), risperidone (Risperdal), aripiprazole (Abilify), amisulpride (Solian), asenapine (Saphris), blonanserin (Lonasen), clotiapine (Entumine), iloperidone (Fanapt), lurasidone (Latuda), mosapramine (Cremin), paliperidone (Invega), perospirone (Lullan), quetiapine (Seroquel), remoxipride (Roxiam), sertindole (Serdolect), sulpiride (Sulpirid, Eglonyl), ziprasidone (Geodon, Zeldox), zotepine (Nipolept), haloperidol (Haldol, Serenace), droperidol (Droleptan), chlorpromazine (Thorazine, Largactil), fluphenazine (Prolixin), perphenazine (Trilafon), prochlorperazine (Compazine), thioridazine (Mellaril, Melleril), trifluoperazine (Stelazine), triflupromazine (Vesprin), levomepromazine (Nozinan), promethazine (Phenergan), pimozide (Orap) and cyamemazine (Tercian).

One preferred embodiment of the invention is a combination, wherein the marketed antipsychotic drug is olanzapine (Zyprexa), clozapine (Clozaril), risperidone (Risperdal), aripiprazole (Abilify) or ziprasidone.

Furthermore, the compounds of the present invention can be combined with antidepressants such as selective serotonin reuptake inhibitors [Citalopram (Celexa), Escitalopram (Lexapro, Cipralex), Paroxetine (Paxil, Seroxat), Fluoxetine (Prozac), Fluvoxamine (Luvox), Sertraline (Zoloft, Lustral)], serotonin-norepinephrine reuptake inhibitors [Duloxetine (Cymbalta), Milnacipran (Ixel, Savella), Venlafaxine (Effexor), Desvenlafaxine (Pristiq), Tramadol (Tramal, Ultram), Sibutramine (Meridia, Reductil)], serotonin antagonist and reuptake inhibitors [Etoperidone (Axiomin, Etonin), Lubazodone (YM-992, YM-35,995), Nefazodone (Serzone, Nefadar), Trazodone (Desyrel)], norepinephrine reuptake inhibitors [Reboxetine (Edronax), Viloxazine (Vivalan), Atomoxetine (Strattera)], norepinephrine-dopamine reuptake inhibitors [Bupropion (Wellbutrin, Zyban), Dexmethylphenidate (Focalin), Methylphenidate (Ritalin, Concerta)], norepinephrine-dopamine releasing agents [Amphetamine (Adderall), Dextroamphetamine (Dexedrine), Dextromethamphetamine (Desoxyn), Lisdexamfetamine (Vyvanse)], tricyclic antidepressants [Amitriptyline (Elavil, Endep), Clomipramine (Anafranil), Desipramine (Norpramin, Pertofrane), Dosulepin [Dothiepin] (Prothiaden), Doxepin (Adapin, Sinequan), Imipramine (Tofranil), Lofepramine (Feprapax, Gamanil, Lomont), Nortriptyline (Pamelor), Protriptyline (Vivactil), Trimipramine (Surmontil)], tetracyclic antidepressants [Amoxapine (Asendin), Maprotiline (Ludiomil), Mianserin (Bolvidon, Norval, Tolvon), Mirtazapine (Remeron)], monoamine oxidase inhibitors [Isocarboxazid (Marplan), Moclobemide (Aurorix, Manerix), Phenelzine (Nardil), Selegiline [L-Deprenyl] (Eldepryl, Zelapar, Emsam), Tranylcypromine (Parnate), Pirlindole (Pirazidol)], 5-HT1A Receptor Agonists [Buspirone (Buspar), Tandospirone (Sediel), Vilazodone (Viibryd)], 5-HT2 Receptor Antagonists [Agomelatine (Valdoxan), Nefazodone (Nefadar, Serzone), selective Serotonin Reuptake Enhancers [Tianeptine].

A preferred embodiment of this invention is a combination, wherein the marketed anti-depressive drug is citalopram (Celexa), escitalopram (Lexapro, Cipralex), paroxetine (Paxil, Seroxat), fluoxetine (Prozac), sertraline (Zoloft, Lustral) duloxetine (Cymbalta), milnacipran (Ixel, Savella), venlafaxine (Effexor), or mirtazapine (Remeron).

Compounds can also be combined with anxiolytics such as Alprazolam (Helex, Xanax, Xanor, Onax, Alprox, Restyl, Tafil, Paxal), Bretazenil, Bromazepam (Lectopam, Lexotanil, Lexotan, Bromam), Brotizolam (Lendormin, Dormex, Sintonal, Noctilan), Chlordiazepoxide (Librium, Risolid, Elenium), Cinolazepam (Gerodorm), Clonazepam (Rivotril, Klonopin, Iktorivil, Paxam), Clorazepate (Tranxene, Tranxilium), Clotiazepam (Veratran, Clozan, Rize), Cloxazolam (Sepazon, Olcadil), Delorazepam (Dadumir), Diazepam (Antenex, Apaurin, Apzepam, Apozepam, Hexalid, Pax, Stesolid, Stedon, Valium, Vival, Valaxona), Estazolam (ProSom), Etizolam (Etilaam, Pasaden, Depas), Flunitrazepam (Rohypnol, Fluscand, Flunipam, Ronal, Rohydorm), Flurazepam (Dalmadorm, Dalmane), Flutoprazepam (Restas), Halazepam (Paxipam), Ketazolam (Anxon), Loprazolam (Dormonoct), Lorazepam (Ativan, Temesta, Tavor, Lorabenz), Lormetazepam (Loramet, Noctamid, Pronoctan), Medazepam (Nobrium), Midazolam (Dormicum, Versed, Hypnovel, Dormonid), Nimetazepam (Erimin), Nitrazepam (Mogadon, Alodorm, Pacisyn, Dumolid, Nitrazadon), Nordazepam (Madar, Stilny), Oxazepam (Seresta, Serax, Serenid, Serepax, Sobril, Oxabenz, Oxapax), Phenazepam (Phenazepam), Pinazepam (Domar), Prazepam (Lysanxia, Centrax), Premazepam, Quazepam (Doral), Temazepam (Restoril, Normison, Euhypnos, Temaze, Tenox), Tetrazepam (Mylostan), Triazolam (Halcion, Rilamir), Clobazam (Frisium, Urbanol), Eszopiclone (Lunesta), Zaleplon (Sonata, Starnoc), Zolpidem (Ambien, Nytamel, Stilnoct, Stilnox, Zoldem, Zolnod), Zopiclone (Imovane, Rhovane, Ximovan; Zileze; Zimoclone; Zimovane; Zopitan; Zorclone), Pregabalin (Lyrica) and Gabapentin (Fanatrex, Gabarone, Gralise, Neurontin, Nupentin).

One preferred embodiment of the invention is a combination, wherein the marketed anxiolytic drug is alprazolam (Helex, Xanax, Xanor, Onax, Alprox, Restyl, Tafil, Paxal), chlordiazepoxide (Librium, Risolid, Elenium), clonazepam (Rivotril, Klonopin, Iktorivil, Paxam), diazepam (Antenex, Apaurin, Apzepam, Apozepam, Hexalid, Pax, Stesolid, Stedon, Valium, Vival, Valaxona), Estazolam (ProSom), eszopiclone (Lunesta), zaleplon (Sonata, Starnoc), zolpidem (Ambien, Nytamel, Stilnoct, Stilnox, Zoldem, Zolnod), pregabalin (Lyrica) or gabapentin (Fanatrex, Gabarone, Grali se, Neurontin, Nupentin).

A further object of the invention is a combination with mood stabilizers such as Carbamazepine (Tegretol), Lamotrigine (Lamictal), Lithium (Eskalith, Lithane, Lithobid), and Valproic Acid (Depakote).

Compounds can also be combined with procognitive compounds such as donepezil (Aricept), galantamine (Razadyne), rivastigmine (Exelon) and memantine (Namenda).

The preferred indications using the compounds of the present invention are psychotic diseases like schizophrenia.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes an alkyl group as defined above, wherein the alkyl residue is attached via an oxygen atom.

The term "cycloalkyl" denotes an alkyl ring with 3-6 carbon ring atoms.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula IA

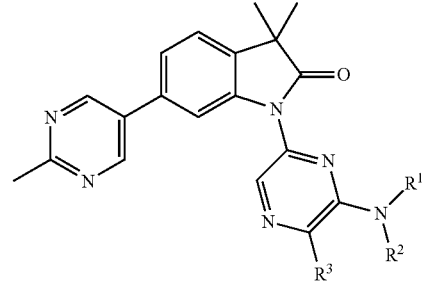

IA wherein
R$^1$/R$^2$ are independently from each other hydrogen, C(O)-lower alkyl, cycloalkyl, —(CH$_2$)$_2$-lower alkoxy, lower alkyl or oxetanyl;
or R$^1$ and R$^2$ may form together with the N atom to which they are attach the group

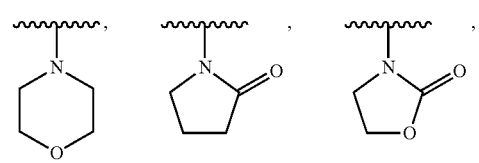

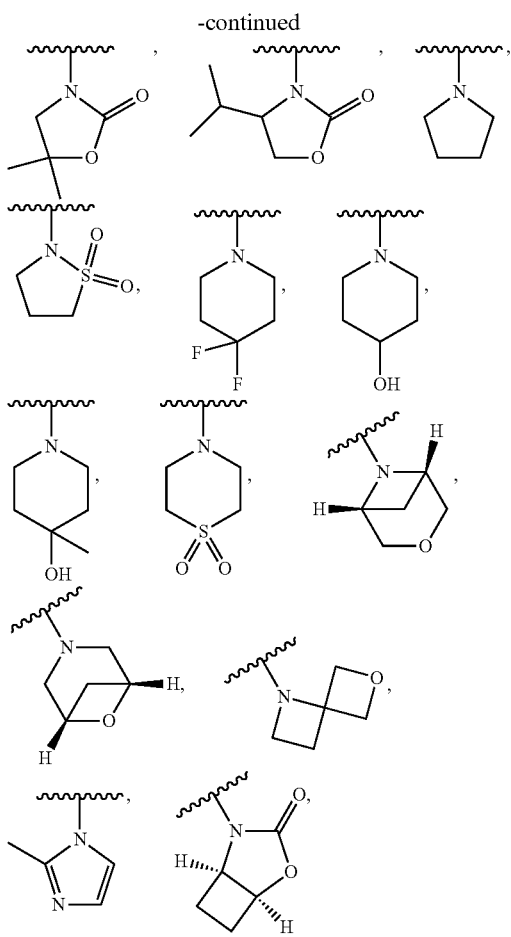

R³ is hydrogen or lower alkyl;
and wherein the amine group NR¹R² may also be in p-position and R³ may be in meta position,
as well as a pharmaceutically acceptable salt thereof, a racemic mixture, or its corresponding enantiomer and/or optical isomer and/or stereoisomer thereof, for example the compounds 3,3-dimethyl-6-(2-methylpyrimidin-5-yl)-1-(6-morpholinopyrazin-2-yl)indolin-2-one
1-(6-aminopyrazin-2-yl)-3,3-dimethyl-6-(2-methylpyrimidin-5-yl)indolin-2-one
3,3-dimethyl-6-(2-methylpyrimidin-5-yl)-1-(6-(2-oxopyrrolidin-1-yl)pyrazin-2-yl)indolin-2-one
3,3-dimethyl-6-(2-methylpyrimidin-5-yl)-1-(6-(pyrrolidin-1-yl)pyrazin-2-yl)indolin-2-one
N-(6-(3,3-dimethyl-6-(2-methylpyrimidin-5-yl)-2-oxoindolin-1-yl)pyrazin-2-yl)acetamide
1-(6-(4,4-difluoropiperidin-1-yl)pyrazin-2-yl)-3,3-dimethyl-6-(2-methylpyrimidin-5-yl)indolin-2-one
1-(6-(cyclopropylamino)pyrazin-2-yl)-3,3-dimethyl-6-(2-methylpyrimidin-5-yl)indolin-2-one
1-[6-(2-methoxyethylamino)pyrazin-2-yl]-3,3-dimethyl-6-(2-methylpyrimidin-5-yl)indol-2-one
1-(6-(4-hydroxypiperidin-1-yl)pyrazin-2-yl)-3,3-dimethyl-6-(2-methylpyrimidin-5-yl)indolin-2-one
1-(6-(1,1-dioxidothiomorpholino)pyrazin-2-yl)-3,3-dimethyl-6-(2-methylpyrimidin-5-yl)indolin-2-one
1-(6-(4-hydroxy-4-methylpiperidin-1-yl)pyrazin-2-yl)-3,3-dimethyl-6-(2-methylpyrimidin-5-yl)indolin-2-one
1-(6-((2-methoxyethyl)(methyl)amino)pyrazin-2-yl)-3,3-dimethyl-6-(2-methylpyrimidin-5-yl)indolin-2-one
1-(6-((1R,5S)-3-oxa-6-azabicyclo[3.1.1]heptan-6-yl)pyrazin-2-yl)-3,3-dimethyl-6-(2-methylpyrimidin-5-yl)indolin-2-one
1-(6-(6-oxa-1-azaspiro[3.3]heptan-1-yl)pyrazin-2-yl)-3,3-dimethyl-6-(2-methylpyrimidin-5-yl)indolin-2-one
3-(6-(3,3-dimethyl-6-(2-methylpyrimidin-5-yl)-2-oxoindolin-1-yl)pyrazin-2-yl)oxazolidin-2-one
1-(6-((1R,5S)-6-oxa-3-azabicyclo[3.1.1]heptan-3-yl)pyrazin-2-yl)-3,3-dimethyl-6-(2-methylpyrimidin-5-yl)indolin-2-one
3,3-dimethyl-6-(2-methylpyrimidin-5-yl)-1-(6-(oxetan-3-ylamino)pyrazin-2-yl)indolin-2-one
3,3-dimethyl-1-(5-methyl-6-morpholinopyrazin-2-yl)-6-(2-methylpyrimidin-5-yl)indolin-2-one
1-(6-((2-methoxyethyl)amino)-5-methylpyrazin-2-yl)-3,3-dimethyl-6-(2-methylpyrimidin-5-yl)indolin-2-one
3-(6-(3,3-dimethyl-6-(2-methylpyrimidin-5-yl)-2-oxoindolin-1-yl)-3-methylpyrazin-2-yl)oxazolidin-2-one
(R)-3-(6-(3,3-dimethyl-6-(2-methylpyrimidin-5-yl)-2-oxoindolin-1-yl)pyrazin-2-yl)-4-isopropyloxazolidin-2-one
(S)-3-(6-(3,3-dimethyl-6-(2-methylpyrimidin-5-yl)-2-oxoindolin-1-yl)pyrazin-2-yl)-4-isopropyloxazolidin-2-one
3,3-dimethyl-6-(2-methylpyrimidin-5-yl)-1-(5-morpholinopyrazin-2-yl)indolin-2-one
3,3-dimethyl-1-(5-(2-methyl-1H-imidazol-1-yl)pyrazin-2-yl)-6-(2-methylpyrimidin-5-yl)indolin-2-one
1-(5-((1R,5S)-3-oxa-6-azabicyclo[3.1.1]heptan-6-yl)pyrazin-2-yl)-3,3-dimethyl-6-(2-methylpyrimidin-5-yl)indolin-2-one
1-(5-((2-hydroxyethyl)amino)pyrazin-2-yl)-3,3-dimethyl-6-(2-methylpyrimidin-5-yl)indolin-2-one
rac-(1S,5R)-4-(6-(3,3-dimethyl-6-(2-methylpyrimidin-5-yl)-2-oxoindolin-1-yl)pyrazin-2-yl)-2-oxa-4-azabicyclo[3.2.0]heptan-3-one
3-(6-(3,3-dimethyl-6-(2-methylpyrimidin-5-yl)-2-oxoindolin-1-yl)pyrazin-2-yl)-5,5-dimethyloxazolidin-2-one or
1-(6-(1,1-dioxidoisothiazolidin-2-yl)pyrazin-2-yl)-3,3-dimethyl-6-(2-methylpyrimidin-5-yl)indolin-2-one.

One embodiment of the invention are compounds of formula IB

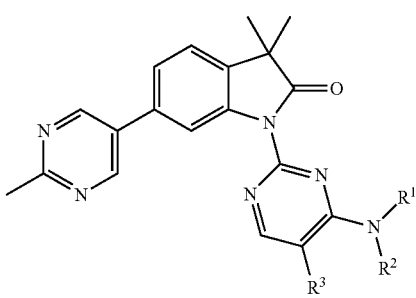

IB wherein
R¹/R² are independently from each other hydrogen, C(O)-lower alkyl, cycloalkyl, —(CH₂)₂-lower alkoxy, lower alkyl or oxetanyl;
or R¹ and R² may form together with the N atom to which they are attached the group

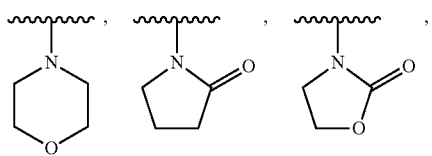

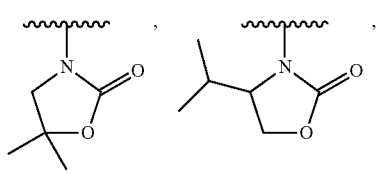

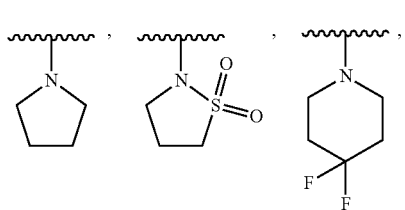

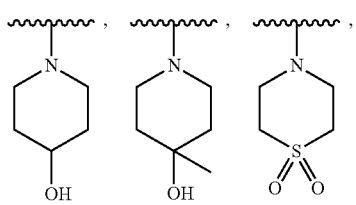

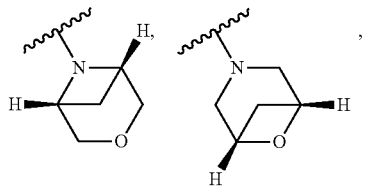

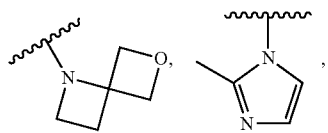

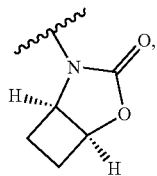

$R^3$ is hydrogen or lower alkyl;
and wherein the amine group $NR^1R^2$ and $R^3$ may be in other positions,
as well as a pharmaceutically acceptable salt thereof, a racemic mixture, or its corresponding enantiomer and/or optical isomer and/or stereoisomer thereof, for example the compound
3,3-dimethyl-6-(2-methylpyrimidin-5-yl)-1-(4-morpholinopyrimidin-2-yl)indolin-2-one.

One embodiment of the invention are compounds of formula IC

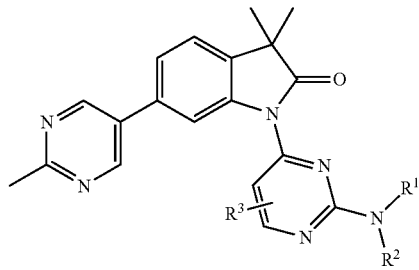

IC wherein $R^1/R^2$ are independently from each other hydrogen, C(O)-lower alkyl, cycloalkyl, —(CH$_2$)$_2$-lower alkoxy, lower alkyl or oxetanyl;

or $R^1$ and $R^2$ may form together with the N atom to which they are attached the group

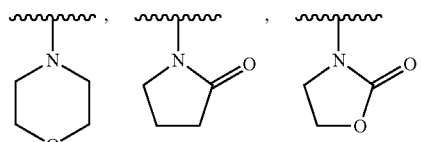

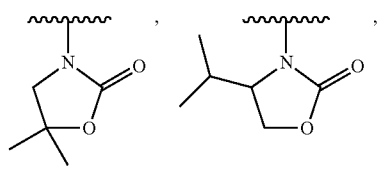

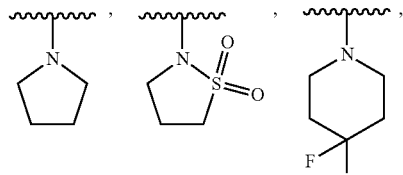

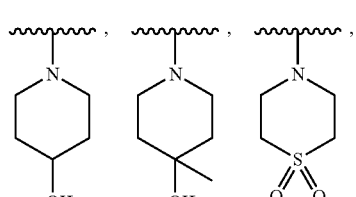

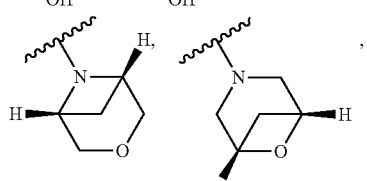

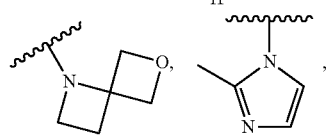

-continued

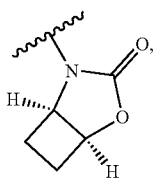

$R^3$ is hydrogen or lower alkyl;

and wherein the amine group $NR^1R^2$ may be in other positions, as well as a pharmaceutically acceptable salt thereof, a racemic mixture, or its corresponding enantiomer and/or optical isomer and/or stereoisomer thereof, for example the compound 3,3-dimethyl-6-(2-methylpyrimidin-5-yl)-1-(2-morpholinopyrimidin-4-yl)indolin-2-one.

One embodiment of the invention are compounds of formula ID

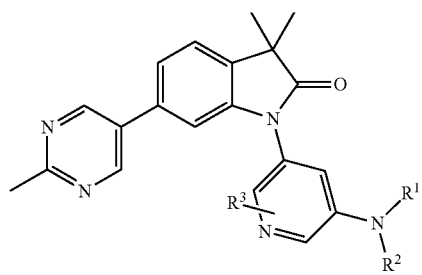

ID wherein $R^1/R^2$ are independently from each other hydrogen, C(O)-lower alkyl, cycloalkyl, —(CH$_2$)$_2$-lower alkoxy, lower alkyl or oxetanyl;

or $R^1$ and $R^2$ may form together with the N atom to which they are attached the group

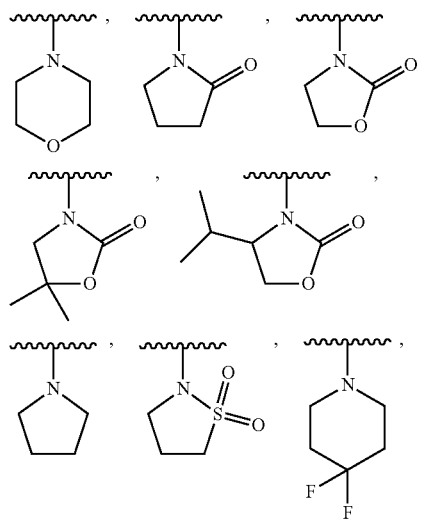

-continued

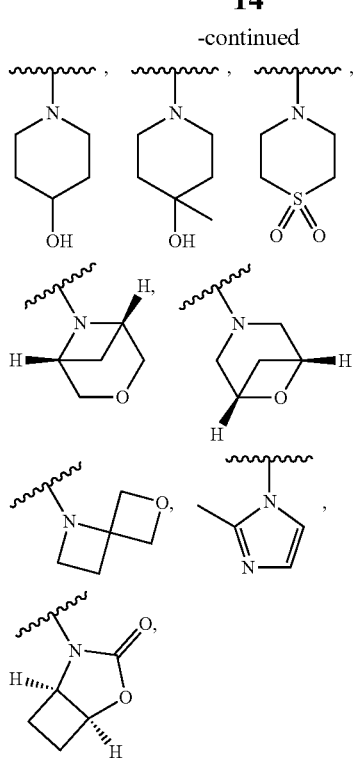

$R^3$ is hydrogen or lower alkyl;

and wherein the amine group $NR^1R^2$ may be in other positions, as well as a pharmaceutically acceptable salt thereof, a racemic mixture, or its corresponding enantiomer and/or optical isomer and/or stereoisomer thereof, for example the compounds 1-(5-aminopyridin-3-yl)-3,3-dimethyl-6-(2-methylpyrimidin-5-yl)indolin-2-one or 3,3-dimethyl-6-(2-methylpyrimidin-5-yl)-1-(5-morpholinopyridin-3-yl)indolin-2-one.

One embodiment of the invention are compounds of formula IE

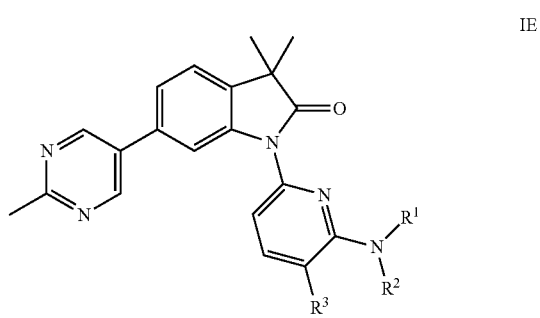

IE wherein $R^1/R^2$ are independently from each other hydrogen, C(O)-lower alkyl, cycloalkyl, —(CH$_2$)$_2$-lower alkoxy, lower alkyl or oxetanyl;

or $R^1$ and $R^2$ may form together with the N atom to which they are attached the group

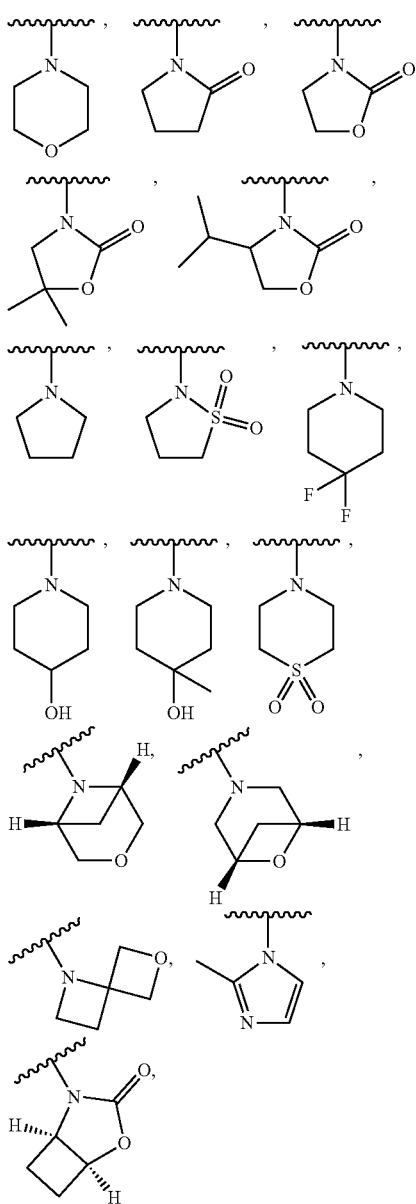

$R^3$ is hydrogen or lower alkyl;
and wherein the amine group $NR^1R^2$ and $R^3$ may be in other positions,
as well as a pharmaceutically acceptable salt thereof, a racemic mixture, or its corresponding enantiomer and/or optical isomer and/or stereoisomer thereof, for example the compounds
3,3-dimethyl-6-(2-methylpyrimidin-5-yl)-1-(6-morpholinopyridin-2-yl)indolin-2-one
3-(6-(3,3-dimethyl-6-(2-methylpyrimidin-5-yl)-2-oxoindolin-1-yl)pyridin-2-yl)oxazolidin-2-one
1-(6-amino-5-methylpyridin-2-yl)-3,3-dimethyl-6-(2-methylpyrimidin-5-yl)indolin-2-one
N-(6-(3,3-dimethyl-6-(2-methylpyrimidin-5-yl)-2-oxoindolin-1-yl)-3-methylpyridin-2-yl)acetamide
3,3-dimethyl-1-(5-methyl-6-morpholinopyridin-2-yl)-6-(2-methylpyrimidin-5-yl)indolin-2-one or
3-(6-(3,3-dimethyl-6-(2-methylpyrimidin-5-yl)-2-oxoindolin-1-yl)-3-methylpyridin-2-yl)oxazolidin-2-one.

One embodiment of the invention are compounds of formula IF

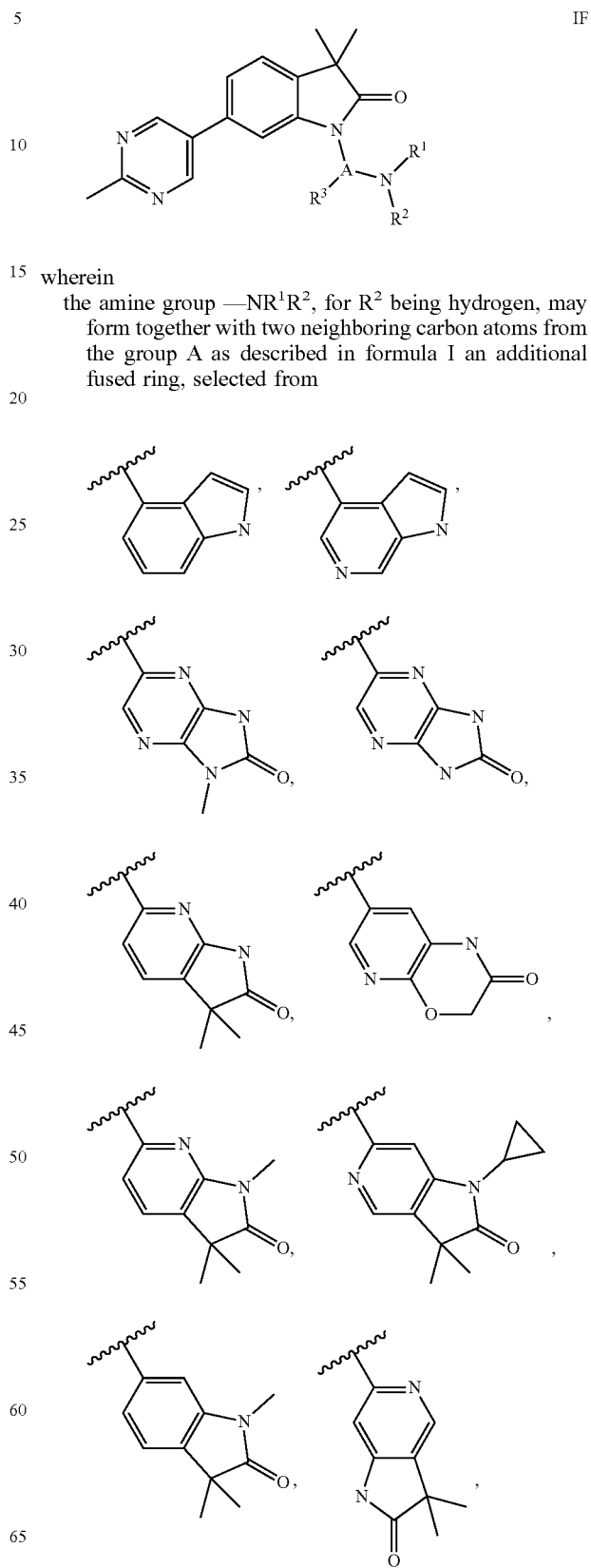

wherein
the amine group $—NR^1R^2$, for $R^2$ being hydrogen, may form together with two neighboring carbon atoms from the group A as described in formula I an additional fused ring, selected from -continued

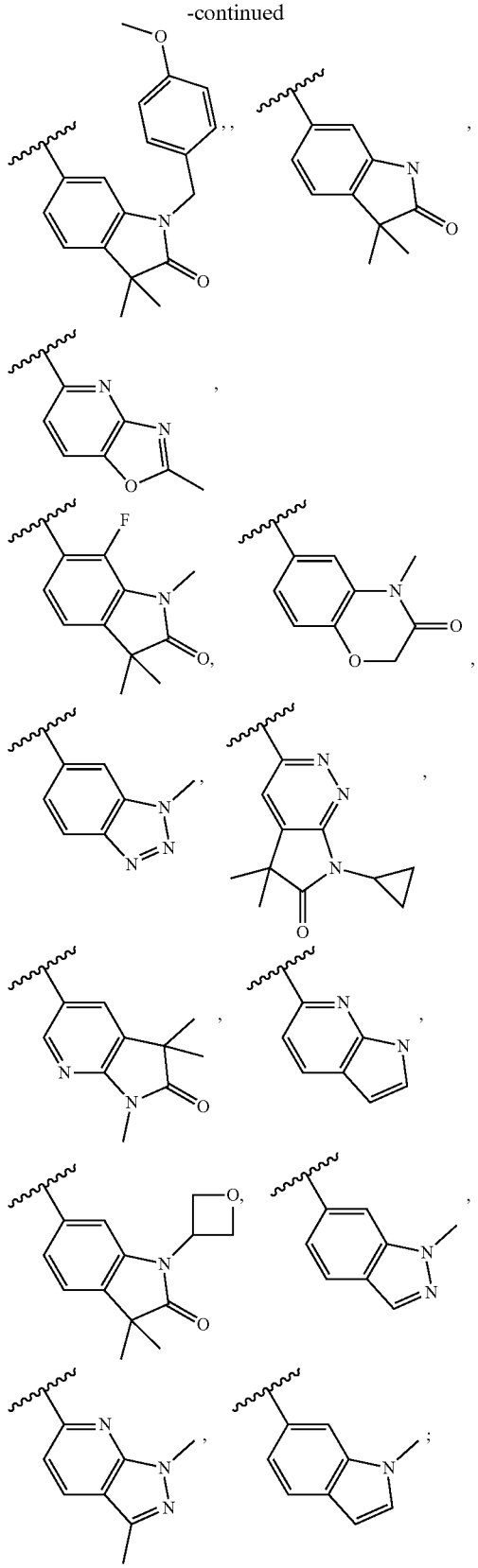

R³ is hydrogen;
as well as with a pharmaceutically acceptable salt thereof, with a racemic mixture, or with its corresponding enantiomer and/or optical isomer and/or stereoisomer thereof, for example the compounds 1-(1H-indol-4-yl)-3,3-dimethyl-6-(2-methylpyrimidin-5-yl) indolin-2-one
3,3-dimethyl-6-(2-methylpyrimidin-5-yl)-1-(1H-pyrrolo[2,3-c]pyridin-4-yl)indolin-2-one
5-(3,3-dimethyl-6-(2-methylpyrimidin-5-yl)-2-oxoindolin-1-yl)-1-methyl-1H-imidazo[4,5-b]pyrazin-2(3H)-one
5-(3,3-dimethyl-6-(2-methylpyrimidin-5-yl)-2-oxoindolin-1-yl)-1H-imidazo[4,5-b]pyrazin-2(3H)-one
6-(3,3-dimethyl-6-(2-methylpyrimidin-5-yl)-2-oxoindolin-1-yl)-3,3-dimethyl-1H-pyrrolo[2,3-b]pyridin-2(3H)-one
7-(3,3-dimethyl-6-(2-methylpyrimidin-5-yl)-2-oxoindolin-1-yl)-1H-pyrido[2,3-b][1,4]oxazin-2(3H)-one
6-(3,3-dimethyl-6-(2-methylpyrimidin-5-yl)-2-oxoindolin-1-yl)-1,3,3-trimethyl-1H-pyrrolo[2,3-b]pyridin-2(3H)-one
1-cyclopropyl-6-(3,3-dimethyl-6-(2-methylpyrimidin-5-yl)-2-oxoindolin-1-yl)-3,3-dimethyl-1H-pyrrolo[3,2-c]pyridin-2(3H)-one
1',3,3,3',3'-pentamethyl-6-(2-methylpyrimidin-5-yl)-[1,6'-biindoline]-2,2'-dione
1'-(4-methoxybenzyl)-3,3,3',3'-tetramethyl-6-(2-methylpyrimidin-5-yl)-[1,6'-biindoline]-2,2'-dione
6-(3,3-dimethyl-6-(2-methylpyrimidin-5-yl)-2-oxoindolin-1-yl)-3,3-dimethyl-1H-pyrrolo[3,2-c]pyridin-2(3H)-one
3,3,3',3'-tetramethyl-6-(2-methylpyrimidin-5-yl)-[1,6'-biindoline]-2,2'-dione
3,3-dimethyl-1-(2-methyloxazolo[4,5-b]pyridin-5-yl)-6-(2-methylpyrimidin-5-yl)indolin-2-one
7'-fluoro-1',3,3,3',3'-pentamethyl-6-(2-methylpyrimidin-5-yl)-[1,6'-biindoline]-2,2'-dione
6-(3,3-dimethyl-6-(2-methylpyrimidin-5-yl)-2-oxoindolin-1-yl)-4-methyl-2H-benzo[b][1,4]oxazin-3(4H)-one
3,3-dimethyl-1-(1-methyl-1H-benzo[d][1,2,3]triazol-6-yl)-6-(2-methylpyrimidin-5-yl)indolin-2-one
7-cyclopropyl-3-(3,3-dimethyl-6-(2-methylpyrimidin-5-yl)-2-oxoindolin-1-yl)-5,5-dimethyl-5H-pyrrolo[2,3-c]pyridazin-6(7H)-one
5-(3,3-dimethyl-6-(2-methylpyrimidin-5-yl)-2-oxoindolin-1-yl)-1,3,3-trimethyl-1H-pyrrolo[2,3-b]pyridin-2(3H)-one
3,3-dimethyl-6-(2-methylpyrimidin-5-yl)-1-(1H-pyrrolo[2,3-b]pyridin-6-yl)indolin-2-one
3,3,3',3'-tetramethyl-6-(2-methylpyrimidin-5-yl)-1'-(oxetan-3-yl)-[1,6'-biindoline]-2,2'-dione
3,3-dimethyl-1-(1-methyl-1H-indazol-6-yl)-6-(2-methylpyrimidin-5-yl)indolin-2-one
1-(1,3-dimethyl-1H-pyrazolo[3,4-b]pyridin-6-yl)-3,3-dimethyl-6-(2-methylpyrimidin-5-yl)indolin-2-one or
3,3-dimethyl-1-(1-methyl-1H-indol-6-yl)-6-(2-methylpyrimidin-5-yl)indolin-2-one.

The present compounds of formula I and their pharmaceutically acceptable salts can be prepared by methods known in the art, for example, by processes described below, which processes comprise
a) reacting a compound of formula

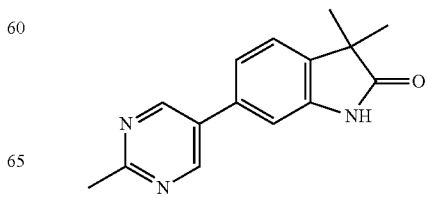

1 with a compound of formula

Y-A(R³)—NR¹R²   2 to a compound of formula

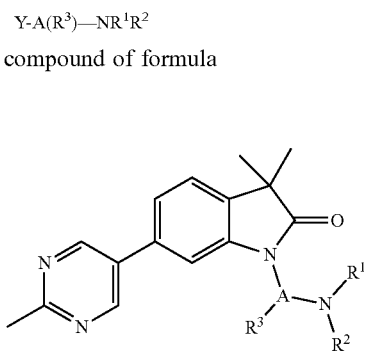

I wherein Y is Cl, Br or I and the other groups have the meaning as described above and, if desired, converting the compounds obtained into pharmaceutically acceptable acid addition salts or b) reacting a compound of formula 4

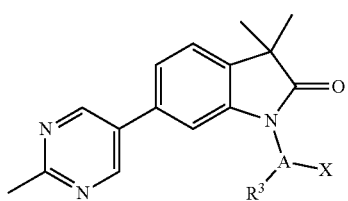

4 with HNR¹R²
to a compound of formula I

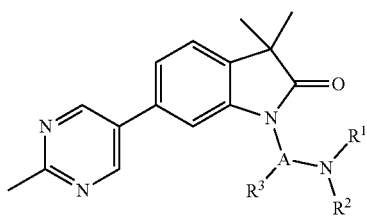

I wherein X is Cl, Br or I and the other groups have the meaning as described above and, if desired, converting the compounds obtained into pharmaceutically acceptable acid addition salts.

The preparation of compounds of formula I of the present invention may be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Scheme 1

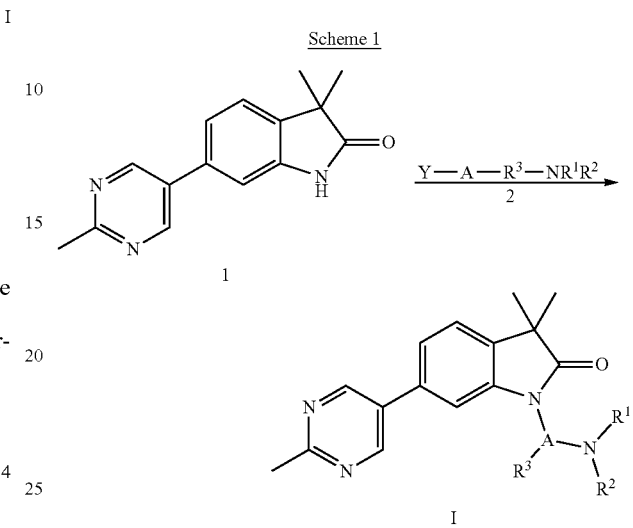

Compounds of formula I with A=substituted pyrazines, pyrimidines, pyridazines, pyridines, and fused rings can be prepared by coupling compounds 1 (WO2014/202493 A1) with aryl-halogenides 2 (Y=Cl, Br, I) in the presence of copper(I)iodide, a ligand such as N,N'-dimethylethylendiamine and a base, e.g. potassium carbonate.

Scheme 2

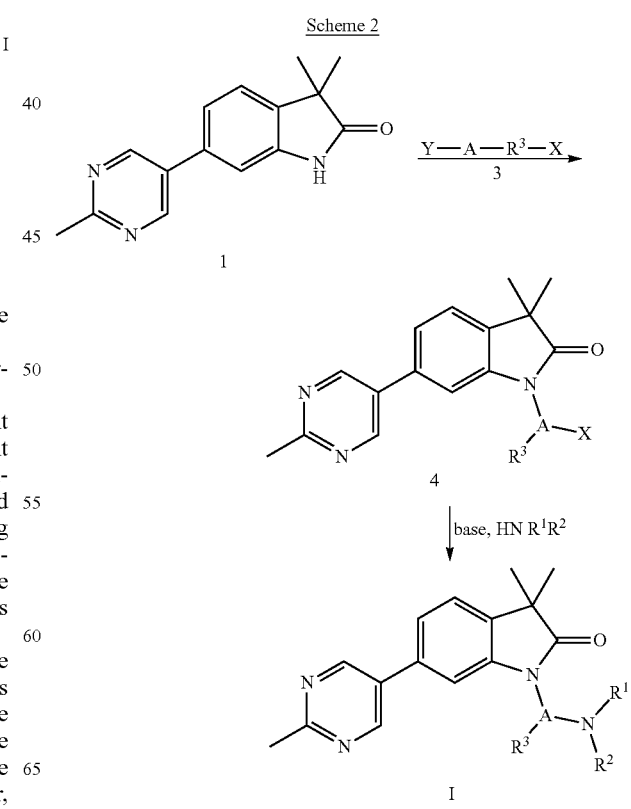

Compounds of formula 4 can be synthesized with compounds 1 (WO2014/202493 A1) and aryl-halogenides 3 (Y=Cl, Br, I) in the presence of copper(I)iodide, a ligand such as N,N'-dimethylethylendiamine and a base, e.g. potassium carbonate. Final compounds I can be prepared from compounds 4 (X=Cl, F) by aromatic substitution in a presence of a base, preferentially triethylamine or potassium carbonate.

EXPERIMENTAL PART

The following examples are provided for illustration of the invention. They should not be considered as limiting the scope of the invention, but merely as being representative thereof.

Abbreviations

Boc, t-butyloxycarbonyl;
DIPEA, diisopropylethylamine;
DMAP, dimethylaminopyridine;
DMF, dimethylformamide;
DMSO, dimethylsulfoxide;
EDCI, 1-ethyl-3-(3-dimethylaminopropyl)carbodiimid;
EtOAc, ethyl acetate;
HOBt, 1-hydroxybenzotriazole;
MeOH, methanol;
NMP, N-methyl-2-pyrrolidon;
PMB, p-methoxybenzyl;
TFA, trifluoroacetic acid;
THF, tetrahydrofuran.

General: Silica gel chromatography was either performed using cartridges packed with silica gel (ISOLUTE® Columns, TELOS™ Flash Columns) or silica-NH2 gel (TELOS™ Flash NH$_2$ Columns) on ISCO Combi Flash Companion or on glass columns on silica gel 60 (32-60 mesh, 60 Å). MS: Mass spectra (MS) were measured with ion spray positive or negative method on a Perkin-Elmer SCIEX API 300.

Example 1

3,3-Dimethyl-6-(2-methylpyrimidin-5-yl)-1-(6-morpholinopyrazin-2-yl)indolin-2-one

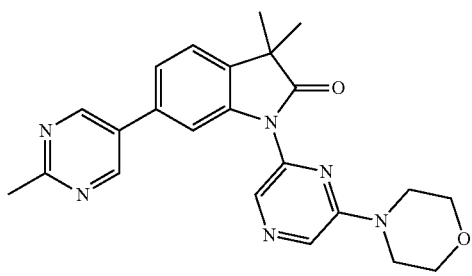 [SMILES: Cc1ncc(-c2ccc3c(c2)N(c2cncc(N4CCOCC4)n2)C(=O)C3(C)C)cn1]

In a pressure tube, argon was bubbled through a suspension of 3,3-dimethyl-6-(2-methylpyrimidin-5-yl)indolin-2-one (80 mg, 316 µmol, Eq: 1, WO2014/202493 A1), 4-(6-bromopyrazin-2-yl)morpholine (116 mg, 474 µmol, Eq: 1.5) and potassium carbonate (87.3 mg, 632 µmol, Eq: 2) in acetonitrile (1.26 ml) for 5 minutes. Copper (I) iodide (6.02 mg, 31.6 µmol, Eq: 0.1) and N,N'-dimethylethylenediamine (5.57 mg, 6.8 µl, 63.2 µmol, Eq: 0.2) were added, again flushed with argon, and the tube was sealed and the reaction mixture was heated to 120° C. overnight. The crude material was diluted with dichloromethane and concentrated in vacuo. The residue was purified by chromatography on silica gel to afford the desired product as a white solid (115 mg, 87%). MS (m/z)=417.2 [M+H]+.

Example 2

1-(6-Aminopyrazin-2-yl)-3,3-dimethyl-6-(2-methylpyrimidin-5-yl)indolin-2-one

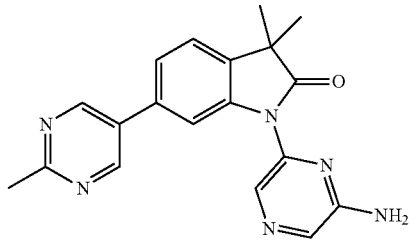 [SMILES: Cc1ncc(-c2ccc3c(c2)N(c2cncc(N)n2)C(=O)C3(C)C)cn1]

In a pressure tube, argon was bubbled through a suspension of 3,3-dimethyl-6-(2-methylpyrimidin-5-yl)indolin-2-one (80 mg, 316 µmol, Eq: 1, WO2014/202493 A1), 6-bromopyrazin-2-amine (82.4 mg, 474 µmol, Eq: 1.5) and potassium carbonate (87.3 mg, 632 Eq: 2) in acetonitrile (1.26 ml) for 5 minutes. Copper (I) iodide (12 mg, 63.2 µmol, Eq: 0.2) and N,N'-dimethylethylenediamine (11.1 mg, 13.6 µl, 126 µmol, Eq: 0.4) were added, again flushed with argon, the tube was sealed and the reaction mixture was heated to 120° C. overnight. The crude material was diluted with dichloromethane and concentrated in vacuo. The residue was purified by chromatography on silica gel to afford the desired product as a white solid (80 mg, 73%). MS (m/z)=347.2 [(M+H)$^+$].

Example 3

3,3-Dimethyl-6-(2-methylpyrimidin-5-yl)-1-(6-(2-oxopyrrolidin-1-yl)pyrazin-2-yl)indolin-2-one

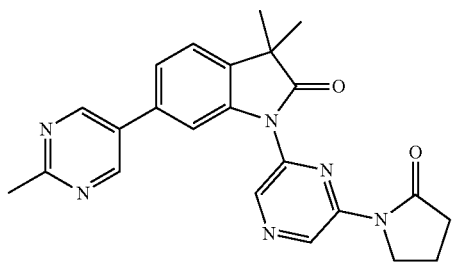 [SMILES: Cc1ncc(-c2ccc3c(c2)N(c2cncc(N4CCCC4=O)n2)C(=O)C3(C)C)cn1]

Example 3 was prepared from 3,3-dimethyl-6-(2-methylpyrimidin-5-yl)indolin-2-one (from WO2014/202493 A1)

with 1-(6-bromopyrazin-2-yl)pyrrolidin-2-one in analogy to example 2 to give the title compound (97%) as a light yellow solid.

MS (m/z)=415.2 [(M+H)$^+$].

Example 4

3,3-Dimethyl-6-(2-methylpyrimidin-5-yl)-1-(6-(pyrrolidin-1-yl)pyrazin-2-yl)indolin-2-one

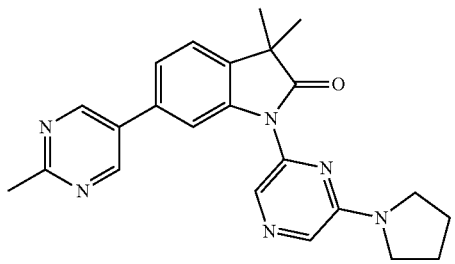 [SMILES: Cc1ncc(-c2ccc3c(c2)N(c2cncc(N4CCCC4)n2)C(=O)C3(C)C)cn1]

Example 4 was prepared from 3,3-dimethyl-6-(2-methylpyrimidin-5-yl)indolin-2-one (from WO2014/202493 A1) with 2-bromo-6-(pyrrolidin-1-yl)pyrazine in analogy to example 2 to give the title compound (92%) as a light red solid. MS (m/z)=401.2 [(M+H)$^+$].

Example 5

N-(6-(3,3-Dimethyl-6-(2-methylpyrimidin-5-yl)-2-oxoindolin-1-yl)pyrazin-2-yl)acetamide

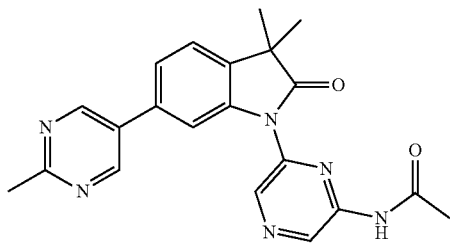 [SMILES: CC(=O)Nc1cncc(N2C(=O)C(C)(C)c3ccc(-c4cnc(C)nc4)cc32)n1]

1-(6-Aminopyrazin-2-yl)-3,3-dimethyl-6-(2-methylpyrimidin-5-yl)indolin-2-one (55 mg, 159 μmol, Eq: 1, Example 2) and acetic anhydride (32.4 mg, 30 μl, 318 μmol, Eq: 2) were combined with acetic acid (529 μl). The reaction mixture was heated to 80° C. and stirred for 2 h. The reaction mixture was poured into 50 mL of saturated sodium bicarbonate and extracted with dichloromethane (2×50 mL). The organic layers were combined and washed with saturated sodium bicarbonate and brine, dried over sodium sulfate then filtered and evaporated in vacuo. The residue was purified by chromatography on silica gel to afford the desired product as a white solid (53 mg, 85%). MS (m/z)= 389.1 [M+H]+

Example 6

1-(6-(4,4-Difluoropiperidin-1-yl)pyrazin-2-yl)-3,3-dimethyl-6-(2-methylpyrimidin-5-yl)indolin-2-one

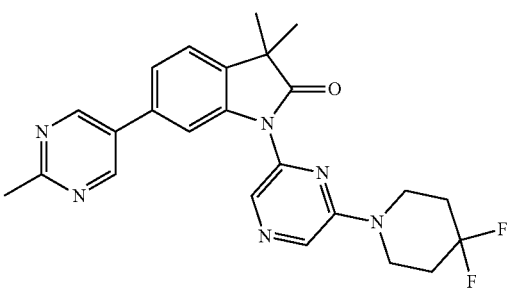 [SMILES: Cc1ncc(-c2ccc3c(c2)N(c2cncc(N4CCC(F)(F)CC4)n2)C(=O)C3(C)C)cn1]

a) 1-(6-Chloropyrazin-2-yl)-3,3-dimethyl-6-(2-methylpyrimidin-5-yl)indolin-2-one

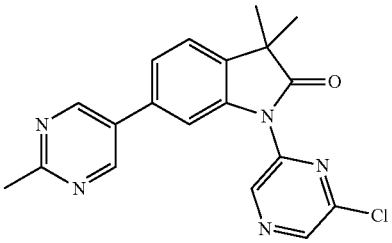 [SMILES: Cc1ncc(-c2ccc3c(c2)N(c2cncc(Cl)n2)C(=O)C3(C)C)cn1]

Example 6a was prepared from 3,3-dimethyl-6-(2-methylpyrimidin-5-yl)indolin-2-one (from WO2014/202493 A1) with 2-bromo-6-chloropyrazine in analogy to example 1 to give the title compound (58%) as a light yellow solid. MS (m/z)=366.2 [(M+H)$^+$].

b) 1-(6-(4,4-Difluoropiperidin-1-yl)pyrazin-2-yl)-3,3-dimethyl-6-(2-methylpyrimidin-5-yl)indolin-2-one

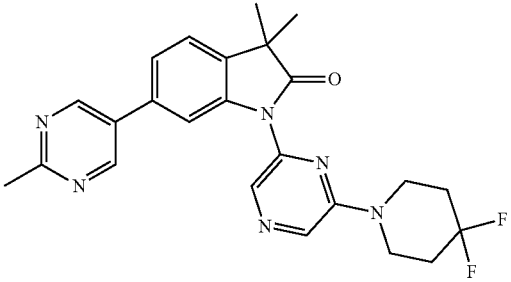 [SMILES: Cc1ncc(-c2ccc3c(c2)N(c2cncc(N4CCC(F)(F)CC4)n2)C(=O)C3(C)C)cn1]

1-(6-Chloropyrazin-2-yl)-3,3-dimethyl-6-(2-methylpyrimidin-5-yl)indolin-2-one (50 mg, 137 Eq: 1), triethylamine (27.7 mg, 38.1 μl, 273 μmol, Eq: 2) and 4,4-difluoropiperidine hydrochloride (25.8 mg, 164 μmol, Eq: 1.2) were combined with tetrahydrofuran (342 μl). The reaction mixture was heated to 100-150° C. for 3 days with regular addition of the amine and the base until no starting material was left. The crude material was concentrated in vacuo. The residue was purified by chromatography on silica gel, followed by preparative HPLC to afford the desired product as a white solid (29 mg, 47%). MS (m/z)=451.2 [M+H]+.

Example 7

1-(6-(Cyclopropylamino)pyrazin-2-yl)-3,3-dimethyl-6-(2-methylpyrimidin-5-yl)indolin-2-one

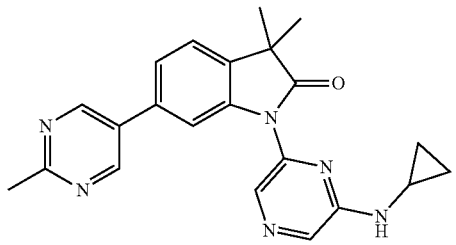 [SMILES: Cc1ncc(-c2ccc3c(c2)N(c2cncc(NC4CC4)n2)C(=O)C3(C)C)cn1]

1-(6-Chloropyrazin-2-yl)-3,3-dimethyl-6-(2-methylpyrimidin-5-yl)indolin-2-one (50 mg, 137 µmol, Eq: 1, Example 6a) and cyclopropylamine (546 mg, 674 µl, 9.57 mmol, Eq: 70) were combined. The reaction mixture was heated to 100° C. and stirred for 5 h.

The residue was purified by chromatography on silica gel, followed by trituration with diisopropylether to afford the desired product as a light yellow solid (30 mg, 56%). MS (m/z)=387.2 [M+H]+.

Example 8

1-[6-(2-Methoxyethylamino)pyrazin-2-yl]-3,3-dimethyl-6-(2-methylpyrimidin-5-yl)indol-2-one

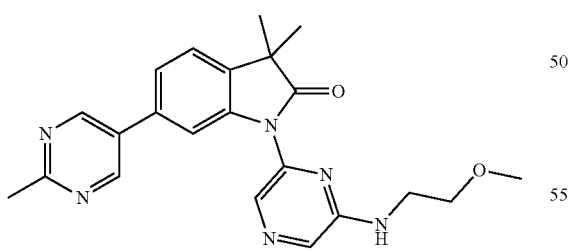

1-(6-Chloropyrazin-2-yl)-3,3-dimethyl-6-(2-methylpyrimidin-5-yl)indolin-2-one (50 mg, 137 µmol, Eq: 1, Example 6a) and 2-methoxyethanamine (616 mg, 716 µl, 8.2 mmol, Eq: 60) were heated for 24 h at 100° C.

The residue was purified by chromatography on silica gel to afford the desired product as a white foam (52 mg, 94%). MS (m/z)=405.2 [M+H]+.

Example 9

1-(6-(4-Hydroxypiperidin-1-yl)pyrazin-2-yl)-3,3-dimethyl-6-(2-methylpyrimidin-5-yl)indolin-2-one

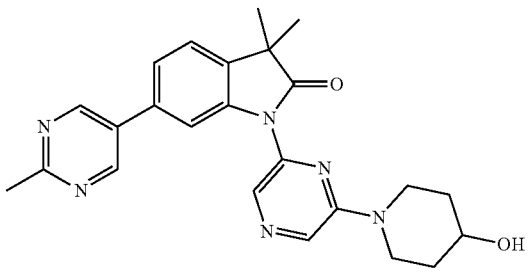 [SMILES: Cc1ncc(-c2ccc3c(c2)N(c2cncc(N4CCC(O)CC4)n2)C(=O)C3(C)C)cn1]

Example 9 was prepared from 1-(6-chloropyrazin-2-yl)-3,3-dimethyl-6-(2-methylpyrimidin-5-yl)indolin-2-one (Example 6a) with piperidin-4-ol in analogy to example 6b to give the title compound (88%) as a white solid. MS (m/z)=431.2 [(M+H)$^+$].

Example 10

1-(6-(1,1-Dioxidothiomorpholino)pyrazin-2-yl)-3,3-dimethyl-6-(2-methylpyrimidin-5-yl)indolin-2-one

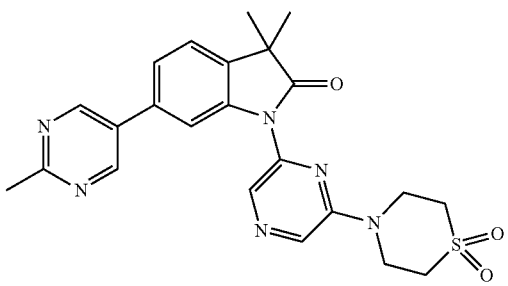 [SMILES: Cc1ncc(-c2ccc3c(c2)N(c2cncc(N4CCS(=O)(=O)CC4)n2)C(=O)C3(C)C)cn1]

Example 10 was prepared from 1-(6-chloropyrazin-2-yl)-3,3-dimethyl-6-(2-methylpyrimidin-5-yl)indolin-2-one (Example 6a) with thiomorpholine 1,1-dioxide in analogy to example 6b to give the title compound (77%) as a white solid. MS (m/z)=465.2 [(M+H)$^+$].

Example 11

1-(6-(4-Hydroxy-4-methylpiperidin-1-yl)pyrazin-2-yl)-3,3-dimethyl-6-(2-methylpyrimidin-5-yl)indolin-2-one

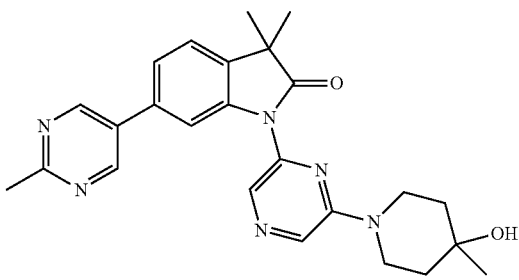 [SMILES: Cc1ncc(-c2ccc3c(c2)N(c2cncc(N4CCC(C)(O)CC4)n2)C(=O)C3(C)C)cn1]

1-(6-Chloropyrazin-2-yl)-3,3-dimethyl-6-(2-methylpyrimidin-5-yl)indolin-2-one (52 mg, 142 Eq: 1, Example 6a), 4-methylpiperidin-4-ol (24.6 mg, 213 µmol, Eq: 1.5) and potassium carbonate (39.3 mg, 284 µmol, Eq: 2) were combined with acetonitrile (711 µl). The reaction mixture was heated to 100° C. and stirred for 3 days until no starting material was left. The residue was purified by chromatography on silica gel to afford the desired product as a light yellow foam (63 mg, 99%). MS (m/z)=445.2 [M+H]+.

Example 12

1-(6-((2-Methoxyethyl)(methyl)amino)pyrazin-2-yl)-3,3-dimethyl-6-(2-methylpyrimidin-5-yl)indolin-2-one

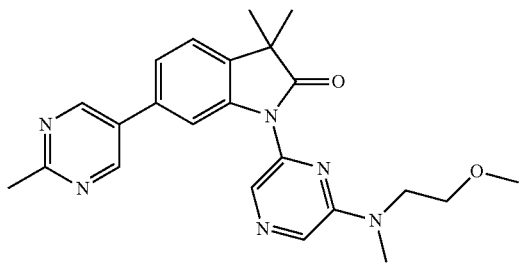

Example 12 was prepared from 1-(6-chloropyrazin-2-yl)-3,3-dimethyl-6-(2-methylpyrimidin-5-yl)indolin-2-one (Example 6a) with 2-methoxy-N-methylethanamine in analogy to example 11 to give the title compound (95%) as a light yellow solid. MS (m/z)=419.2 [(M+H)+].

Example 13

1-(6-((1R,5S)-3-Oxa-6-azabicyclo[3.1.1]heptan-6-yl)pyrazin-2-yl)-3,3-dimethyl-6-(2-methylpyrimidin-5-yl)indolin-2-one

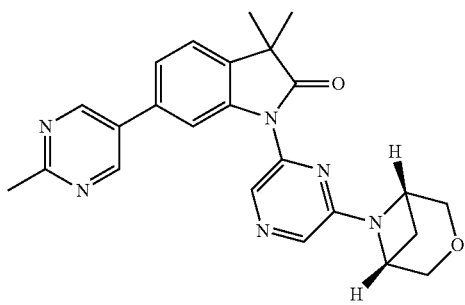 [SMILES: Cc1ncc(-c2ccc3c(c2)N(c2cncc(N4[C@@H]5COC[C@H]4C5)n2)C(=O)C3(C)C)cn1]

Example 13 was prepared from 1-(6-chloropyrazin-2-yl)-3,3-dimethyl-6-(2-methylpyrimidin-5-yl)indolin-2-one (Example 6a) with (1R,5S)-3-oxa-6-azabicyclo[3.1.1]heptane 2,2,2-trifluoroacetate in analogy to example 11 to give the title compound (91%) as a light yellow solid. MS (m/z)=429.2 [(M+H)+].

Example 14

1-(6-(6-Oxa-1-azaspiro[3.3]heptan-1-yl)pyrazin-2-yl)-3,3-dimethyl-6-(2-methylpyrimidin-5-yl)indolin-2-one

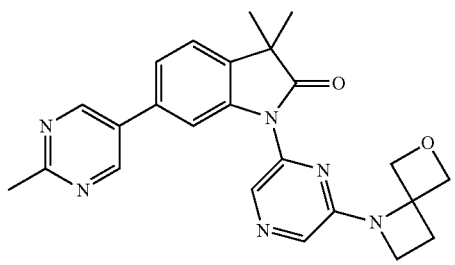 [SMILES: Cc1ncc(-c2ccc3c(c2)N(c2cncc(N4CCC45COC5)n2)C(=O)C3(C)C)cn1]

Example 14 was prepared from 1-(6-chloropyrazin-2-yl)-3,3-dimethyl-6-(2-methylpyrimidin-5-yl)indolin-2-one (Example 6a) with 6-oxa-1-azaspiro[3.3]heptan-1-ium oxalate in analogy to example 11 to give the title compound (17%) as a white solid. MS (m/z)=429.3 [(M+H)+].

Example 15

3-(6-(3,3-Dimethyl-6-(2-methylpyrimidin-5-yl)-2-oxoindolin-1-yl)pyrazin-2-yl)oxazolidin-2-one

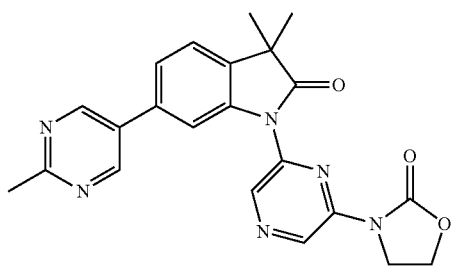 [SMILES: Cc1ncc(-c2ccc3c(c2)N(c2cncc(N4CCOC4=O)n2)C(=O)C3(C)C)cn1]

In a pressure tube, argon was bubbled through a suspension of 1-(6-chloropyrazin-2-yl)-3,3-dimethyl-6-(2-methylpyrimidin-5-yl)indolin-2-one (50 mg, 137 µmol, Eq: 1, Example 6a), oxazolidin-2-one (17.9 mg, 205 µmol, Eq: 1.5) and potassium carbonate (37.8 mg, 273 Eq: 2) in acetonitrile (911 µl) for 5 minutes. Copper (I) iodide (10.4 mg, 54.7 µmol, Eq: 0.4) and N,N'-dimethylethylenediamine (9.64 mg, 11.8 µl, 109 µmol, Eq: 0.8) were added, again flushed with argon, the tube was sealed and the reaction mixture was heated to 120° C. for 6.5 h. The residue was purified by chromatography on silica gel to afford the desired product as a light yellow solid (30 mg, 52%). MS (m/z)=417.2 [M+H]+.

Example 16

1-(6-((1R,5S)-6-Oxa-3-azabicyclo[3.1.1]heptan-3-yl)pyrazin-2-yl)-3,3-dimethyl-6-(2-methylpyrimidin-5-yl)indolin-2-one

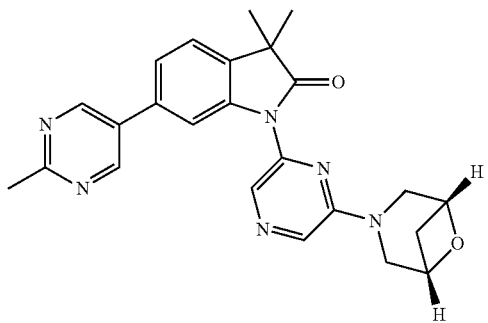 [SMILES: Cc1ncc(-c2ccc3c(c2)N(c2cncc(N4C[C@H]5C[C@@H](C4)O5)n2)C(=O)C3(C)C)cn1]

Example 16 was prepared from 1-(6-chloropyrazin-2-yl)-3,3-dimethyl-6-(2-methylpyrimidin-5-yl)indolin-2-one (Example 6a) with (1R,5S)-6-oxa-3-azabicyclo[3.1.1]heptan-3-ium oxalate in analogy to example 11 to give the title compound (92%) as a light yellow solid. MS (m/z)=429.3 [(M+H)$^+$].

Example 17

3,3-Dimethyl-6-(2-methylpyrimidin-5-yl)-1-(6-(oxetan-3-ylamino)pyrazin-2-yl)indolin-2-one

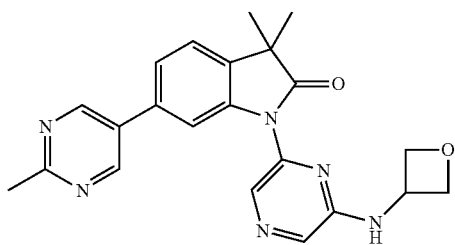 [SMILES: Cc1ncc(-c2ccc3c(c2)N(c2cncc(NC4COC4)n2)C(=O)C3(C)C)cn1]

Example 17 was prepared from 1-(6-chloropyrazin-2-yl)-3,3-dimethyl-6-(2-methylpyrimidin-5-yl)indolin-2-one (Example 6a) with oxetan-3-amine in analogy to example 8 to give the title compound (36%) as a light yellow solid. MS (m/z)=403.2 [(M+H)$^+$].

Example 18

3,3-Dimethyl-1-(5-methyl-6-morpholinopyrazin-2-yl)-6-(2-methylpyrimidin-5-yl)indolin-2-one

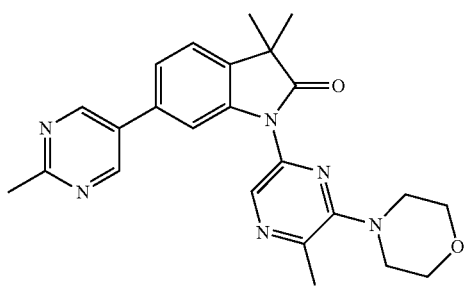 [SMILES: Cc1ncc(-c2ccc3c(c2)N(c2cnc(C)c(N4CCOCC4)n2)C(=O)C3(C)C)cn1]

a) 4-(6-Chloro-3-methylpyrazin-2-yl)morpholine

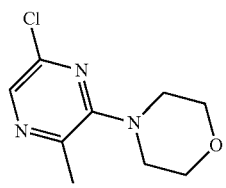

3,5-Dichloro-2-methylpyrazine (100 mg, 613 µmol, Eq: 1), cesium fluoride (280 mg, 1.84 mmol, Eq: 3) and morpholine (53.4 mg, 52.9 µl, 613 µmol, Eq: 1) were combined with dimethyl sulfoxide (2.04 ml) and stirred at room temperature overnight. The reaction mixture was poured into 20 mL of water and extracted with ethyl acetate (2×25 mL). The organic layers were washed with water, dried over sodium sulfate then filtered and evaporated in vacuo. The residue was purified by chromatography on silica gel to afford the desired product as a light yellow viscous oil (78 mg, 59%). MS (m/z)=214.1 [M+H]+.

b) 3,3-Dimethyl-1-(5-methyl-6-morpholinopyrazin-2-yl)-6-(2-methylpyrimidin-5-yl)indolin-2-one

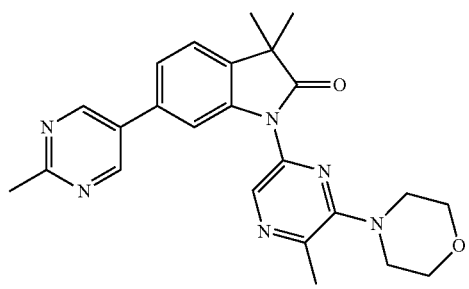 [SMILES: Cc1ncc(-c2ccc3c(c2)N(c2cnc(C)c(N4CCOCC4)n2)C(=O)C3(C)C)cn1]

In a pressure tube, argon was bubbled through a suspension of 3,3-dimethyl-6-(2-methylpyrimidin-5-yl)indolin-2-one (80 mg, 316 µmol, Eq: 1, WO2014/202493 A1), 4-(6-chloro-3-methylpyrazin-2-yl)morpholine (74.2 mg, 347 µmol, Eq: 1.1) and cesium carbonate (134 mg, 411 µmol, Eq: 1.3) in dioxane (1.58 ml) for 5 minutes. Xantphos (36.5 mg, 63.2 µmol, Eq: 0.2) and tris(dibenzylideneacetone)dipalladium (0) (57.8 mg, 63.2 µmol, Eq: 0.2) were added, again flushed with argon, the tube was sealed and the reaction mixture was heated to 120° C. overnight.

The residue was purified by chromatography on silica gel to afford the desired product as a light red foam (90 mg, 66%). MS (m/z)=431.2 [M+H]+.

Example 19

1-(6-((2-Methoxyethyl)amino)-5-methylpyrazin-2-yl)-3,3-dimethyl-6-(2-methylpyrimidin-5-yl)indolin-2-one

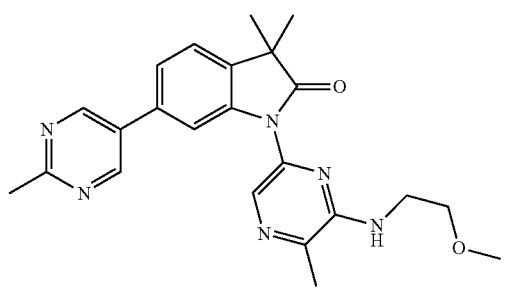

a) 6-Chloro-N-(2-methoxyethyl)-3-methylpyrazin-2-amine

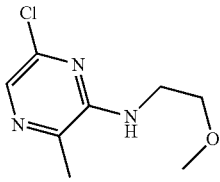

Example 19a was prepared from 3,5-dichloro-2-methylpyrazine with 2-methoxyethanamine in analogy to example 18a to give the title compound (53%) as a white solid.
MS (m/z)=202.1 [(M+H)$^+$].

b) 1-(6-((2-Methoxyethyl)amino)-5-methylpyrazin-2-yl)-3,3-dimethyl-6-(2-methylpyrimidin-5-yl)indolin-2-one6-chloro-N-(2-methoxyethyl)-3-methylpyrazin-2-amine

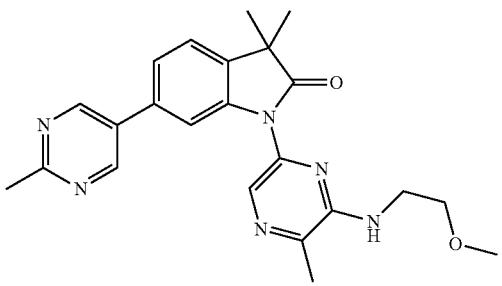

Example 19b was prepared from 3,3-dimethyl-6-(2-methylpyrimidin-5-yl)indolin-2-one (WO2014/202493 A1) with 6-chloro-N-(2-methoxyethyl)-3-methylpyrazin-2-amine in analogy to example 18b to give the title compound (65%) as a light yellow foam.
MS (m/z)=417.4 [(M−H)$^+$].

Example 20

3-(6-(3,3-Dimethyl-6-(2-methylpyrimidin-5-yl)-2-oxoindolin-1-yl)-3-methylpyrazin-2-yl)oxazolidin-2-one

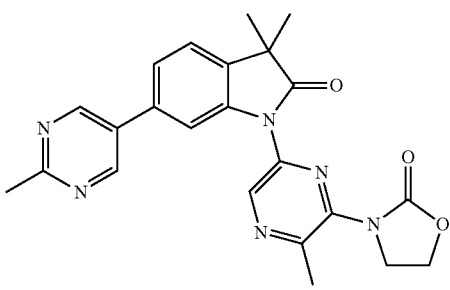 [SMILES: Cc1ncc(-c2ccc3c(c2)N(c2cnc(C)c(N4CCOC4=O)n2)C(=O)C3(C)C)cn1]

a) 3-(6-Chloro-3-methylpyrazin-2-yl)oxazolidin-2-one

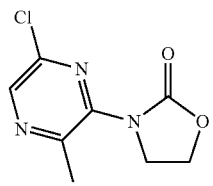

Example 20a was prepared from 3,5-dichloro-2-methylpyrazine with oxazolidin-2-one in analogy to example 18a to give the title compound (77%) as a colorless viscous oil.
MS (m/z)=214.1 [(M+H)$^+$].

b) 3-(6-(3,3-Dimethyl-6-(2-methylpyrimidin-5-yl)-2-oxoindolin-1-yl)-3-methylpyrazin-2-yl)oxazolidin-2-one

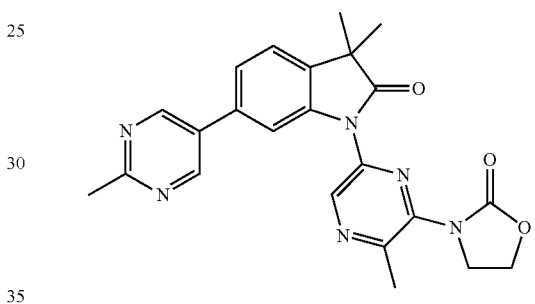

Example 20b was prepared from 3,3-dimethyl-6-(2-methylpyrimidin-5-yl)indolin-2-one (WO2014/202493 A1) with 3-(6-chloro-3-methylpyrazin-2-yl)oxazolidin-2-one in analogy to example 18b to give the title compound (79%) as a light brown foam.
MS (m/z)=431.3 [(M+H)$^+$].

Example 21

(R)-3-(6-(3,3-Dimethyl-6-(2-methylpyrimidin-5-yl)-2-oxoindolin-1-yl)pyrazin-2-yl)-4-isopropyloxazolidin-2-one

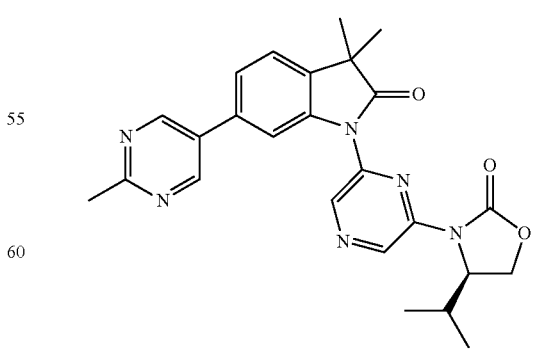

Example 21 was prepared from 1-(6-chloropyrazin-2-yl)-3,3-dimethyl-6-(2-methylpyrimidin-5-yl)indolin-2-one (Example 6a) with (R)-(+)-4-isopropyloxazolidin-2-one in analogy to example 15 to give the title compound (24%) as a light yellow amorphous solid.

MS (m/z)=459.4 [(M+H)+].

Example 22

(S)-3-(6-(3,3-Dimethyl-6-(2-methylpyrimidin-5-yl)-2-oxoindolin-1-yl)pyrazin-2-yl)-4-isopropyloxazolidin-2-one

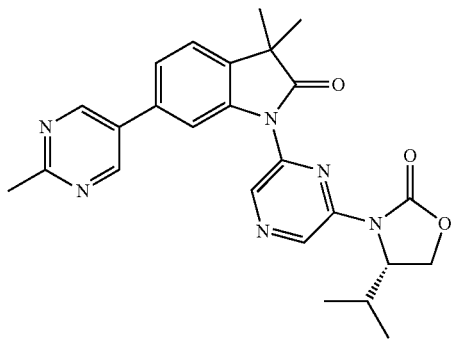 [SMILES: Cc1ncc(-c2ccc3c(c2)N(c2cncc(N4C(=O)OC[C@@H]4C(C)C)n2)C(=O)C3(C)C)cn1]

Example 22 was prepared from 1-(6-chloropyrazin-2-yl)-3,3-dimethyl-6-(2-methylpyrimidin-5-yl)indolin-2-one (Example 6a) with (S)-(−)-4-isopropyloxazolidin-2-one in analogy to example 15 to give the title compound (24%) as a light yellow amorphous solid.

MS (m/z)=459.4 [(M+H)+].

Example 23

3,3-Dimethyl-6-(2-methylpyrimidin-5-yl)-1-(2-morpholinopyrimidin-4-yl)indolin-2-one

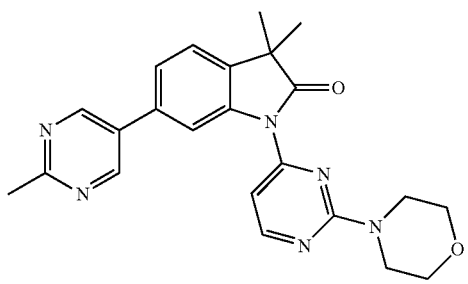 [SMILES: Cc1ncc(-c2ccc3c(c2)N(c2ccnc(N4CCOCC4)n2)C(=O)C3(C)C)cn1]

Example 23 was prepared from 3,3-dimethyl-6-(2-methylpyrimidin-5-yl)indolin-2-one (WO2014/202493 A1) with 4-(4-bromopyrimidin-2-yl)morpholine in analogy to example 2 to give the title compound (99%) as a white foam. MS (m/z)=417.2 [(M+H)+].

Example 24

3,3-Dimethyl-6-(2-methylpyrimidin-5-yl)-1-(4-morpholinopyrimidin-2-yl)indolin-2-one

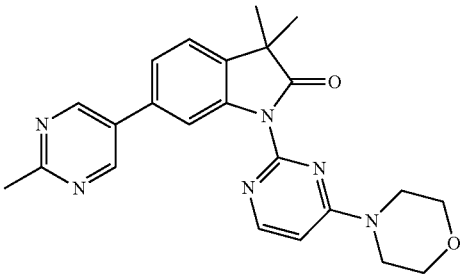 [SMILES: Cc1ncc(-c2ccc3c(c2)N(c2nccc(N4CCOCC4)n2)C(=O)C3(C)C)cn1]

Example 24 was prepared from 3,3-dimethyl-6-(2-methylpyrimidin-5-yl)indolin-2-one (WO2014/202493 A1) with 4-(2-bromopyrimidin-4-yl)morpholine in analogy to example 2 to give the title compound (70%) as a colorless solid. MS (m/z)=417.2 [(M+H)+].

Example 25

1-(5-Aminopyridin-3-yl)-3,3-dimethyl-6-(2-methylpyrimidin-5-yl)indolin-2-one

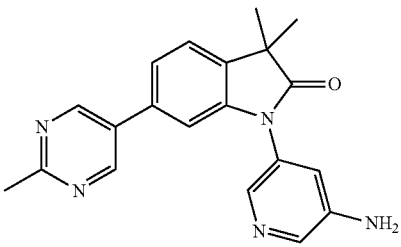 [SMILES: Cc1ncc(-c2ccc3c(c2)N(c2cncc(N)c2)C(=O)C3(C)C)cn1]

Example 25 was prepared from 3,3-dimethyl-6-(2-methylpyrimidin-5-yl)indolin-2-one (WO2014/202493 A1) with 5-bromopyridin-3-amine in analogy to example 2 to give the title compound (100%) as a light brown solid. MS (m/z)= 346.1 [(M+H)+].

Example 26

3,3-Dimethyl-6-(2-methylpyrimidin-5-yl)-1-(5-morpholinopyridin-3-yl)indolin-2-one

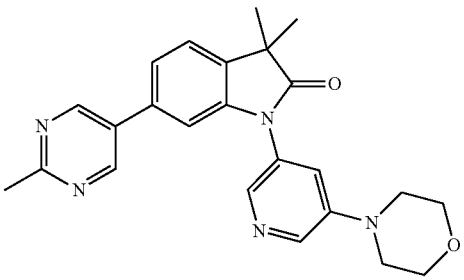 [SMILES: Cc1ncc(-c2ccc3c(c2)N(c2cncc(N4CCOCC4)c2)C(=O)C3(C)C)cn1]

Example 26 was prepared from 3,3-dimethyl-6-(2-methylpyrimidin-5-yl)indolin-2-one (WO2014/202493 A1) with 4-(5-bromopyridin-3-yl)morpholine in analogy to example 2 to give the title compound (46%) as a white solid. MS (m/z)=416.2 [(M+H)+].

Example 27

3,3-Dimethyl-6-(2-methylpyrimidin-5-yl)-1-(6-morpholinopyridin-2-yl)indolin-2-one

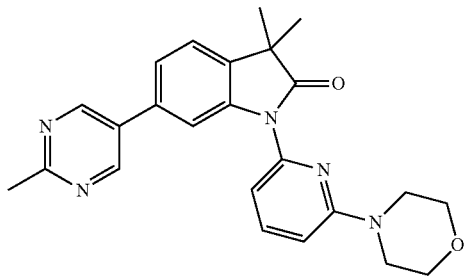 [SMILES: Cc1ncc(-c2ccc3c(c2)N(c2cccc(N4CCOCC4)n2)C(=O)C3(C)C)cn1]

Example 27 was prepared from 3,3-dimethyl-6-(2-methylpyrimidin-5-yl)indolin-2-one (WO2014/202493 A1) with 4-(6-bromopyridin-2-yl)morpholine in analogy to example 2 to give the title compound (72%) as a white solid. MS (m/z)=416.2 [(M+H)+].

Example 28

3-(6-(3,3-Dimethyl-6-(2-methylpyrimidin-5-yl)-2-oxoindolin-1-yl)pyridin-2-yl)oxazolidin-2-one

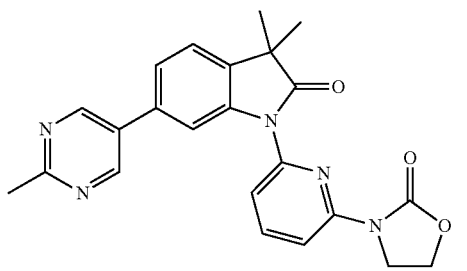 [SMILES: Cc1ncc(-c2ccc3c(c2)N(c2cccc(N4CCOC4=O)n2)C(=O)C3(C)C)cn1]

a) 1-(6-Chloropyridin-2-yl)-3,3-dimethyl-6-(2-methylpyrimidin-5-yl)indolin-2-one

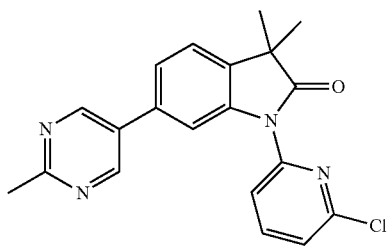 [SMILES: Cc1ncc(-c2ccc3c(c2)N(c2cccc(Cl)n2)C(=O)C3(C)C)cn1]

Example 28a was prepared from 3,3-dimethyl-6-(2-methylpyrimidin-5-yl)indolin-2-one (WO2014/202493 A1) with 2-bromo-6-chloropyridine in analogy to example 2 to give the title compound (63%) as a yellow solid. MS (m/z)=365.2 [(M+H)+].

b) 3-(6-(3,3-Dimethyl-6-(2-methylpyrimidin-5-yl)-2-oxoindolin-1-yl)pyridin-2-yl)oxazolidin-2-one

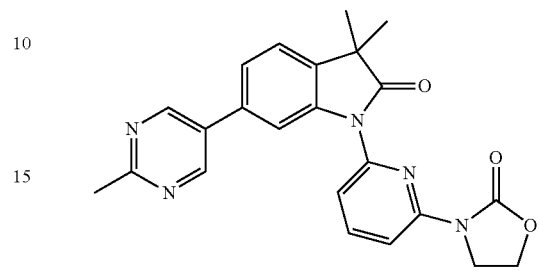

Example 28b was prepared from 1-(6-chloropyridin-2-yl)-3,3-dimethyl-6-(2-methylpyrimidin-5-yl)indolin-2-one with oxazolidin-2-one in analogy to example 15 to give the title compound (42%) as a white solid. MS (m/z)=416.3 [(M+H)+].

Example 29

1-(6-Amino-5-methylpyridin-2-yl)-3,3-dimethyl-6-(2-methylpyrimidin-5-yl)indolin-2-one

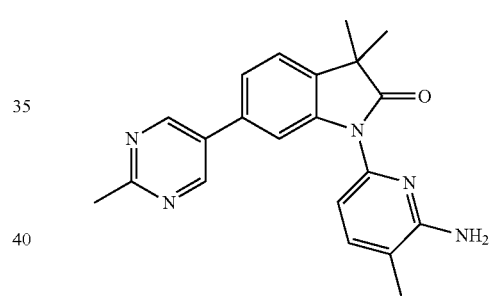

Example 29 was prepared from 3,3-dimethyl-6-(2-methylpyrimidin-5-yl)indolin-2-one (WO2014/202493 A1) with 6-bromo-3-methylpyridin-2-amine in analogy to example 2 to give the title compound (89%) as a light yellow solid. MS (m/z)=360.2 [(M+H)+].

Example 30

N-(6-(3,3-Dimethyl-6-(2-methylpyrimidin-5-yl)-2-oxoindolin-1-yl)-3-methylpyridin-2-yl)acetamide

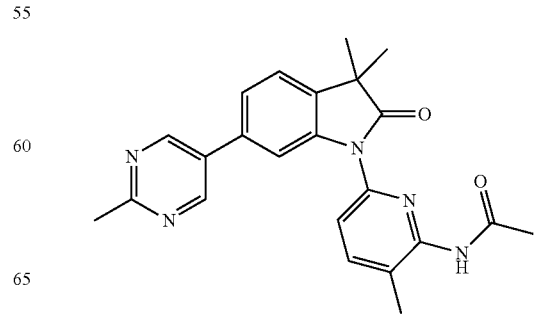

1-(6-Amino-5-methylpyridin-2-yl)-3,3-dimethyl-6-(2-methylpyrimidin-5-yl)indolin-2-one (72 mg, 200 µmol, Eq: 1, Example 29) was diluted with acetic acid (668 µl). Acetic anhydride (40.9 mg, 37.8 µl, 401 µmol, Eq: 2) was then added. The reaction mixture was stirred for 2 h at 80° C. The reaction mixture was poured into saturated sodium bicarbonate and extracted with dichloromethane (2×). The organic phases were combined and washed brine, dried over sodium sulfate then filtered and evaporated in vacuo to afford the desired product as a light yellow solid (82 mg, 100%). MS (m/z)=402.3 [(M+H)$^+$].

Example 31

3,3-Dimethyl-1-(5-methyl-6-morpholinopyridin-2-yl)-6-(2-methylpyrimidin-5-yl)indolin-2-one

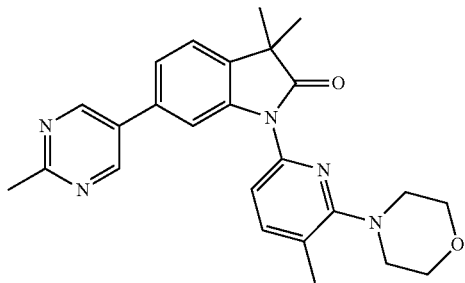 [SMILES: Cc1ncc(-c2ccc3c(c2)N(c2ccc(C)c(N4CCOCC4)n2)C(=O)C3(C)C)cn1]

a) 1-(6-Fluoro-5-methylpyridin-2-yl)-3,3-dimethyl-6-(2-methylpyrimidin-5-yl)indolin-2-one

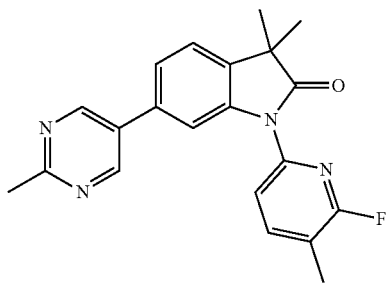 [SMILES: Cc1ncc(-c2ccc3c(c2)N(c2ccc(C)c(F)n2)C(=O)C3(C)C)cn1]

Example 31a was prepared from 3,3-dimethyl-6-(2-methylpyrimidin-5-yl)indolin-2-one (WO2014/202493 A1) with 6-bromo-2-fluoro-3-methylpyridine in analogy to example 2 to give the title compound (75%) as a white solid. MS (m/z)=363.2 [(M+H)$^+$].

b) 3,3-Dimethyl-1-(5-methyl-6-morpholinopyridin-2-yl)-6-(2-methylpyrimidin-5-yl)indolin-2-one

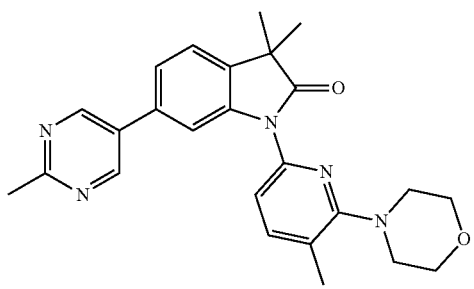 [SMILES: Cc1ncc(-c2ccc3c(c2)N(c2ccc(C)c(N4CCOCC4)n2)C(=O)C3(C)C)cn1]

1-(6-Fluoro-5-methylpyridin-2-yl)-3,3-dimethyl-6-(2-methylpyrimidin-5-yl)indolin-2-one (53.8 mg, 148 µmol, Eq: 1) and morpholine (776 mg, 779 µl, 8.91 mmol, Eq: 60) were heated for 2 days at 110° C.

The residue was purified by chromatography on silica gel to afford the desired product as a light yellow foam (55 mg, 86%). MS (m/z)=430.3 [M+H]+.

Example 32

3-(6-(3,3-Dimethyl-6-(2-methylpyrimidin-5-yl)-2-oxoindolin-1-yl)-3-methylpyridin-2-yl)oxazolidin-2-one

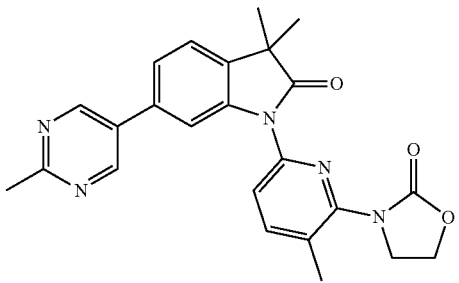 [SMILES: Cc1ncc(-c2ccc3c(c2)N(c2ccc(C)c(N4CCOC4=O)n2)C(=O)C3(C)C)cn1]

1-(6-Fluoro-5-methylpyridin-2-yl)-3,3-dimethyl-6-(2-methylpyrimidin-5-yl)indolin-2-one (40 mg, 110 µmol, Eq: 1, Example 31a) was dissolved in dimethylsulfoxide (368 µl). Cesium fluoride (50.3 mg, 331 µmol, Eq: 3) and oxazolidin-2-one (12.5 mg, 143 mol, Eq: 1.3) were added. The reaction mixture was stirred for 24 h at 100° C. The reaction mixture was poured into water and extracted with ethyl acetate (2×). The organic phases were combined and washed brine, dried over sodium sulfate then filtered and evaporated in vacuo.

The residue was purified by chromatography on silica gel to afford the desired product as an off-white solid (14 mg, 29%). MS (m/z)=430.3 [(M+H)$^+$].

Example 33

1-(1H-Indol-4-yl)-3,3-dimethyl-6-(2-methylpyrimidin-5-yl)indolin-2-one

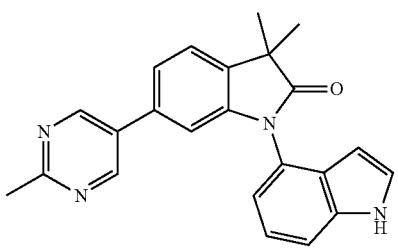 [SMILES: Cc1ncc(-c2ccc3c(c2)N(c2cccc4[nH]ccc24)C(=O)C3(C)C)cn1]

Example 33 was prepared from 3,3-dimethyl-6-(2-methylpyrimidin-5-yl)indolin-2-one (WO2014/202493 A1) with 4-bromo-1H-indole in analogy to example 2 to give the title compound (44%) as a white solid. MS (m/z)=369.2 [(M+H)$^+$].

Example 34

3,3-Dimethyl-6-(2-methylpyrimidin-5-yl)-1-(1H-pyrrolo[2,3-c]pyridin-4-yl)indolin-2-one

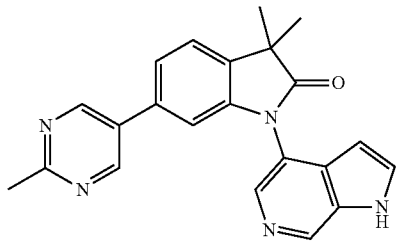 [SMILES: Cc1ncc(-c2ccc3c(c2)N(c2cncc4[nH]ccc24)C(=O)C3(C)C)cn1]

Example 34 was prepared from 3,3-dimethyl-6-(2-methylpyrimidin-5-yl)indolin-2-one (WO2014/202493 A1) with 4-bromo-1H-pyrrolo[2,3-c]pyridine in analogy to example 2 to give the title compound (17%) as a white solid. MS (m/z)=370.2 [(M+H)+].

Example 35

5-(3,3-Dimethyl-6-(2-methylpyrimidin-5-yl)-2-oxoindolin-1-yl)-1-methyl-1H-imidazo[4,5-b]pyrazin-2(3H)-one

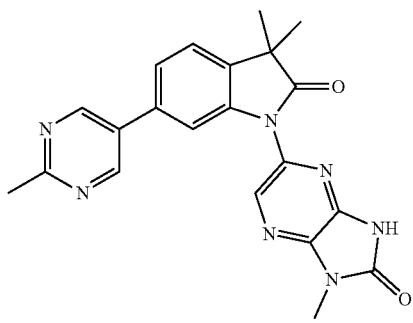 [SMILES: Cc1ncc(-c2ccc3c(c2)N(c2cnc4c(n2)[nH]c(=O)n4C)C(=O)C3(C)C)cn1]

a) 1-(6-Amino-5-(methylamino)pyrazin-2-yl)-3,3-dimethyl-6-(2-methylpyrimidin-5-yl)indolin-2-one

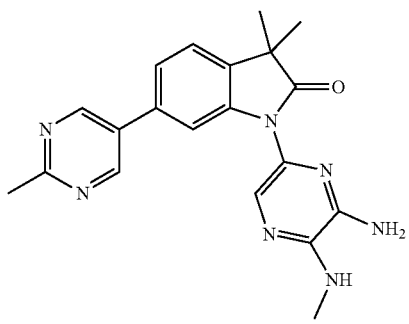 [SMILES: CNc1ncc(N2C(=O)C(C)(C)c3ccc(-c4cnc(C)nc4)cc32)nc1N]

Example 35a was prepared from 3,3-dimethyl-6-(2-methylpyrimidin-5-yl)indolin-2-one (WO2014/202493 A1) with 5-bromo-N2-methylpyrazine-2,3-diamine in analogy to example 2 to give the title compound (52%) as a brown solid. MS (m/z)=376.2 [(M+H)+].

b) 5-(3,3-Dimethyl-6-(2-methylpyrimidin-5-yl)-2-oxoindolin-1-yl)-1-methyl-1H-imidazo[4,5-b]pyrazin-2(3H)-one

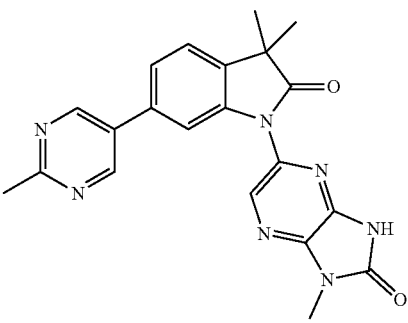 [SMILES: Cc1ncc(-c2ccc3c(c2)N(c2cnc4c(n2)[nH]c(=O)n4C)C(=O)C3(C)C)cn1]

1-(6-Amino-5-(methylamino)pyrazin-2-yl)-3,3-dimethyl-6-(2-methylpyrimidin-5-yl)indolin-2-one (60 mg, 160 µmol, Eq: 1) and 1,1'-carbonyldiimidazole (64.8 mg, 400 µmol, Eq: 2.5) were combined with tetrahydrofuran (864 µl). The reaction mixture was heated to 50° C. and stirred overnight. The residue was purified by chromatography on silica gel and finally triturated with ethyl acetate to afford the desired product as a light brown solid (19 mg, 29%). MS (m/z)= 402.2 [M+H]+.

Example 36

5-(3,3-Dimethyl-6-(2-methylpyrimidin-5-yl)-2-oxoindolin-1-yl)-1H-imidazo[4,5-b]pyrazin-2(3H)-one

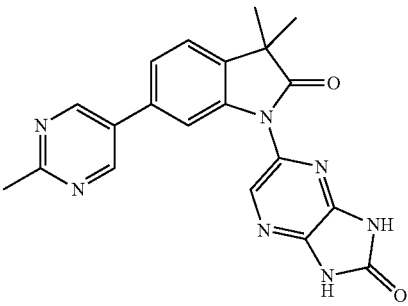 [SMILES: Cc1ncc(-c2ccc3c(c2)N(c2cnc4[nH]c(=O)[nH]c4n2)C(=O)C3(C)C)cn1]

a) 1-(5,6-Diaminopyrazin-2-yl)-3,3-dimethyl-6-(2-methylpyrimidin-5-yl)indolin-2-one

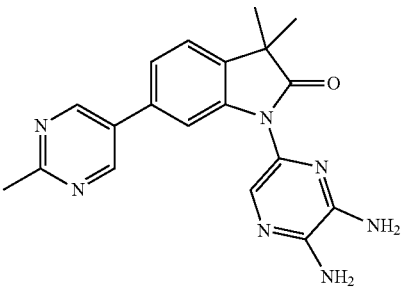 [SMILES: Cc1ncc(-c2ccc3c(c2)N(c2cnc(N)c(N)n2)C(=O)C3(C)C)cn1]

Example 36a was prepared from 3,3-dimethyl-6-(2-methylpyrimidin-5-yl)indolin-2-one (WO2014/202493 A1) with 5-bromopyrazine-2,3-diamine in analogy to example 2 to give the title compound (94%) as a light yellow solid. MS (m/z)=362.1 [(M+H)⁺].

b) 5-(3,3-Dimethyl-6-(2-methylpyrimidin-5-yl)-2-oxoindolin-1-yl)-1H-imidazo[4,5-b]pyrazin-2(3H)-one

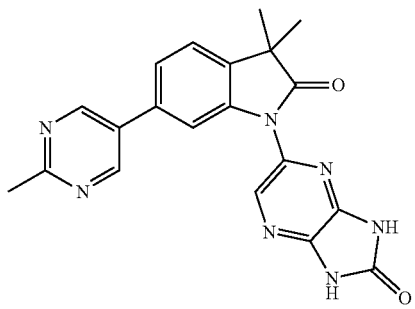 [SMILES: Cc1ncc(-c2ccc3c(c2)N(c2cnc4[nH]c(=O)[nH]c4n2)C(=O)C3(C)C)cn1]

Example 36b was prepared from 1-(5,6-diaminopyrazin-2-yl)-3,3-dimethyl-6-(2-methylpyrimidin-5-yl)indolin-2-one in analogy to example 35b to give the title compound (62%) as a light yellow crystalline solid. MS (m/z)=388.2 [(M+H)⁺].

Example 37

6-(3,3-Dimethyl-6-(2-methylpyrimidin-5-yl)-2-oxoindolin-1-yl)-3,3-dimethyl-1H-pyrrolo[2,3-b]pyridin-2(3H)-one

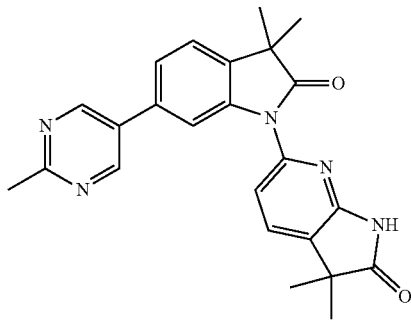 [SMILES: Cc1ncc(-c2ccc3c(c2)N(c2ccc4c(n2)NC(=O)C4(C)C)C(=O)C3(C)C)cn1]

a) 6-Chloro-1-(4-methoxybenzyl)-3,3-dimethyl-1H-pyrrolo[2,3-b]pyridin-2(3H)-one

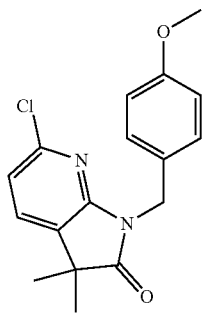 [SMILES: COc1ccc(CN2C(=O)C(C)(C)c3ccc(Cl)nc32)cc1]

6-Chloro-3,3-dimethyl-1H-pyrrolo[2,3-b]pyridin-2(3H)-one (300 mg, 1.53 mmol, Eq: 1, PCT Int. Appl., 2014040969) was dissolved in dimethylformamide (10.2 ml). Cesium carbonate (994 mg, 3.05 mmol, Eq: 2) and 1-(chloromethyl)-4-methoxybenzene (263 mg, 229 µl, 1.68 mmol, Eq: 1.1) were added. The reaction mixture was stirred at 80° C. for 5 h. The reaction mixture was poured into 50 mL of water and extracted with ethyl acetate (2×). The combined organic layers were washed with brine, dried over sodium sulfate then filtered and evaporated in vacuo to afford the desired product as a light yellow solid (473 mg, 97%). MS (m/z)=317.1 [M+H]+.

b) 6-(3,3-Dimethyl-6-(2-methylpyrimidin-5-yl)-2-oxoindolin-1-yl)-1-(4-methoxybenzyl)-3,3-dimethyl-1H-pyrrolo[2,3-b]pyridin-2(3H)-one

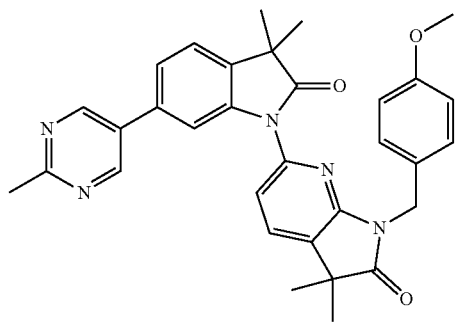

3,3-Dimethyl-6-(2-methylpyrimidin-5-yl)indolin-2-one (80 mg, 316 µmol, Eq: 1, WO2014/202493 A1) was dissolved in dry and degassed dioxane (1.58 ml) under argon atmosphere. Then 6-chloro-1-(4-methoxybenzyl)-3,3-dimethyl-1H-pyrrolo[2,3-b]pyridin-2(3H)-one (150 mg, 474 µmol, Eq: 1.5) and cesium carbonate (134 mg, 411 µmol, Eq: 1.3), followed by tris(dibenzylideneacetone)dipalladium (0) (57.8 mg, 63.2 µmol, Eq: 0.2) and xantphos (36.5 mg, 63.2 µmol, Eq: 0.2) were added and the tube was flushed with Argon. The reaction mixture was stirred for 24 h at 120° C.

The residue was purified by chromatography on silica gel to afford the desired product a light yellow solid (158 mg, 94%). MS (m/z)=534.3 [M+H]+.

c) 6-(3,3-Dimethyl-6-(2-methylpyrimidin-5-yl)-2-oxoindolin-1-yl)-3,3-dimethyl-1H-pyrrolo[2,3-b]pyridin-2(3H)-one

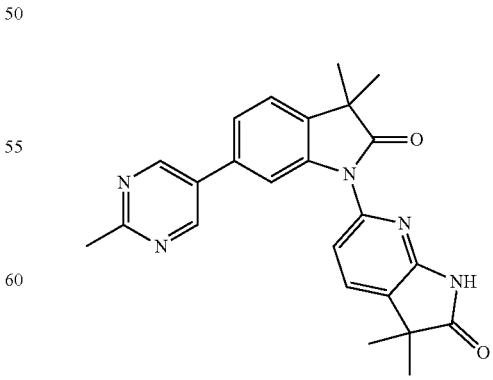

6-(3,3-Dimethyl-6-(2-methylpyrimidin-5-yl)-2-oxoindolin-1-yl)-1-(4-methoxybenzyl)-3,3-dimethyl-1H-pyrrolo[2,3-b]pyridin-2(3H)-one (158.9 mg, 298 µmol, Eq: 1) and trifluoroacetic acid (1.65 ml) were heated for few days at 110° C. until no starting material was left. The reaction mixture was evaporated in vacuo.

The residue was purified by chromatography on silica gel to afford the desired product as an off-white solid (42 mg, 34%). MS (m/z)=414.3 [M+H]+.

Example 38

7-(3,3-Dimethyl-6-(2-methylpyrimidin-5-yl)-2-oxoindolin-1-yl)-1H-pyrido[2,3-b][1,4]oxazin-2(3H)-one

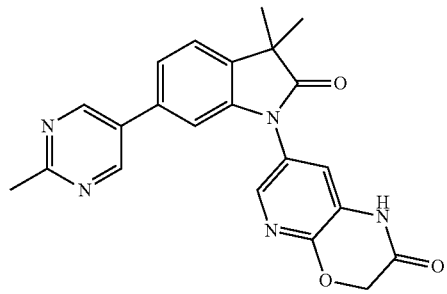 [SMILES: Cc1ncc(-c2ccc3c(c2)N(c2cnc4c(c2)NC(=O)CO4)C(=O)C3(C)C)cn1]

Example 38 was prepared from 3,3-dimethyl-6-(2-methylpyrimidin-5-yl)indolin-2-one (WO2014/202493 A1) with 7-bromo-1H-pyrido[2,3-b][1,4]oxazin-2(3H)-one in analogy to example 2 to give the title compound (88%) as a brown solid. MS (m/z)=402.2 [(M+H)+].

Example 39

6-(3,3-Dimethyl-6-(2-methylpyrimidin-5-yl)-2-oxoindolin-1-yl)-1,3,3-trimethyl-1H-pyrrolo[2,3-b]pyridin-2(3H)-one

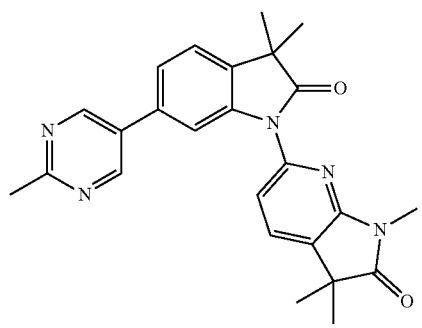

Example 39 was prepared from 3,3-dimethyl-6-(2-methylpyrimidin-5-yl)indolin-2-one (WO2014/202493 A1) with 6-chloro-1,3,3-trimethyl-1H-pyrrolo[2,3-b]pyridin-2(3H)-one (PCT Int. Appl., 2014040969) in analogy to example 37b to give the title compound (64%) as a brown solid. MS (m/z)=428.3 [(M+H)+].

Example 40

1-Cyclopropyl-6-(3,3-dimethyl-6-(2-methylpyrimidin-5-yl)-2-oxoindolin-1-yl)-3,3-dimethyl-1H-pyrrolo[3,2-c]pyridin-2(3H)-one

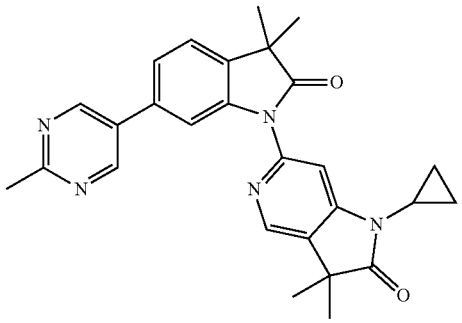 [SMILES: Cc1ncc(-c2ccc3c(c2)N(c2cc4c(cn2)C(C)(C)C(=O)N4C2CC2)C(=O)C3(C)C)cn1]

Example 40 was prepared from 3,3-dimethyl-6-(2-methylpyrimidin-5-yl)indolin-2-one (WO2014/202493 A1) with 6-chloro-1-cyclopropyl-3,3-dimethyl-1H-pyrrolo[3,2-c]pyridin-2(3H)-one (PCT Int. Appl., 2014040969) in analogy to example 37b to give the title compound (51%) as a white solid. MS (m/z)=454.4 [(M+H)+].

Example 41

1',3,3,3',3'-Pentamethyl-6-(2-methylpyrimidin-5-yl)-[1,6'-biindoline]-2,2'-dione

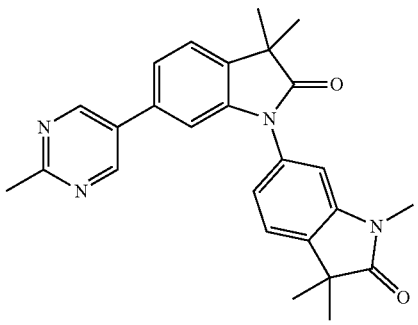

a) 6-bromo-1,3,3-trimethylindolin-2-one

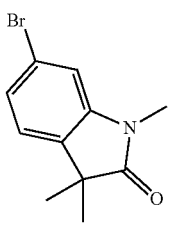

Sodium hydride (4.53 g, 94.3 mmol, Eq: 4) and dry tetrahydrofuran (20 ml) were mixed under argon. A suspension of 6-bromoindolin-2-one (5 g, 23.6 mmol, Eq: 1.00) in dry tetrahydrofuran (50 ml) was added in portions. The mixture was stirred at room temperature for 20 min. Then iodomethane (13.4 g, 5.87 ml, 94.3 mmol, Eq: 4) was added dropwise at 23-26° C. The light brown suspension was stirred at room temperature overnight. The reaction mixture was carefully quenched with 10 ml of saturated ammonium chloride. The mixture was diluted with 200 ml of ethyl acetate, 100 ml of water and 50 ml of saturated sodium bicarbonate. The mixture was extracted with 100 ml of ethyl acetate (2×) and the organic layers were washed with 50 ml of saturated sodium bicarbonate. The combined organic layers were dried with sodium sulfate, filtered and concentrated in vacuo.

The residue was purified by chromatography on silica gel to afford the desired product a white solid (4.16 g, 69%). MS (m/z)=254.4/256.4 [M+H]+.

b) 1',3,3,3',3'-Pentamethyl-6-(2-methylpyrimidin-5-yl)-[1,6'-biindoline]-2,2'-dione

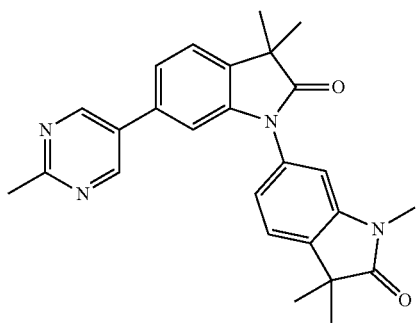

Example 41b was prepared from 3,3-dimethyl-6-(2-methylpyrimidin-5-yl)indolin-2-one (WO2014/202493 A1) with 6-bromo-1,3,3-trimethylindolin-2-one in analogy to example 2 to give the title compound (100%) as an off-white solid. MS (m/z)=427.3 [(M+H)+].

Example 42

1'-(4-Methoxybenzyl)-3,3,3',3'-tetramethyl-6-(2-methylpyrimidin-5-yl)-[1,6'-biindoline]-2,2'-dione

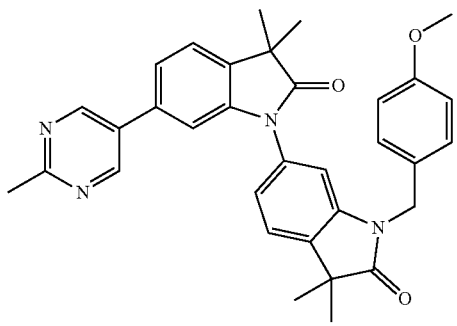

a) 6-Bromo-1-(4-methoxybenzyl)-3,3-dimethylindolin-2-one

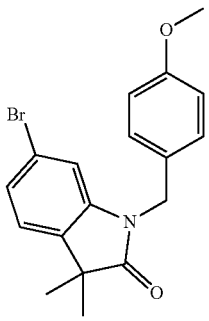 [SMILES: COc1ccc(CN2C(=O)C(C)(C)c3ccc(Br)cc32)cc1]

6-Bromo-3,3-dimethylindolin-2-one (6.58 g, 27.4 mmol, Eq: 1.00, WO2014/202493 A1), 1-(chloromethyl)-4-methoxybenzene (4.72 g, 4.11 ml, 30.1 mmol, Eq: 1.1) and cesium carbonate (17.9 g, 54.8 mmol, Eq: 2) were combined with dimethylformamide (170 ml). The reaction mixture was heated to 80° C. and stirred for 20 h. The crude reaction mixture was concentrated in vacuo. The reaction mixture was poured into 200 mL of water and extracted with ethyl acetate (2×200 mL). The organic layers were washed with water, dried over sodium sulfate and concentrated in vacuo.

The residue was purified by chromatography on silica gel to afford the desired product as a light brown crystalline solid (9.18 g, 93%). MS (m/z)=362.4 [(M+H)+].

b) 1'-(4-Methoxybenzyl)-3,3,3',3'-tetramethyl-6-(2-methylpyrimidin-5-yl)-[1,6'-biindoline]-2,2'-dione

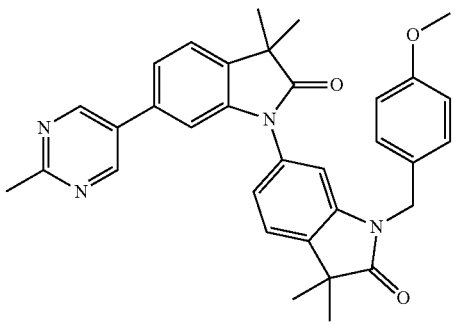

Example 42b was prepared from 3,3-dimethyl-6-(2-methylpyrimidin-5-yl)indolin-2-one (WO2014/202493 A1) with 6-bromo-1-(4-methoxybenzyl)-3,3-dimethylindolin-2-one in analogy to example 2 to give the title compound (97%) as a light yellow foam.

MS (m/z)=533.4 [(M+H)+].

Example 43

6-(3,3-Dimethyl-6-(2-methylpyrimidin-5-yl)-2-oxoindolin-1-yl)-3,3-dimethyl-1H-pyrrolo[3,2-c]pyridin-2(3H)-one

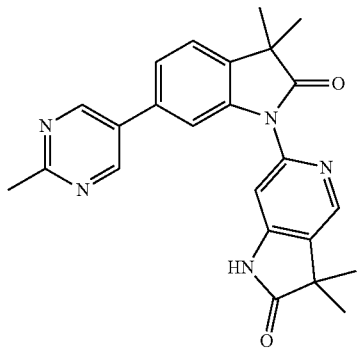

a) 6-Chloro-1-(methoxymethyl)-3,3-dimethyl-1H-pyrrolo[3,2-c]pyridin-2(3H)-one

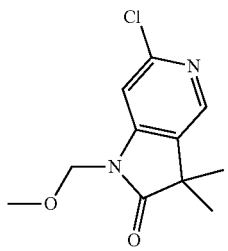

6-Chloro-3,3-dimethyl-1H-pyrrolo[3,2-c]pyridin-2(3H)-one (70 mg, 356 µmol, Eq: 1, PCT Int. Appl., 2012143726) and sodium hydride (17.1 mg, 427 µmol, Eq: 1.2) were combined with dimethylformamide (890 µl) and tetrahydrofuran (890 µl) at 10° C. After 30 min, chloro(methoxy)methane (43 mg, 40.6 µl, 534 µmol, Eq: 1.5) was added and the reaction mixture was stirred at room temperature for 2 h. The reaction mixture was poured into water and extracted with ethyl acetate. The organic layers were washed with water, dried over sodium sulfate, filtered and concentrated in vacuo.

The residue was purified by chromatography on silica gel to afford the desired product as a light yellow solid (68 mg, 79%). MS (m/z)=241.1 [M+H]+.

b) 6-(3,3-Dimethyl-6-(2-methylpyrimidin-5-yl)-2-oxoindolin-1-yl)-1-(methoxymethyl)-3,3-dimethyl-1H-pyrrolo[3,2-c]pyridin-2(3H)-one

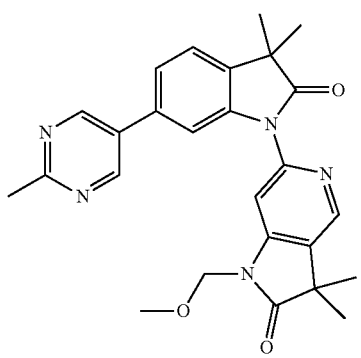

Example 43b was prepared from 3,3-dimethyl-6-(2-methylpyrimidin-5-yl)indolin-2-one (WO2014/202493 A1) with 6-chloro-1-(methoxymethyl)-3,3-dimethyl-1H-pyrrolo[3,2-c]pyridin-2(3H)-one in analogy to example 37b to give the title compound (94%) as an orange foam. MS (m/z)=458.3 [(M+H)+].

c) 6-(3,3-Dimethyl-6-(2-methylpyrimidin-5-yl)-2-oxoindolin-1-yl)-3,3-dimethyl-1H-pyrrolo[3,2-c]pyridin-2(3H)-one

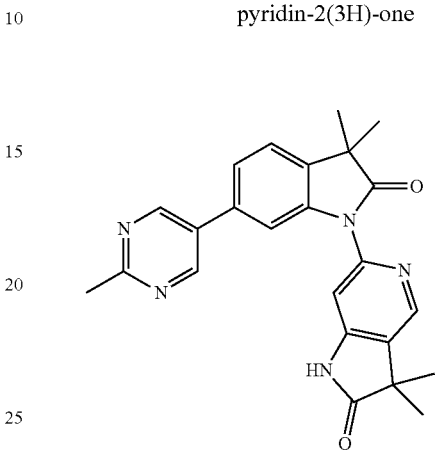

6-(3,3-Dimethyl-6-(2-methylpyrimidin-5-yl)-2-oxoindolin-1-yl)-1-(methoxymethyl)-3,3-dimethyl-1H-pyrrolo[3,2-c]pyridin-2(3H)-one (111 mg, 243 µmol, Eq: 1) was combined with trifluoroacetic acid (2.43 ml). The reaction mixture was heated to 85° C. in a sealed tube and stirred for 1 day then to 120° C. and stirred for 1.5 days. The reaction mixture was diluted with water, then saturated sodium bicarbonate was added and it was extracted with dichloromethane. The organic layers were dried over sodium sulfate, filtered and concentrated in vacuo. The residue was purified by chromatography on silica gel to afford the desired product as a white solid (49 mg, 48%). MS (m/z)= 414.3 [(M+H)+].

Example 44

3,3,3',3'-Tetramethyl-6-(2-methylpyrimidin-5-yl)-[1,6'-biindoline]-2,2'-dione

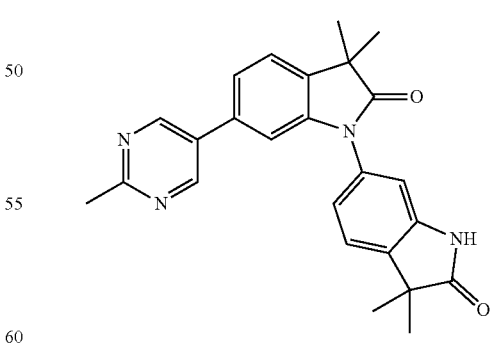

A solution of 1'-(4-methoxybenzyl)-3,3,3',3'-tetramethyl-6-(2-methylpyrimidin-5-yl)-[1,6'-biindoline]-2,2'-dione (0.21 g, 394 µmol, Eq: 1, Example 42) in trifluoroacetic acid (1.78 g, 1.2 ml, 15.6 mmol, Eq: 39.5) was heated to 110° C. for 10 h. The reaction mixture was diluted with dichloromethane and concentrated in vacuo. The reaction mixture was diluted with ethyl acetate, water and basified with 1M sodium carbonate. The mixture was extracted 2 times with ethyl acetate and the organic layers were washed with 1M sodium bicarbonate. The combined organic layers were dried with sodium sulfate, filtered and concentrated in vacuo.

The residue was purified by chromatography on silica gel to afford the desired product as a light yellow solid (123 mg, 75%). MS (m/z)=413.3 [(M+H)+].

Example 45

3,3-Dimethyl-1-(2-methyloxazolo[4,5-b]pyridin-5-yl)-6-(2-methylpyrimidin-5-yl)indolin-2-one

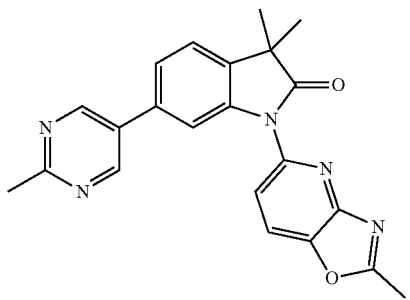

3,3-Dimethyl-6-(2-methylpyrimidin-5-yl)indolin-2-one (100 mg, 395 µmol, Eq: 1, WO2014/202493 A1), 5-bromo-2-methyloxazolo[4,5-b]pyridine (109 mg, 513 µmol, Eq: 1.30), copper (I) iodide (7.52 mg, 39.5 µmol, Eq: 0.10), potassium carbonate (109 mg, 790 µmol, Eq: 2.00) and (1R,2R)—N1,N2-dimethylcyclohexane-1,2-diamine (11.6 mg, 12.8 µl, 79 µmol, Eq: 0.20) were combined with degassed dioxane (6 ml) and flushed with nitrogen. The reaction mixture was heated to 110° C. and stirred for 24 h under nitrogen atmosphere. The reaction mixture was poured into saturated sodium bicarbonate and extracted with ethyl acetate (2×). The organic layers were combined and washed with water and brine. The organic phase was dried over sodium sulfate, filtered and concentrated in vacuo.

The residue was purified by chromatography on silica gel to afford the desired product as a yellow solid (50 mg, 32%). MS (m/z)=386.3 [(M+H)+].

Example 46

7'-Fluoro-1',3,3,3',3'-pentamethyl-6-(2-methylpyrimidin-5-yl)-[1,6'-biindoline]-2,2'-dione

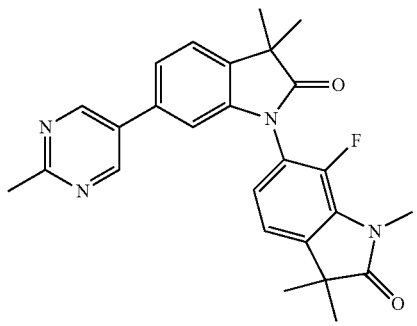

a) 7-Fluoro-1,3,3-trimethylindolin-2-one

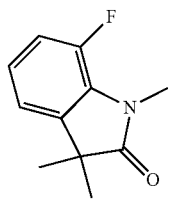

Sodium hydride (6.35 g, 159 mmol, Eq: 4) was suspended in tetrahydrofuran (72.3 ml) and 7-fluoroindolin-2-one (6 g, 39.7 mmol, Eq: 1.00) was added portionwise during 20 min. The reaction mixture was stirred at room temperature for 4 h. The reaction was quenched with 20 ml of ammonium chloride at 5-15° C. and then was diluted with tert-butyl methyl ether and water. The mixture was extracted with tert-butyl methyl ether (2×) and washed with brine. The combined organic phases were dried over sodium sulfate, filtered and concentrated in vacuo. The residue was purified by chromatography on silica gel to afford the desired product as a pink solid (7.48 g, 97%). MS (m/z)=194.4 [M+H]+.

b) 7-Fluoro-1,3,3-trimethyl-6-(trimethylsilyl)indolin-2-one

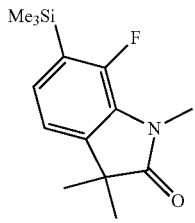 [SMILES: CN1C(=O)C(C)(C)c2ccc([Si](C)(C)C)c(F)c21]

7-Fluoro-1,3,3-trimethylindolin-2-one (7.4 g, 38.3 mmol, Eq: 1.00) and trimethylsilyl chloride (4.58 g, 5.38 ml, 42.1 mmol, Eq: 1.1) were dissolved in dry tetrahydrofuran (57.4 ml). The mixture was cooled to −75° C. and a fresh solution of lithium diisopropylamide (prepared from diisopropylamine (4.5 g, 6.34 ml, 44.0 mmol, Eq: 1.15) and n-buthyl lithium (26.3 ml, 42.1 mmol, Eq: 1.1) in dry tetrahydrofuran (19.1 ml) at −40° C.) was added dropwise during 10 min (increase of temperature maximum to −68° C.). The reaction mixture was stirred for 4 h in an ice bath then at room temperature overnight. The reaction mixture was quenched with water and extracted with ethyl acetate (2×). The organic phase was washed with brine, dried over sodium sulfate, filtered and concentrated in vacuo.

The residue was purified by chromatography on silica gel to afford the desired product as an orange solid (6.32 g, 62%). MS (m/z)=266.5 [M+H]+.

c) 7-Fluoro-6-iodo-1,3,3-trimethylindolin-2-one

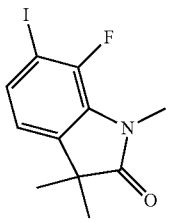

7-Fluoro-1,3,3-trimethyl-6-(trimethylsilyl)indolin-2-one (6.23 g, 23.5 mmol, Eq: 1.00) was dissolved in dry dichloromethane (354 ml). The reaction was cooled to 0° C. and iodine monochloride, 1M in dichloromethane (23.5 ml, 23.5 mmol, Eq: 1.00) was added dropwise. The reaction mixture was stirred at room temperature overnight. Iodine monochloride, 1M in dichloromethane (11.7 ml, 11.7 mmol, Eq: 0.5) was added again and stirred for 45 min. The reaction mixture was quenched with sodium thiosulfate and it was stirred for 30 min. The mixture was extracted with dichloromethane and washed with water. The organic phase was dried over sodium sulfate, filtered and concentrated in vacuo.

The residue was purified by chromatography on silica gel to afford the desired product as an orange solid (6.84 g, 91%). MS (m/z)=320.3 [M+H]+.

d) 7'-Fluoro-1',3,3,3',3'-pentamethyl-6-(2-methylpyrimidin-5-yl)-[1,6'-biindoline]-2,2'-dione

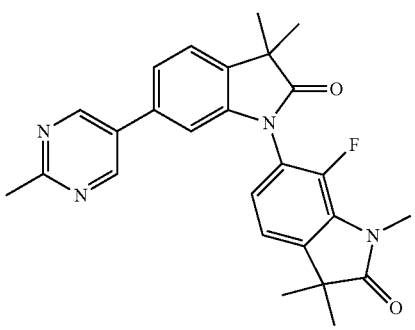

Example 46d was prepared from 3,3-dimethyl-6-(2-methylpyrimidin-5-yl)indolin-2-one (WO2014/202493 A1) with 7-fluoro-6-iodo-1,3,3-trimethylindolin-2-one in analogy to example 2 to give the title compound (18%) as a colorless amorphous solid. MS (m/z)=445.3 [(M+H)+].

Example 47

6-(3,3-Dimethyl-6-(2-methylpyrimidin-5-yl)-2-oxoindolin-1-yl)-4-methyl-2H-benzo[b][1,4]oxazin-3(4H)-one

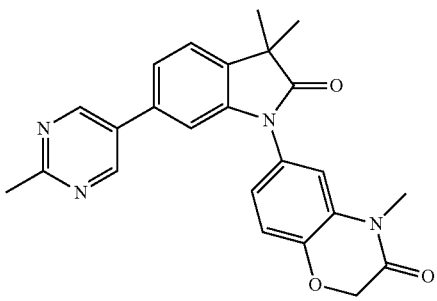 [SMILES: Cc1ncc(-c2ccc3c(c2)N(c2ccc4c(c2)N(C)C(=O)CO4)C(=O)C3(C)C)cn1]

Example 47 was prepared from 3,3-dimethyl-6-(2-methylpyrimidin-5-yl)indolin-2-one (WO2014/202493 A1) with 6-bromo-4-methyl-2H-benzo[b][1,4]oxazin-3(4H)-one in analogy to example 45 to give the title compound (55%) as an off-white solid. MS (m/z)=415.3 [(M+H)+].

Example 48

3,3-Dimethyl-1-(1-methyl-1H-benzo[d][1,2,3]triazol-6-yl)-6-(2-methylpyrimidin-5-yl)indolin-2-one

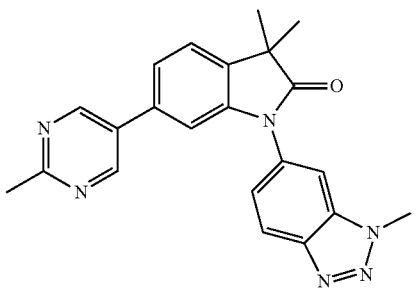

Example 48 was prepared from 3,3-dimethyl-6-(2-methylpyrimidin-5-yl)indolin-2-one (WO2014/202493 A1) with 6-bromo-1-methyl-1H-benzo[d][1,2,3]triazole in analogy to example 2 to give the title compound (80%) as an off-white solid. MS (m/z)=385.3 [(M+H)+].

Example 49

3,3-Dimethyl-6-(2-methylpyrimidin-5-yl)-1-(5-morpholinopyrazin-2-yl)indolin-2-one

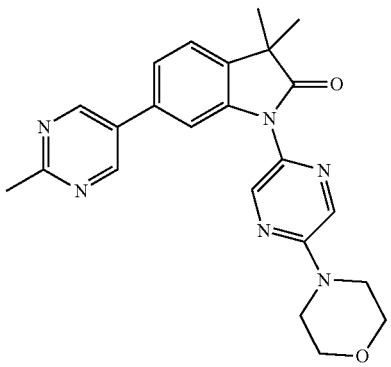 [SMILES: Cc1ncc(-c2ccc3c(c2)N(c2cnc(N4CCOCC4)cn2)C(=O)C3(C)C)cn1]

Example 49 was prepared from 3,3-dimethyl-6-(2-methylpyrimidin-5-yl)indolin-2-one (WO2014/202493 A1) with 4-(5-bromopyrazin-2-yl)morpholine in analogy to example 2 to give the title compound (81%) as a white solid. MS (m/z)=417.2 [(M+H)+].

Example 50

3,3-Dimethyl-1-(5-(2-methyl-1H-imidazol-1-yl)pyrazin-2-yl)-6-(2-methylpyrimidin-5-yl)indolin-2-one

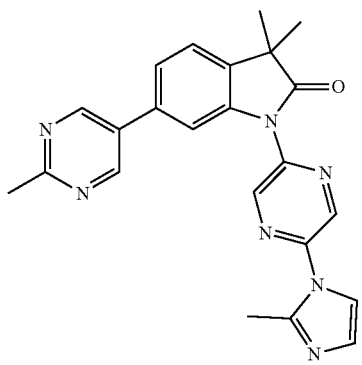 [SMILES: Cc1ncc(-c2ccc3c(c2)N(c2cnc(-n4ccnc4C)cn2)C(=O)C3(C)C)cn1]

Example 50 was prepared from 3,3-dimethyl-6-(2-methylpyrimidin-5-yl)indolin-2-one (WO2014/202493 A1) with 2-bromo-5-(2-methyl-1H-imidazol-1-yl)pyrazine in analogy to example 2 to give the title compound (91%) as a light yellow solid.
MS (m/z)=412.2 [(M+H)$^+$].

Example 51

1-(5-((1R,5S)-3-Oxa-6-azabicyclo[3.1.1]heptan-6-yl)pyrazin-2-yl)-3,3-dimethyl-6-(2-methylpyrimidin-5-yl)indolin-2-one

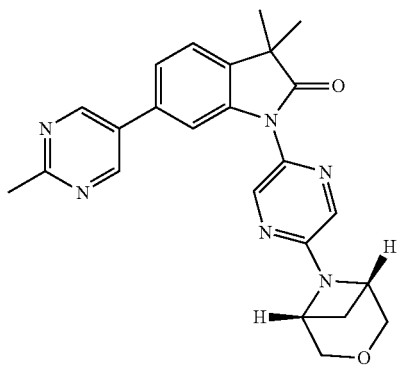 [SMILES: Cc1ncc(-c2ccc3c(c2)N(c2cnc(N4[C@@H]5COC[C@H]4C5)cn2)C(=O)C3(C)C)cn1]

a) (1R,5S)-6-(5-Bromopyrazin-2-yl)-3-oxa-6-azabicyclo[3.1.1]heptane

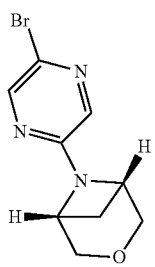 [SMILES: Brc1cnc(N2[C@@H]3COC[C@H]2C3)cn1]

2,5-Dibromopyrazine (70 mg, 288 μmol, Eq: 1) was dissolved in dimethylsulfoxide (961 μl). Cesium Fluoride (131 mg, 865 μmol, Eq: 3) and 3-oxa-6-azabicyclo[3.1.1]heptane 2,2,2-trifluoroacetate (61.5 mg, 288 μmol, Eq: 1) were added. The reaction mixture was stirred at 70° C. for 48 h. The reaction mixture was diluted with water and extracted with ethyl acetate (2×). The combined organic phases were washed with brine, dried over sodium sulfate, filtered and concentrated in vacuo.

The residue was purified by chromatography on silica gel to afford the desired product as an off-white solid (41 mg, 56%). MS (m/z)=256.1 [M+H]+.

b) 1-(5-((1R,5S)-3-Oxa-6-azabicyclo[3.1.1]heptan-6-yl)pyrazin-2-yl)-3,3-dimethyl-6-(2-methylpyrimidin-5-yl)indolin-2-one

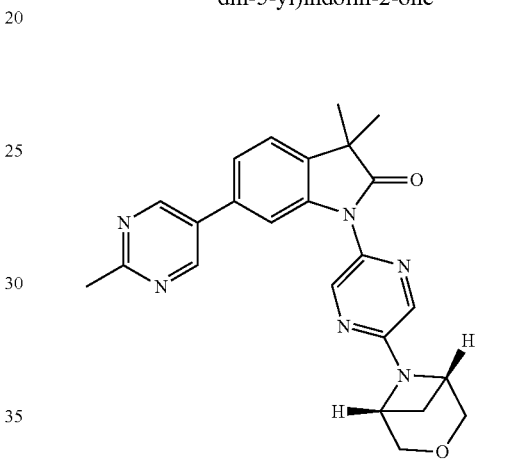

Example 51b was prepared from 3,3-dimethyl-6-(2-methylpyrimidin-5-yl)indolin-2-one (WO2014/202493 A1) with (1R,5S)-6-(5-bromopyrazin-2-yl)-3-oxa-6-azabicyclo[3.1.1]heptane in analogy to example 2 to give the title compound (86%) as an off-white solid. MS (m/z)=429.2 [(M+H)$^+$].

Example 52

1-(5-((2-Hydroxyethyl)amino)pyrazin-2-yl)-3,3-dimethyl-6-(2-methylpyrimidin-5-yl)indolin-2-one

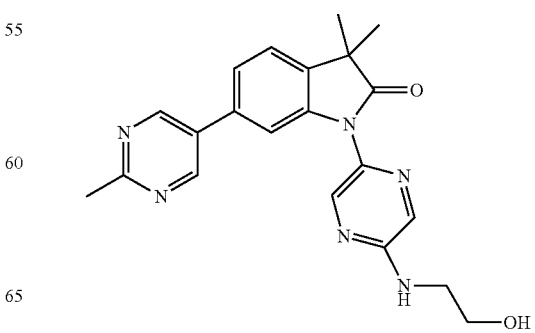

a) 2-((5-Bromopyrazin-2-yl)amino)ethanol

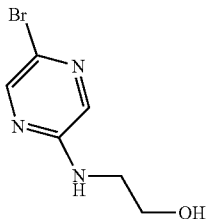 [SMILES: OCCNc1cnc(Br)cn1]

Example 52a was prepared from 2,5-dibromopyrazine with 2-aminoethanol in analogy to example 51a to give the title compound (60%) as an off-white solid.
MS (m/z)=220.0 [(M+H)$^+$].

b) 1-(5-((2-Hydroxyethyl)amino)pyrazin-2-yl)-3,3-dimethyl-6-(2-methylpyrimidin-5-yl)indolin-2-one

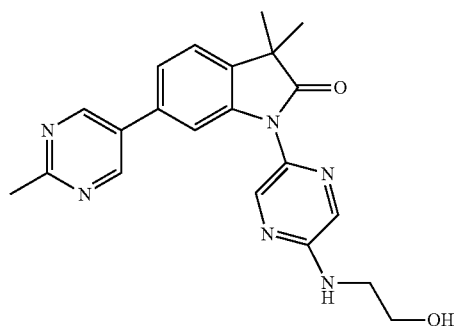 [SMILES: Cc1ncc(-c2ccc3c(c2)N(c2cnc(NCCO)cn2)C(=O)C3(C)C)cn1]

Example 52b was prepared from 3,3-dimethyl-6-(2-methylpyrimidin-5-yl)indolin-2-one (WO2014/202493 A1) with 2((5-bromopyrazin-2-yl)amino)ethanol in analogy to example 2 to give the title compound (82%) as a white foam.
MS (m/z)=391.3 [(M+H)$^+$].

Example 53

7-Cyclopropyl-3-(3,3-dimethyl-6-(2-methylpyrimidin-5-yl)-2-oxoindolin-1-yl)-5,5-dimethyl-5H-pyrrolo[2,3-c]pyridazin-6(7H)-one

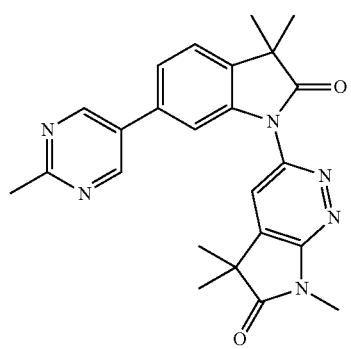 [SMILES: Cc1ncc(-c2ccc3c(c2)N(c2cc4c(nn2)N(C)C(=O)C4(C)C)C(=O)C3(C)C)cn1]

a) 3,6-Dichloro-N-cyclopropylpyridazin-4-amine

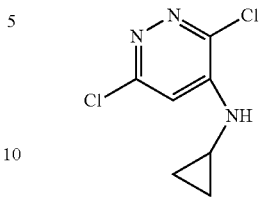

3,4,6-Trichloropyridazine (10 g, 53.4 mmol, Eq: 1.00) and cyclopropanamine (31.1 g, 38.2 ml, 534 mmol, Eq: 10) were combined with tetrahydrofuran (100 ml). The reaction mixture was heated to 50° C. and stirred for 3 h. The reaction mixture was diluted with ethyl acetate and water. The mixture was extracted 2 times with ethyl acetate and the organic layers washed with brine. The combined organic layers were dried with sodium sulfate, filtered and concentrated in vacuo. The residue was purified by chromatography on silica gel to afford the desired product as a light yellow crystalline solid (9.75 g, 89%). MS (m/z)=204/206 [M+H]+.

b) 5,8-Dichloro-1-cyclopropyl-7-isobutyryl-3,3-dimethyl-1,6,7-triazaspiro[3.5]nona-5,8-dien-2-one

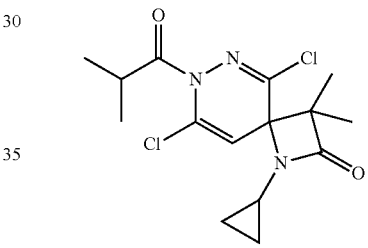

3,6-Dichloro-N-cyclopropylpyridazin-4-amine (8.68 g, 42.5 mmol, Eq: 1.00), triethylamine (7.75 g, 10.7 ml, 76.6 mmol, Eq: 1.8) and isobutyryl chloride (6.94 g, 6.82 ml, 63.8 mmol, Eq: 1.5) were combined with dichloromethane (130 ml) and stirred for 20 h at room temperature. The reaction mixture was diluted with methylene chloride and water and extracted 2 times with methylene chloride. The combined organic layers were dried with sodium sulfate, filtered and concentrated in vacuo.

The residue was purified by chromatography on silica gel to afford the desired product as a yellow solid (13.75 g, 93%). MS (m/z)=344.09 [M+H]+.

c) 3-Chloro-7-cyclopropyl-5,5-dimethyl-5H-pyrrolo[2,3-c]pyridazin-6(7H)-one

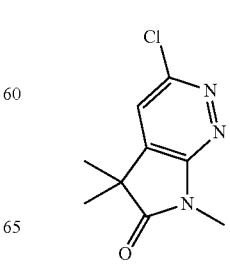

5,8-Dichloro-1-cyclopropyl-7-isobutyryl-3,3-dimethyl-1,6,7-triazaspiro[3.5]nona-5,8-dien-2-one (10.4 g, 30.3 mmol, Eq: 1) and sodium tert-butoxide (5.82 g, 60.6 mmol, Eq: 2) were combined with dioxane (250 ml). The flask was evacuated and flushed with argon 3 times. Then di-1-adamantylphosphine oxide (214 mg, 606 µmol, Eq: 0.02) and palladium (II) acetate (136 mg, 606 µmol, Eq: 0.02) were added and stirred at 80° C. overnight. The crude reaction mixture was concentrated in vacuo.

The residue was purified by chromatography on silica gel to afford the desired product as a light yellow crystalline solid (2 g, 27%). MS (m/z)=238.2 [M+H]+.

d) 7-Cyclopropyl-3-(3,3-dimethyl-6-(2-methylpyrimidin-5-yl)-2-oxoindolin-1-yl)-5,5-dimethyl-5H-pyrrolo[2,3-c]pyridazin-6(7H)-one

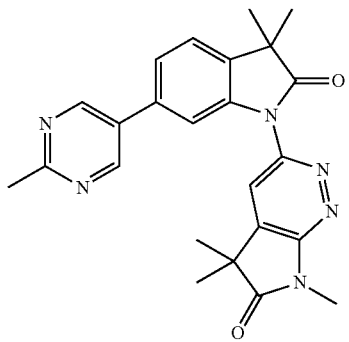 [SMILES: Cc1ncc(-c2ccc3c(c2)N(c2cc4c(nn2)N(C)C(=O)C4(C)C)C(=O)C3(C)C)cn1]

Example 53d was prepared from 3,3-dimethyl-6-(2-methylpyrimidin-5-yl)indolin-2-one (WO2014/202493 A1) with 3-chloro-7-cyclopropyl-5,5-dimethyl-5H-pyrrolo[2,3-c]pyridazin-6(7H)-one in analogy to example 37b to give the title compound (46%) as a white solid.
MS (m/z)=455.3 [(M+H)+].

Example 54

5-(3,3-Dimethyl-6-(2-methylpyrimidin-5-yl)-2-oxoindolin-1-yl)-1,3,3-trimethyl-1H-pyrrolo[2,3-b]pyridin-2(3H)-one

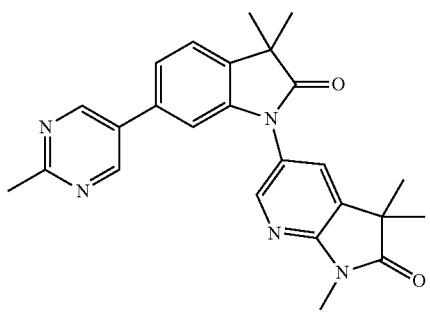

a) 5-Bromo-1,3,3-trimethyl-1H-pyrrolo[2,3-b]pyridin-2(3H)-one

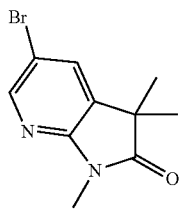

5-Bromo-1H-pyrrolo[2,3-b]pyridin-2(3H)-one (500 mg, 2.35 mmol, Eq: 1) was combined with dimethylformamide (4 ml). Sodium hydride (113 mg, 2.82 mmol, Eq: 1.20) and iodomethane (500 mg, 223 µl, 3.52 mmol, Eq: 1.50) were added and it was stirred at room temperature for 2 h. The reaction mixture was poured into water and extracted with ethyl acetate (2×). The organic layers were combined and washed with brine, dried over sodium sulfate and concentrated in vacuo.

The residue was purified by chromatography on silica gel to afford the desired product as a yellow solid (150 mg, 25%). MS (m/z)=255.1 [M+H]+.

b) 5-(3,3-Dimethyl-6-(2-methylpyrimidin-5-yl)-2-oxoindolin-1-yl)-1,3,3-trimethyl-1H-pyrrolo[2,3-b]pyridin-2(3H)-one

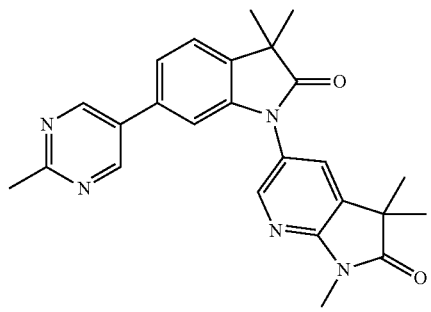

Example 54b was prepared from 3,3-dimethyl-6-(2-methylpyrimidin-5-yl)indolin-2-one (WO2014/202493 A1) with 5-bromo-1,3,3-trimethyl-1H-pyrrolo[2,3-b]pyridin-2(3H)-one in analogy to example 45 to give the title compound (83%) as a light yellow solid.
MS (m/z)=428.4 [(M+H)+].

Example 55 rac-(1S,5R)-4-(6-(3,3-Dimethyl-6-(2-methylpyrimidin-5-yl)-2-oxoindolin-1-yl)pyrazin-2-yl)-2-oxa-4-azabicyclo[3.2.0]heptan-3-one

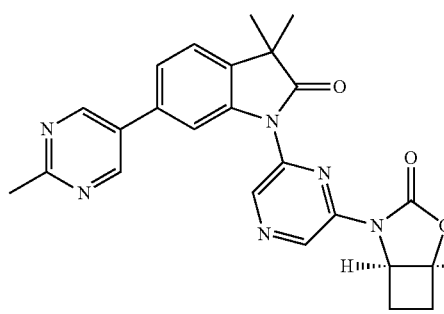

1-(6-Chloropyrazin-2-yl)-3,3-dimethyl-6-(2-methylpyrimidin-5-yl)indolin-2-one (0.08 g, 219 Eq: 1, Example 6a), rac-(1S,5R)-2-oxa-4-azabicyclo[3.2.0]heptan-3-one (32.2 mg, 284 Eq: 1.3) and potassium carbonate (60.4 mg, 437

µmol, Eq: 2) were mixed in acetonitrile (1.09 ml) in a pressure tube and argon was bubbled through the reaction mixture for 5 minutes. Then N,N'-dimethylethylenediamine (7.71 mg, 9.42 µl, 87.5 µmol, Eq: 0.4) and copper(I) iodide (8.33 mg, 43.7 µmol, Eq: 0.2) were added, it was flushed again for 2 minutes with argon, the tube was sealed and the reaction heated to 120° C. for 24 h.

The residue was purified by chromatography on silica gel to afford the desired product as a white solid (19 mg, 19%). MS (m/z)=443.4 [M+H]+.

Example 56

3-(6-(3,3-Dimethyl-6-(2-methylpyrimidin-5-yl)-2-oxoindolin-1-yl)pyrazin-2-yl)-5,5-dimethyloxazolidin-2-one

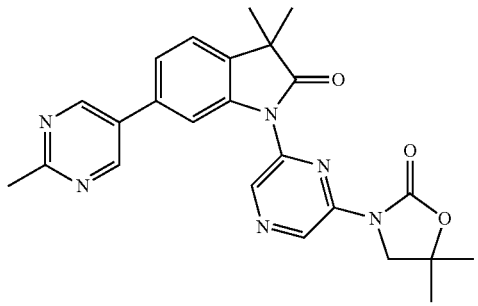

Example 56 was prepared from 1-(6-chloropyrazin-2-yl)-3,3-dimethyl-6-(2-methylpyrimidin-5-yl)indolin-2-one (Example 6a) with 5,5-dimethyloxazolidin-2-one in analogy to example 55 to give the title compound (43%) as a white solid. MS (m/z)=445.3 [(M+H)$^+$].

Example 57

1-(6-(1,1-Dioxidoisothiazolidin-2-yl)pyrazin-2-yl)-3,3-dimethyl-6-(2-methylpyrimidin-5-yl)indolin-2-one

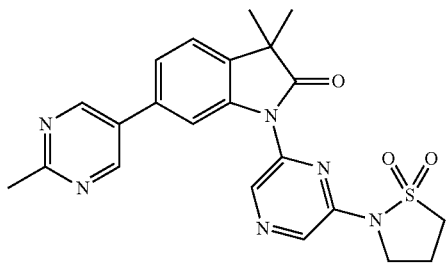 [SMILES: Cc1ncc(-c2ccc3c(c2)N(c2cncc(N4CCCS4(=O)=O)n2)C(=O)C3(C)C)cn1]

Example 57 was prepared from 1-(6-chloropyrazin-2-yl)-3,3-dimethyl-6-(2-methylpyrimidin-5-yl)indolin-2-one (Example 6a) with isothiazolidine 1,1-dioxide in analogy to example 55 to give the title compound (50%) as a light yellow solid. MS (m/z)=451.3 [(M+H)$^+$].

Example 58

3,3-Dimethyl-6-(2-methylpyrimidin-5-yl)-1-(1H-pyrrolo[2,3-b]pyridin-6-yl)indolin-2-one

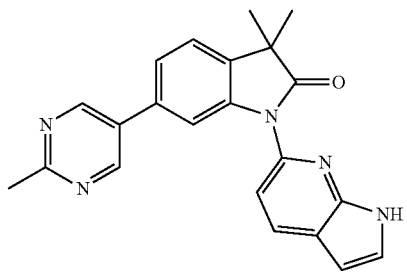 [SMILES: Cc1ncc(-c2ccc3c(c2)N(c2ccc4cc[nH]c4n2)C(=O)C3(C)C)cn1]

Example 58 was prepared from 3,3-dimethyl-6-(2-methylpyrimidin-5-yl)indolin-2-one (WO2014/202493 A1) with 6-chloro-1H-pyrrolo[2,3-b]pyridine in analogy to example 18b to give the title compound (9%) as an amorphous yellow solid. MS (m/z)=370.2 [(M+H)$^+$].

Example 59

3,3,3',3'-Tetramethyl-6-(2-methylpyrimidin-5-yl)-1'-(oxetan-3-yl)-[1,6'-biindoline]-2,2'-dione

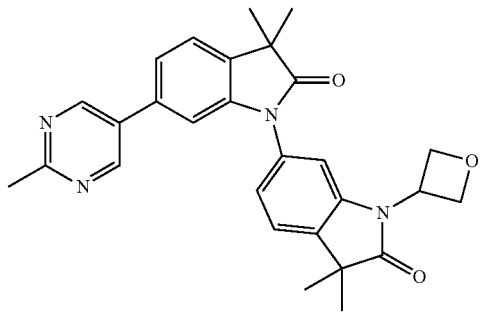 [SMILES: Cc1ncc(-c2ccc3c(c2)N(c2ccc4c(c2)N(C2COC2)C(=O)C4(C)C)C(=O)C3(C)C)cn1]

Example 59 was prepared from 3,3-dimethyl-6-(2-methylpyrimidin-5-yl)indolin-2-one (from WO2014/202493 A1) with 6-promo-3,3-dimethyl-1-(oxetan-3-yl)indolin-2-one (from WO2014/202493 A1) in analogy to example 2 to give the title compound (100%) as a white solid. MS (m/z)=469.3 [(M+H)$^+$].

Example 60

3,3-Dimethyl-1-(1-methyl-1H-indazol-6-yl)-6-(2-methylpyrimidin-5-yl)indolin-2-one

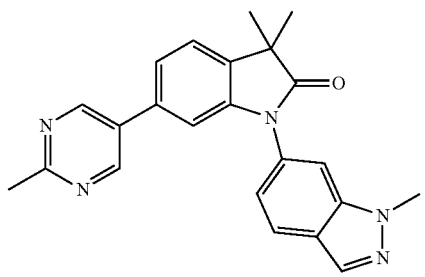

Example 60 was prepared from 3,3-dimethyl-6-(2-methylpyrimidin-5-yl)indolin-2-one (from WO2014/202493 A1) with 6-promo-1-methyl-1H-indazole in analogy to example 2 to give the title compound (99%) as a white solid. MS (m/z)=384.3 [(M+H)$^+$].

Example 61

1-(1,3-Dimethyl-1H-pyrazolo[3,4-b]pyridin-6-yl)-3,3-dimethyl-6-(2-methylpyrimidin-5-yl)indolin-2-one

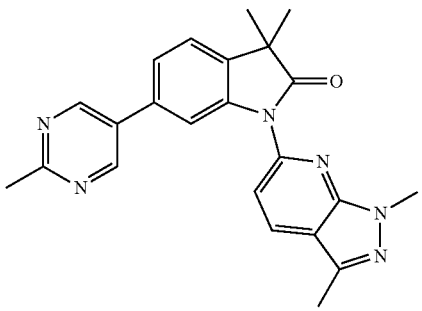

a) 6-Chloro-1,3-dimethyl-1H-pyrazolo[3,4-b]pyridine

To a solution of 1-(2,6-dichloropyridin-3-yl)ethanone (2.21 g, 11.6 mmol, Eq: 1.00) in ethanol (90 ml) was added methylhydrazine (643 mg, 735 µl, 14.0 mmol, Eq: 1.20) and N,N-diisopropylethylamine (1.5 g, 2.03 ml, 11.6 mmol, Eq: 1.00) and the reaction was heated to reflux for 2.5 h. The solution was concentrated, dissolved in dichloromethane and washed with water. The organic layer was dried over sodium sulfate and evaporated in vacuo. The residue was purified by chromatography on silica gel to afford the desired product as yellow crystals (1.57 g, 74%). MS (m/z)=182.1 [M+H]+.

b) 1-(1,3-Dimethyl-1H-pyrazolo[3,4-b]pyridin-6-yl)-3,3-dimethyl-6-(2-methylpyrimidin-5-yl)indolin-2-one

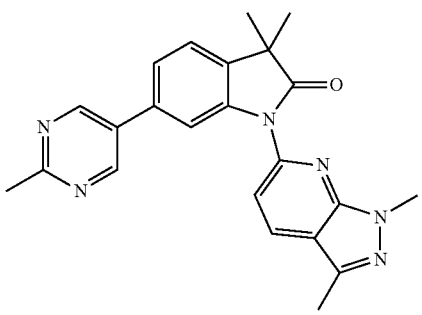

Example 61b was prepared from 3,3-dimethyl-6-(2-methylpyrimidin-5-yl)indolin-2-one (WO2014/202493 A1) with 6-chloro-1,3-dimethyl-1H-pyrazolo[3,4-b]pyridine in analogy to example 18b to give the title compound (81%) as a brown solid. MS (m/z)=399.3 [(M–H)$^+$].

Example 62

3,3-Dimethyl-1-(1-methyl-1H-indol-6-yl)-6-(2-methylpyrimidin-5-yl)indolin-2-one

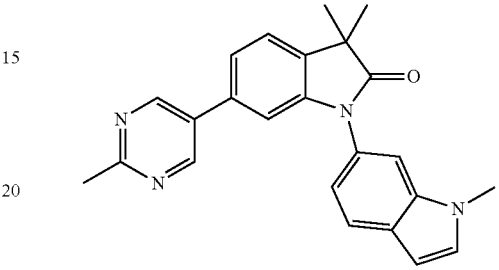

Example 62 was prepared from 3,3-dimethyl-6-(2-methylpyrimidin-5-yl)indolin-2-one (from WO2014/202493 A1) with 6-bromo-1-methyl-1H-indole in analogy to example 2 to give the title compound (86%) as a light brown solid. MS (m/z)=383.3 [(M+H)$^+$].

Biological Assays and Data

Now it has been found that the compounds of formula I may be used for the treatment of CNS diseases.

The described compounds of formula I reduce L-687,414-induced hyperlocomotion. This was assessed by using a computerized Digiscan 16 Animal Activity Monitoring System (Omnitech Electronics, Columbus, Ohio) to quantify locomotor activity. Animals were kept under a 12 h light/dark cycle and experiments were performed during the light period. Each activity monitoring chamber consisted of a Plexiglas box (41×41×28 cm; W×L×H) with sawdust bedding on the floor surrounded by invisible horizontal and vertical infrared sensor beams. The test boxes were divided by a Plexiglas cross providing each mouse with 20×20 cm of moving space. Cages were connected to a Digiscan Analyzer linked to a computer that constantly collected the beam status information. Records of photocell beam interruptions for individual animals were taken every 5 min over the duration of the experimental session and the sum of the first 6 periods was used as the final parameter. At least 8 mice were used in each treatment group. Compounds were administered i.p. 15 min before a s.c. injection of 50 mg/kg of L-687,414. Mice were then transferred from their home cage to the recording chambers for a 15-min habituation phase allowing free exploration of the new environment. Horizontal activity was then recorded for a 30-min time period. The % inhibition of L-687,414-induced hyperlocomotion was calculated according to the equation:

$$((Veh+L\text{-}687,414 \text{ horizontal activity}-drug+L\text{-}687,414 \text{ horizontal activity})/Veh+L\text{-}687,414 \text{ horizontal activity}) \times 100$$

ID$_{50}$ values, defined as doses of each compound producing 50% inhibition of L-687,414-induced hyperlocomotion, were calculated by linear regression analysis of a dose-response data using an Excel-based computer-fitting program.

As data was not presupposed to be normally distributed, groups treated with test compounds were statistically compared with the control (vehicle-treated) group using one-tailed Mann Whitney U tests. In statistics, the Mann-Whitney Utest (also called the Mann-Whitney-Wilcoxon (MWW) or Wilcoxon rank-sum test) is a non-parametric statistical hypothesis test for assessing whether one of two samples of independent observations tends to have larger values than the other. It is one of the most well-known non-parametric significance tests. A p value gives the probability that two groups are significantly different from each other and the value of <0.05 is generally accepted as a criterion, it implies that there is >95% chance that two groups are really different from each other. P values given in table 1 are one-tailed since only decreases in locomotion were expected and tested for (Mann, H. B., Whitney, D. R. (1947), "On a Test of Whether one of Two Random Variables is Stochastically Larger than the Other", Annals of Mathematical Statistics, 18 (1), 50-60).

Determination of Adenosine Transport Activity

To measure adenosine transport activity of ENT-1 mammalian cells, stable cells expressing the mouse ENT-1 transporter were plated on day 1 in 96-well culture plates at the density of 60,000 cells/well, in complete DMEM/F12 medium supplemented with glutamax, 10% FBS and 10 µg/ml puromycin. On day 2, the medium was aspirated and the cells were washed twice with uptake buffer (10 mM Hepes-Tris, pH 7.4 containing 150 mM NaCl, 1 mM $CaCl_2$, 2.5 mM KCl, 2.5 mM $MgSO_4$, 10 mM D-glucose) (UB). For inhibition experiments, cells were then incubated at RT with various concentrations of compounds with 1% DMSO final. Non-specific uptake was defined in the presence of 10 µM S-(4-Nitrobenzyl)-6-thioinosine (NBTI, Sigma Cat #N2255).

A solution containing [2,8-$^3$H]-adenosine 6 nM (40 Ci/mmol, American Radiolabeled chemicals Inc, Cat #ART 0287A) was then immediately added to the wells. The plates were then incubated for 20 min with gentle shaking and the reaction was stopped by aspiration of the mixture and washing (three times) with ice-cold UB. The cells were lysed by the addition of scintillation liquid, shaken 3 hours and the radioactivity in the cells was estimated using a microplates scintillation counter (TopCount NXT, Packard).

TABLE 1

Effects of compounds of formula I on ENT1 inhibition

| Expl. | structure | ENT1, adenosine uptake, IC50 (uM) |
|---|---|---|
| 1 | 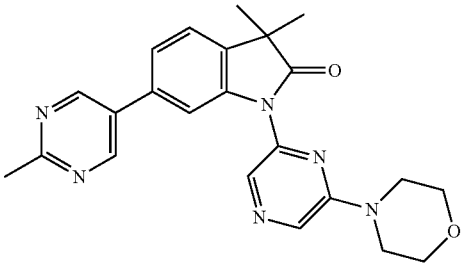 | 0.0390 |
| 2 | 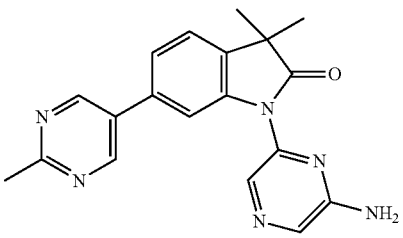 [SMILES: Cc1ncc(-c2ccc3c(c2)N(c2cncc(N)n2)C(=O)C3(C)C)cn1] | 0.1626 |
| 3 | 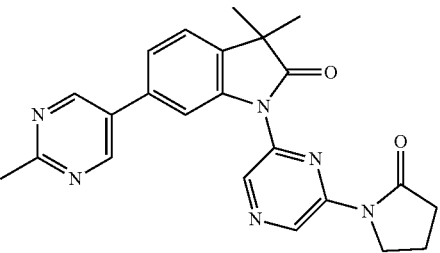 [SMILES: Cc1ncc(-c2ccc3c(c2)N(c2cncc(N4CCCC4=O)n2)C(=O)C3(C)C)cn1] | 0.0570 |

TABLE 1-continued
Effects of compounds of formula I on ENT1 inhibition
| Expl. | structure | ENT1, adenosine uptake, IC50 (uM) |
|---|---|---|
| 4 | 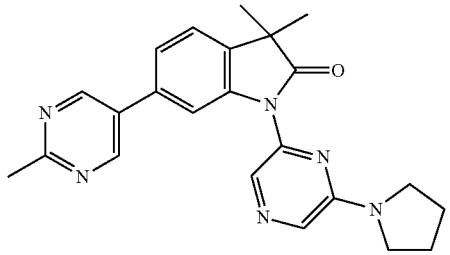 [SMILES: Cc1ncc(-c2ccc3c(c2)N(c2cncc(N4CCCC4)n2)C(=O)C3(C)C)cn1] | 0.2526 |
| 5 | 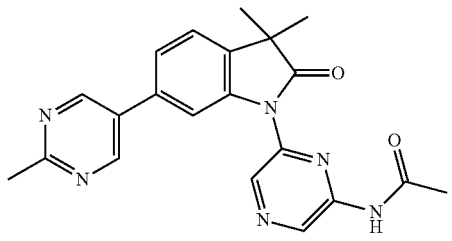 [SMILES: CC(=O)Nc1cncc(N2C(=O)C(C)(C)c3ccc(-c4cnc(C)nc4)cc32)n1] | 0.0480 |
| 6 | 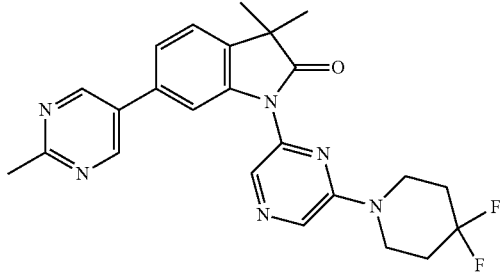 [SMILES: Cc1ncc(-c2ccc3c(c2)N(c2cncc(N4CCC(F)(F)CC4)n2)C(=O)C3(C)C)cn1] | 0.0324 |
| 7 | 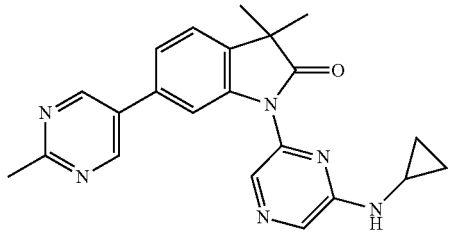 [SMILES: Cc1ncc(-c2ccc3c(c2)N(c2cncc(NC4CC4)n2)C(=O)C3(C)C)cn1] | 0.0396 |
| 8 | 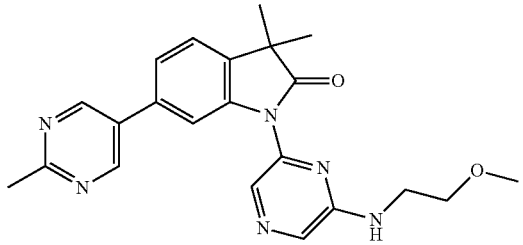 | 0.0876 |

TABLE 1-continued
Effects of compounds of formula I on ENT1 inhibition
| Expl. | structure | ENT1, adenosine uptake, IC50 (uM) |
|---|---|---|
| 9 | 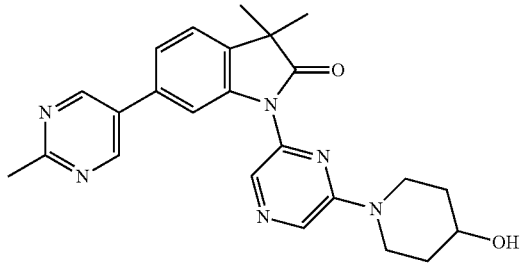 [SMILES: Cc1ncc(-c2ccc3c(c2)N(c2cncc(N4CCC(O)CC4)n2)C(=O)C3(C)C)cn1] | 0.0218 |
| 10 | 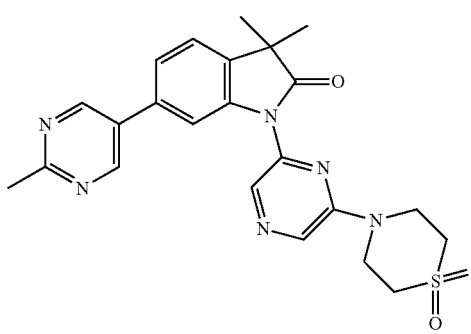 | 0.0296 |
| 11 | 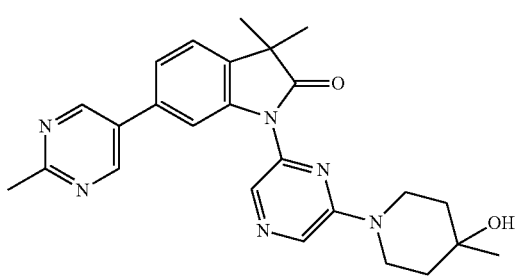 | 0.0338 |
| 12 | 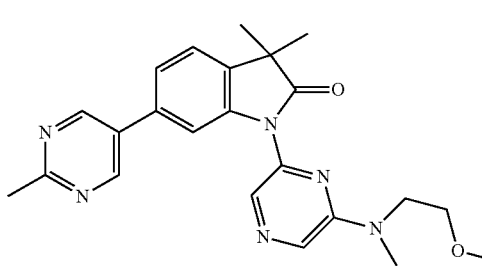 | 0.0545 |
| 13 | 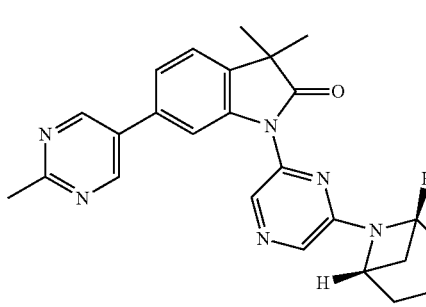 | 0.1374 |

TABLE 1-continued
Effects of compounds of formula I on ENT1 inhibition
| Expl. | structure | ENT1, adenosine uptake, IC50 (uM) |
|---|---|---|
| 14 | 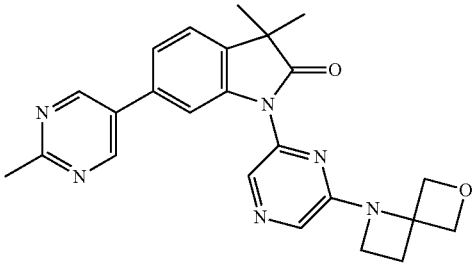 [SMILES: Cc1ncc(-c2ccc3c(c2)N(c2cncc(N4CCC45COC5)n2)C(=O)C3(C)C)cn1] | 0.1103 |
| 15 | 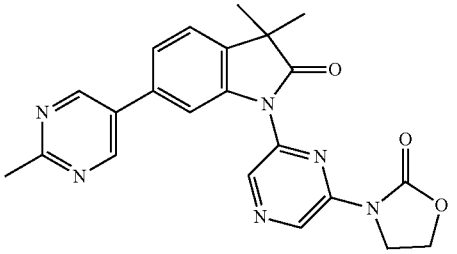 [SMILES: Cc1ncc(-c2ccc3c(c2)N(c2cncc(N4CCOC4=O)n2)C(=O)C3(C)C)cn1] | 0.0260 |
| 16 | 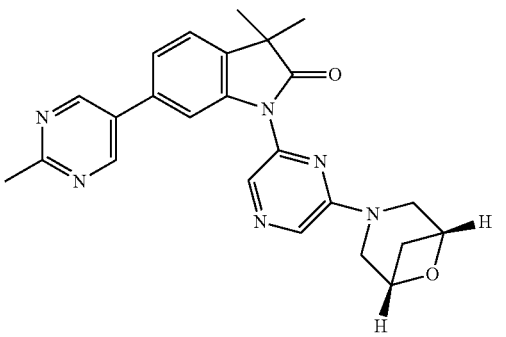 [SMILES: Cc1ncc(-c2ccc3c(c2)N(c2cncc(N4C[C@H]5C[C@@H](C4)O5)n2)C(=O)C3(C)C)cn1] | 0.0887 |
| 17 | 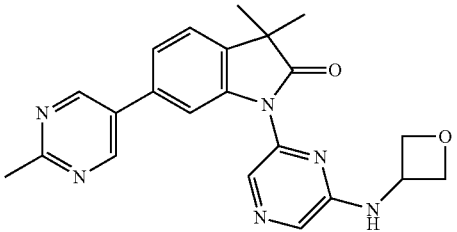 [SMILES: Cc1ncc(-c2ccc3c(c2)N(c2cncc(NC4COC4)n2)C(=O)C3(C)C)cn1] | 0.2443 |
| 18 | 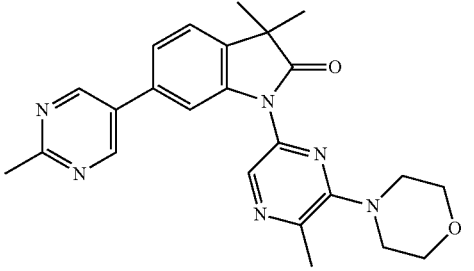 [SMILES: Cc1ncc(-c2ccc3c(c2)N(c2cnc(C)c(N4CCOCC4)n2)C(=O)C3(C)C)cn1] | 0.0970 |

TABLE 1-continued
Effects of compounds of formula I on ENT1 inhibition
| Expl. | structure | ENT1, adenosine uptake, IC50 (uM) |
|---|---|---|
| 19 | 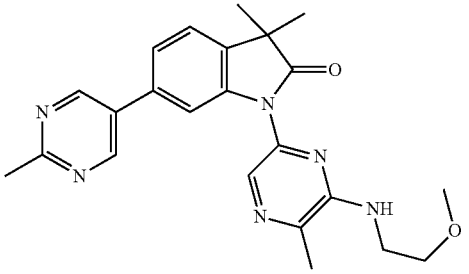 [SMILES: COCCNc1nc(N2C(=O)C(C)(C)c3ccc(-c4cnc(C)nc4)cc32)cnc1C] | 0.1097 |
| 20 | 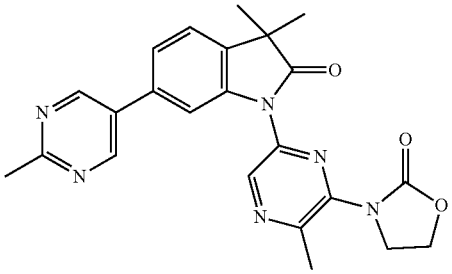 [SMILES: Cc1ncc(-c2ccc3c(c2)N(c2cnc(C)c(N4CCOC4=O)n2)C(=O)C3(C)C)cn1] | 0.0165 |
| 21 | 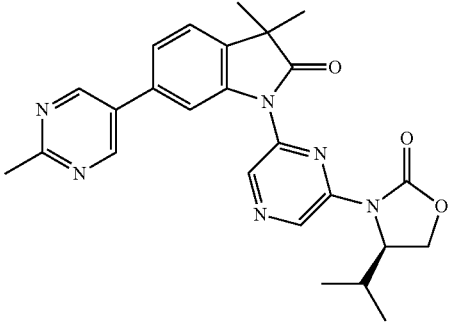 [SMILES: Cc1ncc(-c2ccc3c(c2)N(c2cncc(N4C(=O)OC[C@H]4C(C)C)n2)C(=O)C3(C)C)cn1] | 0.2378 |
| 22 | 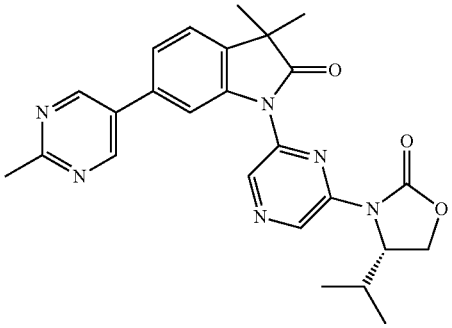 [SMILES: Cc1ncc(-c2ccc3c(c2)N(c2cncc(N4C(=O)OC[C@@H]4C(C)C)n2)C(=O)C3(C)C)cn1] | 0.3873 |
| 23 | 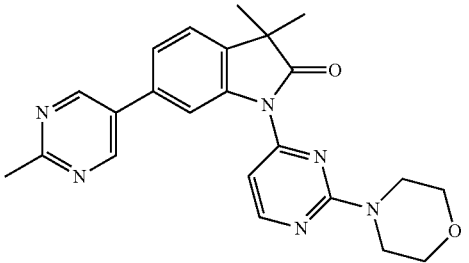 [SMILES: Cc1ncc(-c2ccc3c(c2)N(c2ccnc(N4CCOCC4)n2)C(=O)C3(C)C)cn1] | 0.0522 |

TABLE 1-continued
Effects of compounds of formula I on ENT1 inhibition
| Expl. | structure | ENT1, adenosine uptake, IC50 (uM) |
|---|---|---|
| 24 | 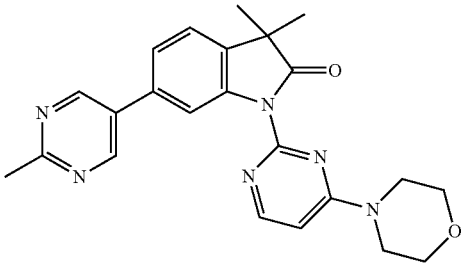 | 0.3206 |
| 25 | 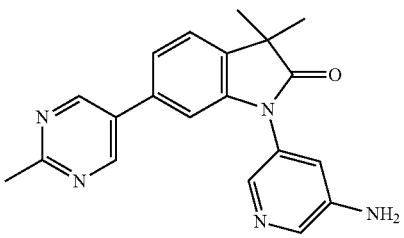 [SMILES: Cc1ncc(-c2ccc3c(c2)N(c2cncc(N)c2)C(=O)C3(C)C)cn1] | 0.4663 |
| 26 | 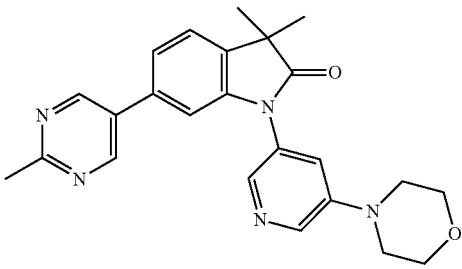 [SMILES: Cc1ncc(-c2ccc3c(c2)N(c2cncc(N4CCOCC4)c2)C(=O)C3(C)C)cn1] | 0.0176 |
| 27 | 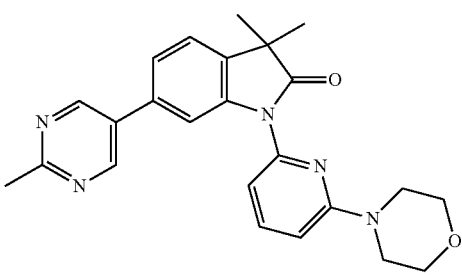 | 0.0575 |
| 28 | 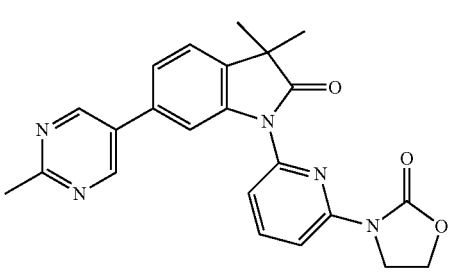 [SMILES: Cc1ncc(-c2ccc3c(c2)N(c2cccc(N4CCOC4=O)n2)C(=O)C3(C)C)cn1] | 0.0050 |

TABLE 1-continued
Effects of compounds of formula I on ENT1 inhibition
| Expl. | structure | ENT1, adenosine uptake, IC50 (uM) |
|---|---|---|
| 29 | 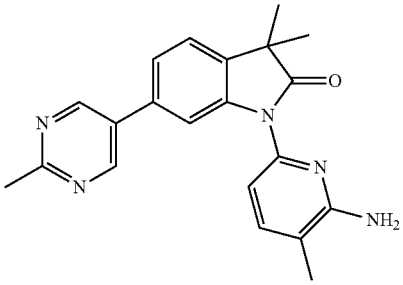 [SMILES: Cc1ncc(-c2ccc3c(c2)N(c2ccc(C)c(N)n2)C(=O)C3(C)C)cn1] | 0.1264 |
| 30 | 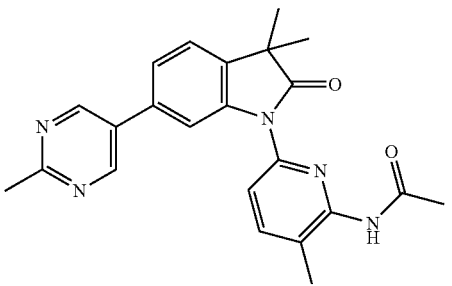 [SMILES: CC(=O)Nc1nc(N2C(=O)C(C)(C)c3ccc(-c4cnc(C)nc4)cc32)ccc1C] | 0.3459 |
| 31 | 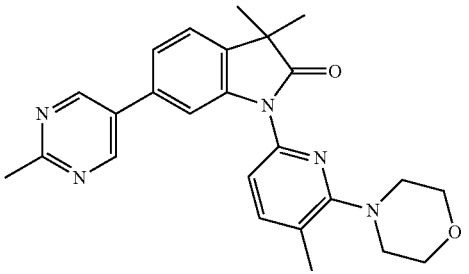 [SMILES: Cc1ncc(-c2ccc3c(c2)N(c2ccc(C)c(N4CCOCC4)n2)C(=O)C3(C)C)cn1] | 0.0401 |
| 32 | 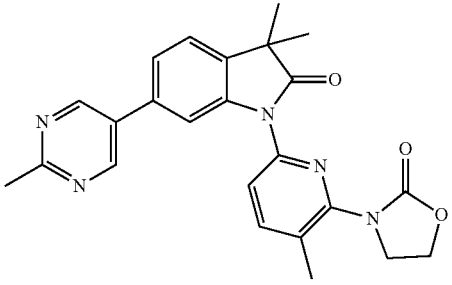 [SMILES: Cc1ncc(-c2ccc3c(c2)N(c2ccc(C)c(N4CCOC4=O)n2)C(=O)C3(C)C)cn1] | 0.0324 |
| 33 | 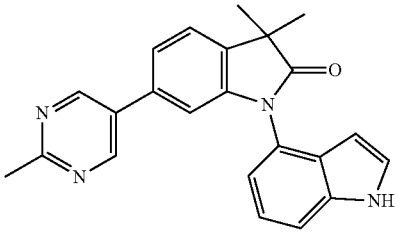 [SMILES: Cc1ncc(-c2ccc3c(c2)N(c2cccc4[nH]ccc24)C(=O)C3(C)C)cn1] | 0.7424 |

TABLE 1-continued

Effects of compounds of formula I on ENT1 inhibition

| Expl. | structure | ENT1, adenosine uptake, IC50 (uM) |
|---|---|---|
| 34 | 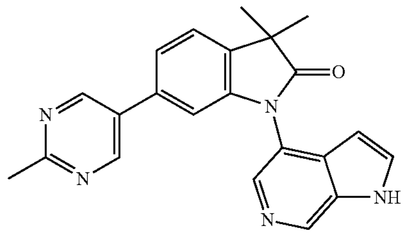 [SMILES: Cc1ncc(-c2ccc3c(c2)N(c2cncc4[nH]ccc24)C(=O)C3(C)C)cn1] | 0.8382 |
| 35 | 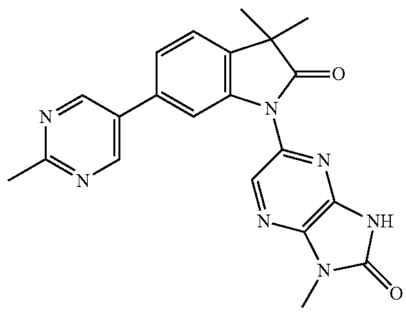 [SMILES: Cc1ncc(-c2ccc3c(c2)N(c2cnc4c(n2)[nH]c(=O)n4C)C(=O)C3(C)C)cn1] | 0.4959 |
| 36 | 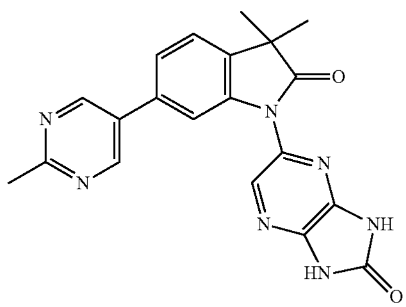 [SMILES: Cc1ncc(-c2ccc3c(c2)N(c2cnc4[nH]c(=O)[nH]c4n2)C(=O)C3(C)C)cn1] | 0.3746 |
| 37 | 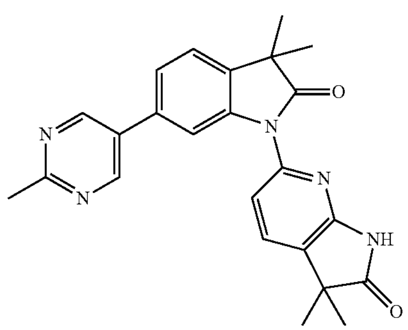 [SMILES: Cc1ncc(-c2ccc3c(c2)N(c2ccc4c(n2)NC(=O)C4(C)C)C(=O)C3(C)C)cn1] | 0.0067 |
| 38 | 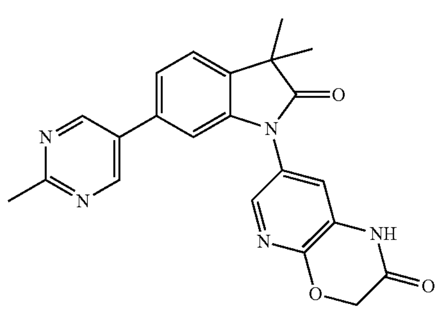 [SMILES: Cc1ncc(-c2ccc3c(c2)N(c2cnc4c(c2)NC(=O)CO4)C(=O)C3(C)C)cn1] | 0.0614 |

TABLE 1-continued

Effects of compounds of formula I on ENT1 inhibition

| Expl. | structure | ENT1, adenosine uptake, IC50 (uM) |
|---|---|---|
| 39 | 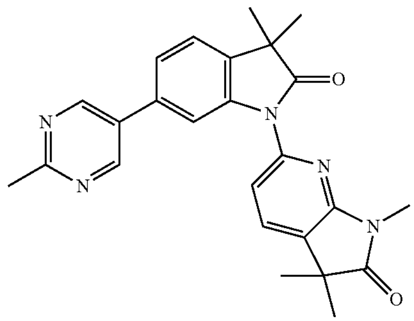 | 0.0269 |
| 40 | 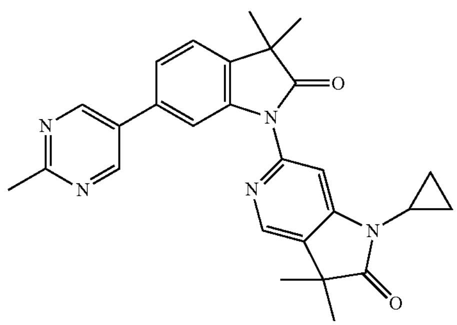 [SMILES: Cc1ncc(-c2ccc3c(c2)N(c2cc4c(cn2)C(C)(C)C(=O)N4C2CC2)C(=O)C3(C)C)cn1] | 0.4935 |
| 41 | 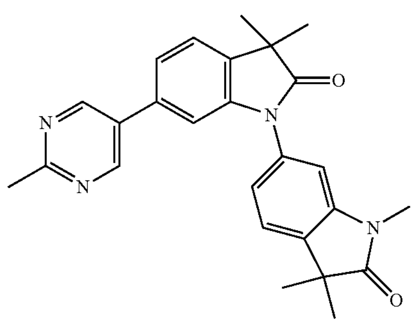 | 0.1136 |
| 42 | 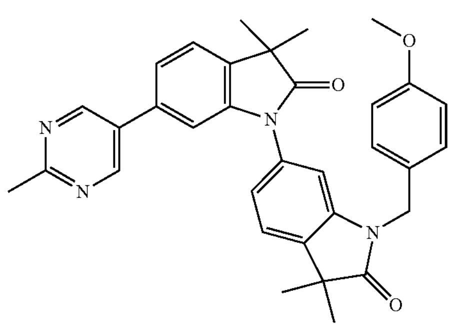 [SMILES: COc1ccc(CN2C(=O)C(C)(C)c3ccc(N4C(=O)C(C)(C)c5ccc(-c6cnc(C)nc6)cc54)cc32)cc1] | 0.1931 |

TABLE 1-continued
Effects of compounds of formula I on ENT1 inhibition
| Expl. structure | ENT1, adenosine uptake, IC50 (uM) |
|---|---|
| 43 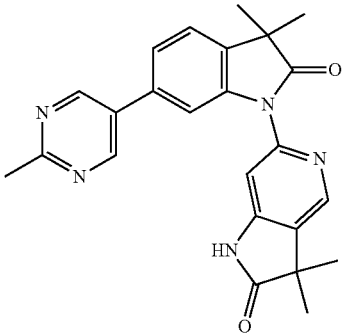 | 0.3853 |
| 44 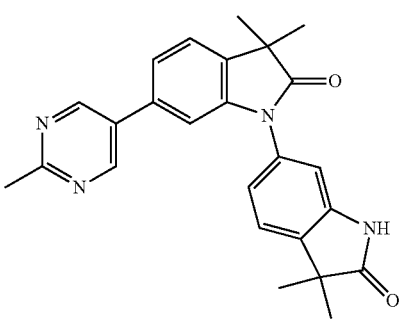 [SMILES: Cc1ncc(-c2ccc3c(c2)N(c2ccc4c(c2)NC(=O)C4(C)C)C(=O)C3(C)C)cn1] | 0.1279 |
| 45 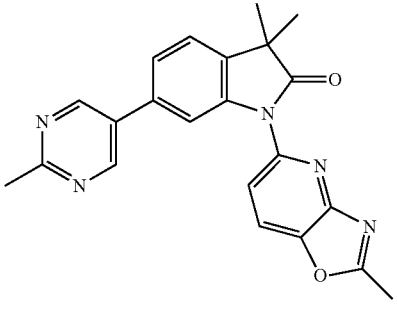 | 0.5927 |
| 46 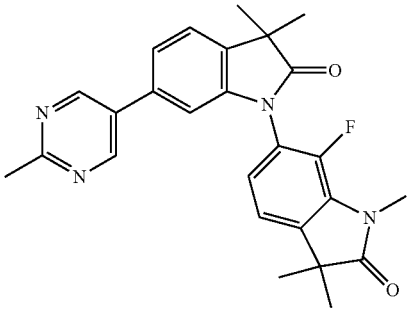 | 0.2436 |

TABLE 1-continued
Effects of compounds of formula I on ENT1 inhibition
| Expl. | structure | ENT1, adenosine uptake, IC50 (uM) |
|---|---|---|
| 47 | 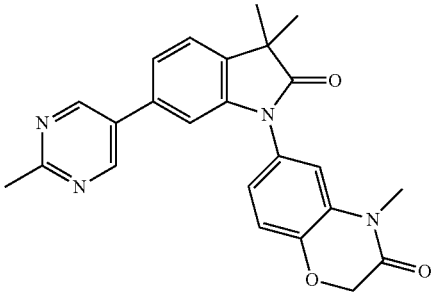 [SMILES: Cc1ncc(-c2ccc3c(c2)N(c2ccc4c(c2)N(C)C(=O)CO4)C(=O)C3(C)C)cn1] | 0.0142 |
| 48 | 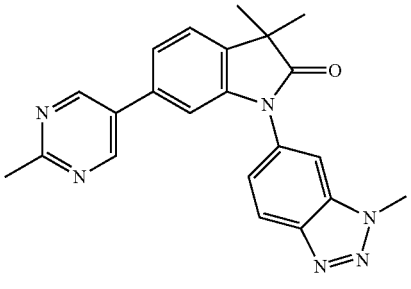 | 0.1845 |
| 49 | 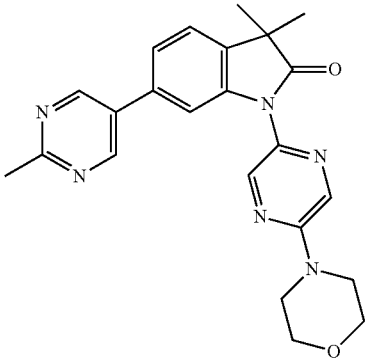 [SMILES: Cc1ncc(-c2ccc3c(c2)N(c2cnc(N4CCOCC4)cn2)C(=O)C3(C)C)cn1] | 0.4154 |
| 50 | 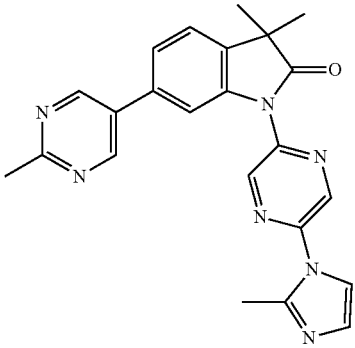 [SMILES: Cc1ncc(-c2ccc3c(c2)N(c2cnc(-n4ccnc4C)cn2)C(=O)C3(C)C)cn1] | 0.0311 |

TABLE 1-continued

Effects of compounds of formula I on ENT1 inhibition

| Expl. structure | ENT1, adenosine uptake, IC50 (uM) |
|---|---|
| 51 | 0.2274 |
| 52 | 0.2395 |
| 53 | 0.9927 |
| 54 | 0.0239 |

TABLE 1-continued

Effects of compounds of formula I on ENT1 inhibition

| Expl. | structure | ENT1, adenosine uptake, IC50 (uM) |
|---|---|---|
| 55 | 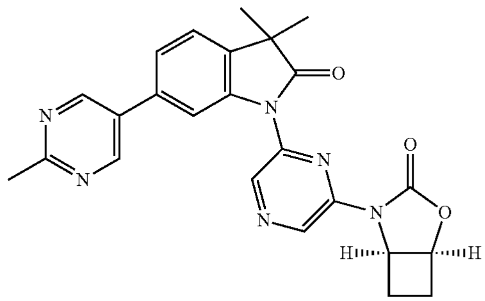 [SMILES: Cc1ncc(-c2ccc3c(c2)N(c2cncc(N4C(=O)O[C@H]5CC[C@H]54)n2)C(=O)C3(C)C)cn1] | 0.0248 |
| 56 | 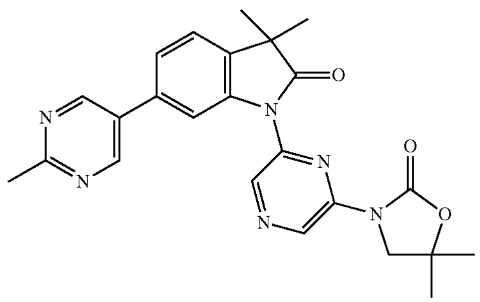 | 0.2020 |
| 57 | 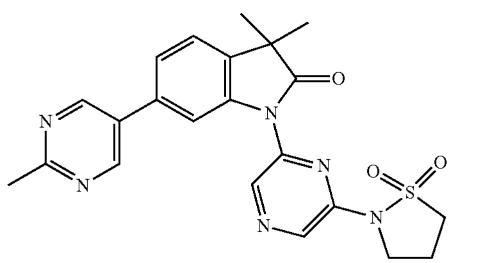 [SMILES: Cc1ncc(-c2ccc3c(c2)N(c2cncc(N4CCCS4(=O)=O)n2)C(=O)C3(C)C)cn1] | 0.0608 |
| 58 | 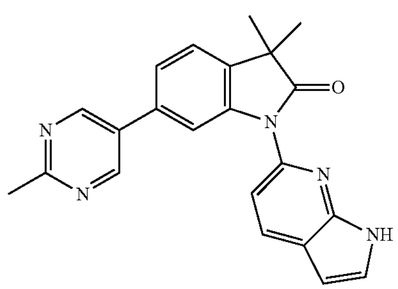 [SMILES: Cc1ncc(-c2ccc3c(c2)N(c2ccc4cc[nH]c4n2)C(=O)C3(C)C)cn1] | 0.2429 |
| 59 | 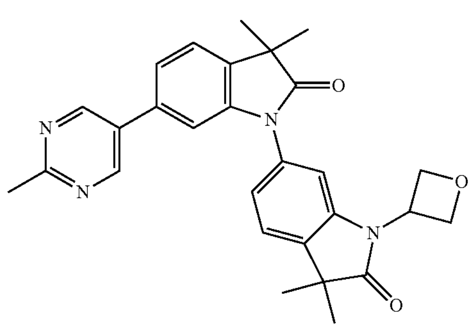 [SMILES: Cc1ncc(-c2ccc3c(c2)N(c2ccc4c(c2)N(C2COC2)C(=O)C4(C)C)C(=O)C3(C)C)cn1] | 0.2026 |

TABLE 1-continued

Effects of compounds of formula I on ENT1 inhibition

| Expl. | structure | ENT1, adenosine uptake, IC50 (uM) |
|---|---|---|
| 60 | 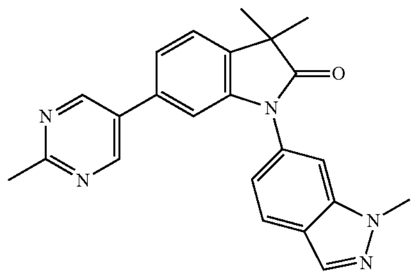 | 0.0377 |
| 61 | 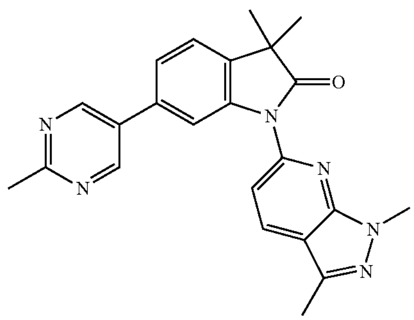 | 0.2020 |
| 62 | 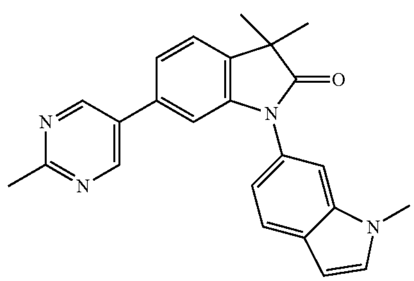 | 0.4276 |

TABLE 2

Effects of compounds on L-687,414-induced hyperlocomotion

| | L-687,414-induced hyperlocomotion | | |
|---|---|---|---|
| Expl. | Dose ip [mg/kg] | Inhibition, ip [%] | P value |
| 1 | 30 ip | 90 | 0.00008 |
| 3 | 30 ip | 87.8 | 0.00031 |
| 15 | 30 ip | 87.1 | 0.00008 |
| 18 | 30 ip | 88.8 | 0.00016 |
| 20 | 30 ip | 89.7 | 0.00016 |
| 39 | 30 ip | 99.5 | 0.00008 |
| 47 | 30 ip | 93.8 | 0.00008 |
| 50 | 30 ip | 96.3 | 0.00008 |
| 54 | 30 ip | 93.5 | 0.00016 |

As mentioned above, some compounds have been tested in SmartCube®, an analytical system developed by PsychoGenics Inc.

SmartCube® was used to compare the behavioral signature of a test compound to a database of behavioral signatures obtained from a large set of clinically approved reference drugs, grouped per indications. In this way, the neuropharmacological effects of a test compound can be predicted by similarity to major classes of compounds, such as antipsychotics, anxiolytics and antidepressants. This approach is ideally suited to screen collections of existing drugs or drug candidates with previously unknown neuropharmacology, which could expedite the development of new and unexpected treatments for psychiatric disorders.

Some compounds of the present invention were injected i.p. at different doses 15 minutes before the test. At least 8 mice were used in each treatment group. Digital videos of the subjects were processed with computer vision algorithms to extract over 2000 dependent measures including frequency and duration of many different behavioral states. The results of the classifications are presented as bar charts for each compound and dose (mg/kg), the Y-axis indicates the relative probability that the test compound will show efficacy in the specific CNS indication.

Compounds of the present invention show similar signatures to those of atypical antipsychotics. An independent analysis was performed on the unclassified data to determine the similarity of the example compounds to active doses of known atypical antipsychotics. For this analysis, we use discrimination rate as the measure of separability between the two drugs, i.e. one drug's "distinguishability" from another. A rate equal to 50% (or 0.5) corresponds to zero distinguishability. Empirical data has shown that a threshold rate for reliable separation lies above 70% i.e., two drugs showing a discrimination rate of 70% or lower are considered similar, whereas a discrimination rate higher than 70% indicates that two drugs are dissimilar. The table below shows the similarity analysis of selected compounds of the present invention to several atypical antipsychotics. In most cases, the example compounds show a similarity to risperidone, clozapine and olanzapine with a discrimination rate of 0.70.

TABLE 3

Similarity analysis of compounds of formula I showing effects in SmartCube ®

| Example | Clozapine (1.0 mg/kg) | Olanzapine (0.25 mg/kg) | Risperidone (0.06 mg/kg) |
|---|---|---|---|
| 1 (3 mg/kg) | 0.56 | 0.59 | 0.83 |
| 3 (5 mg/kg) | 0.62 | 0.66 | 0.68 |
| 15 (3 mg/kg) | 0.57 | 0.56 | 0.59 |
| 18 (3 mg/kg) | 0.61 | 0.62 | 0.73 |
| 20 (3 mg/kg) | 0.53 | 0.51 | 0.57 |
| 39 (3 mg/kg) | 0.59 | 0.58 | 0.62 |
| 50 (3 mg/kg) | 0.52 | 0.51 | 0.63 |
| 54 (3 mg/kg) | 0.54 | 0.51 | 0.57 |

Therefore, it can be assumed that the present compounds have similar efficacies as known atypical antipsychotics.

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers. The active compounds may also be used in form of their prodrugs.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult person weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

The invention claimed is:

1. A compound of formula

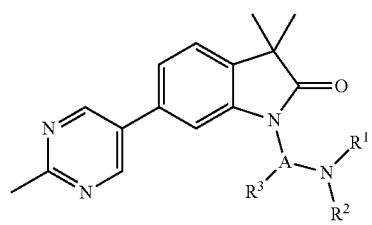

I wherein

A is phenyl or a six membered heteroaryl group, containing one or two N atoms, selected from

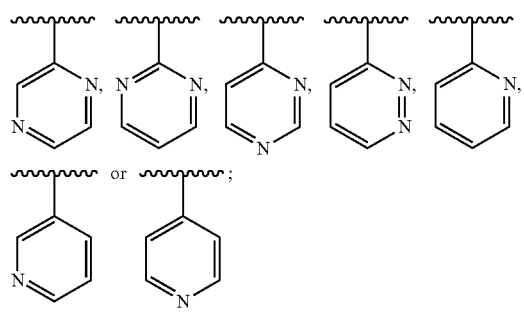

or the amine group —NR¹R² may form together with two neighboring carbon atoms from the group A an additional fused ring, selected from

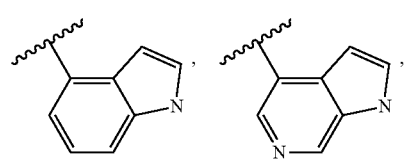

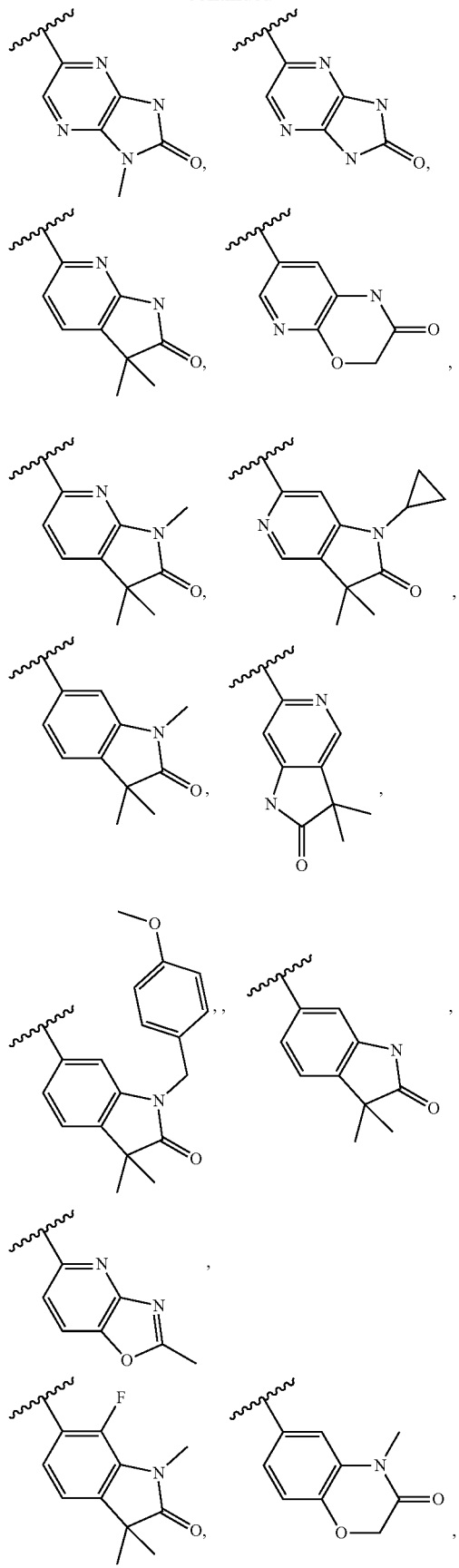

-continued

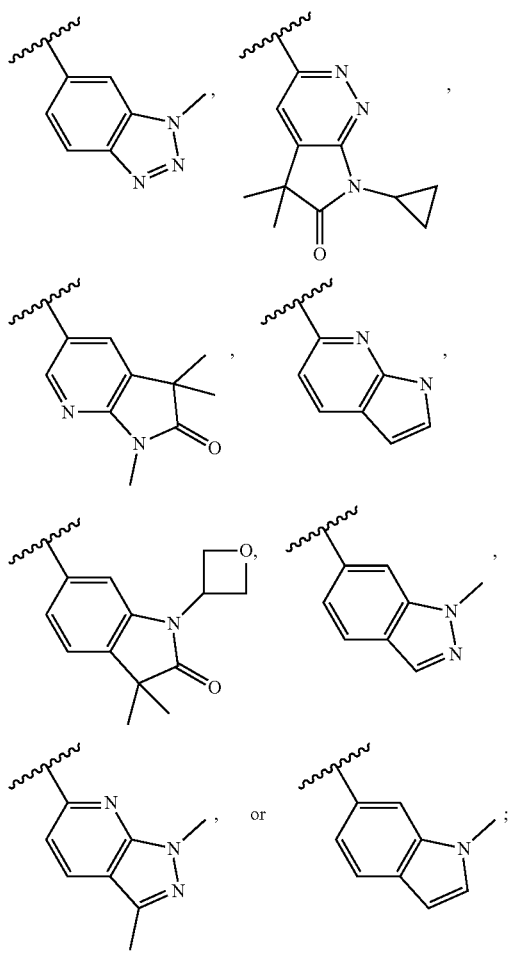

R$^1$ and R$^2$ are independently selected from hydrogen, C(O)-lower alkyl, cycloalkyl, —(CH$_2$)$_2$-lower alkoxy, lower alkyl or oxetanyl;

or R$^1$ and R$^2$ may form together with the N atom to which they are attach the group

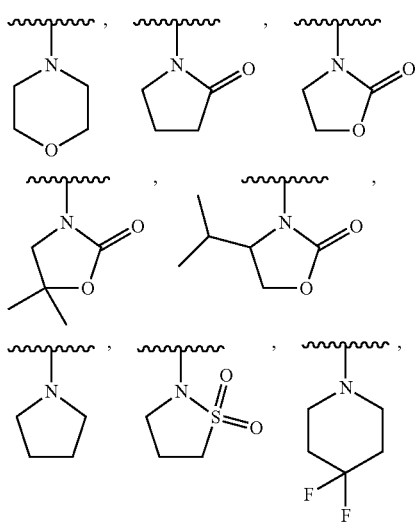

-continued

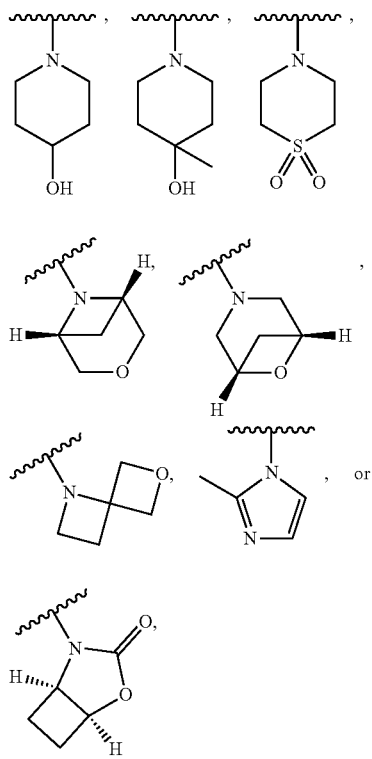

and

R$^3$ is hydrogen or lower alkyl;

or a pharmaceutically acceptable salt thereof.

2. The compound of formula IA according to claim 1,

IA

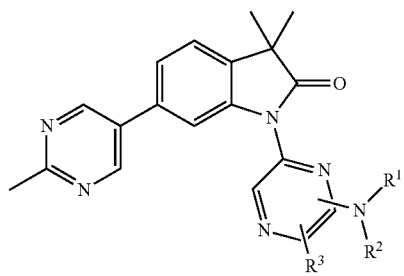

wherein

R$^1$ and R$^2$ are independently selected from hydrogen, C(O)-lower alkyl, cycloalkyl, —(CH$_2$)$_2$-lower alkoxy, lower alkyl or oxetanyl;

or R$^1$ and R$^2$ may form together with the N atom to which they are attach the group

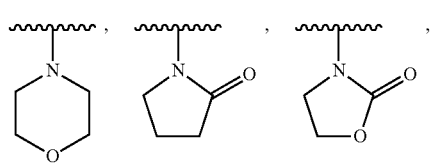

and

R³ is hydrogen or lower alkyl;

or a pharmaceutically acceptable salt thereof.

3. The A compound of formula IA according to claim 2, which compound is:

3,3-dimethyl-6-(2-methylpyrimidin-5-yl)-1-(6-morpholinopyrazin-2-yl)indolin-2-one;
1-(6-aminopyrazin-2-yl)-3,3-dimethyl-6-(2-methylpyrimidin-5-yl)indolin-2-one;
3,3-dimethyl-6-(2-methylpyrimidin-5-yl)-1-(6-(2-oxopyrrolidin-1-yl)pyrazin-2-yl)indolin-2-one;
3,3-dimethyl-6-(2-methylpyrimidin-5-yl)-1-(6-(pyrrolidin-1-yl)pyrazin-2-yl)indolin-2-one;
N-(6-(3,3-dimethyl-6-(2-methylpyrimidin-5-yl)-2-oxoindolin-1-yl)pyrazin-2-yl)acetamide;
1-(6-(4,4-difluoropiperidin-1-yl)pyrazin-2-yl)-3,3-dimethyl-6-(2-methylpyrimidin-5-yl)indolin-2-one;
1-(6-(cyclopropylamino)pyrazin-2-yl)-3,3-dimethyl-6-(2-methylpyrimidin-5-yl)indolin-2-one;
1-[6-(2-methoxyethylamino)pyrazin-2-yl]-3,3-dimethyl-6-(2-methylpyrimidin-5-yl)indol-2-one;
1-(6-(4-hydroxypiperidin-1-yl)pyrazin-2-yl)-3,3-dimethyl-6-(2-methylpyrimidin-5-yl)indolin-2-one;
1-(6-(1,1-dioxidothiomorpholino)pyrazin-2-yl)-3,3-dimethyl-6-(2-methylpyrimidin-5-yl)indolin-2-one;
1-(6-(4-hydroxy-4-methylpiperidin-1-yl)pyrazin-2-yl)-3,3-dimethyl-6-(2-methylpyrimidin-5-yl)indolin-2-one;
1-(6-((2-methoxyethyl)(methyl)amino)pyrazin-2-yl)-3,3-dimethyl-6-(2-methylpyrimidin-5-yl)indolin-2-one;
1-(6-((1R,5S)-3-oxa-6-azabicyclo[3.1.1]heptan-6-yl)pyrazin-2-yl)-3,3-dimethyl-6-(2-methylpyrimidin-5-yl)indolin-2-one;
1-(6-(6-oxa-1-azaspiro[3.3]heptan-1-yl)pyrazin-2-yl)-3,3-dimethyl-6-(2-methylpyrimidin-5-yl)indolin-2-one;
3-(6-(3,3-dimethyl-6-(2-methylpyrimidin-5-yl)-2-oxoindolin-1-yl)pyrazin-2-yl)oxazolidin-2-one
1-(6-((1R,5S)-6-oxa-3-azabicyclo[3.1.1]heptan-3-yl)pyrazin-2-yl)-3,3-dimethyl-6-(2-methylpyrimidin-5-yl)indolin-2-one;
3,3-dimethyl-6-(2-methylpyrimidin-5-yl)-1-(6-(oxetan-3-ylamino)pyrazin-2-yl)indolin-2-one;
3,3-dimethyl-1-(5-methyl-6-morpholinopyrazin-2-yl)-6-(2-methylpyrimidin-5-yl)indolin-2-one;
1-(6-((2-methoxyethyl)amino)-5-methylpyrazin-2-yl)-3,3-dimethyl-6-(2-methylpyrimidin-5-yl)indolin-2-one;
3-(6-(3,3-dimethyl-6-(2-methylpyrimidin-5-yl)-2-oxoindolin-1-yl)-3-methylpyrazin-2-yl)oxazolidin-2-one;
(R)-3-(6-(3,3-dimethyl-6-(2-methylpyrimidin-5-yl)-2-oxoindolin-1-yl)pyrazin-2-yl)-4-isopropyloxazolidin-2-one;
(S)-3-(6-(3,3-dimethyl-6-(2-methylpyrimidin-5-yl)-2-oxoindolin-1-yl)pyrazin-2-yl)-4-isopropyloxazolidin-2-one;
3,3-dimethyl-6-(2-methylpyrimidin-5-yl)-1-(5-morpholinopyrazin-2-yl)indolin-2-one;
3,3-dimethyl-1-(5-(2-methyl-1H-imidazol-1-yl)pyrazin-2-yl)-6-(2-methylpyrimidin-5-yl)indolin-2-one;
1-(5-((1R,5S)-3-oxa-6-azabicyclo[3.1.1]heptan-6-yl)pyrazin-2-yl)-3,3-dimethyl-6-(2-methylpyrimidin-5-yl)indolin-2-one;
1-(5-((2-hydroxyethyl)amino)pyrazin-2-yl)-3,3-dimethyl-6-(2-methylpyrimidin-5-yl)indolin-2-one;
rac-(1S,5R)-4-(6-(3,3-dimethyl-6-(2-methylpyrimidin-5-yl)-2-oxoindolin-1-yl)pyrazin-2-yl)-2-oxa-4-azabicyclo[3.2.0]heptan-3-one;
3-(6-(3,3-dimethyl-6-(2-methylpyrimidin-5-yl)-2-oxoindolin-1-yl)pyrazin-2-yl)-5,5-dimethyloxazolidin-2-one; or
1-(6-(1,1-dioxidoisothiazolidin-2-yl)pyrazin-2-yl)-3,3-dimethyl-6-(2-methylpyrimidin-5-yl)indolin-2-one, or a pharmaceutically acceptable salt thereof.

4. The compound of formula IB according to claim 1,

IB wherein

R¹ and R² are independently selected from hydrogen, C(O)-lower alkyl, cycloalkyl, —(CH₂)₂-lower alkoxy, lower alkyl or oxetanyl;

or R¹ and R² may form together with the N atom to which they are attach the group

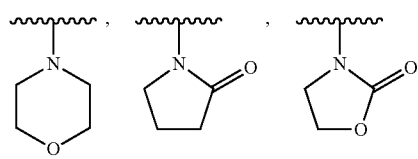

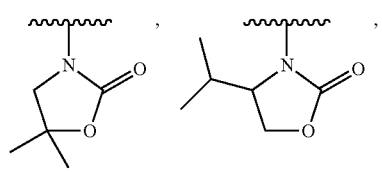

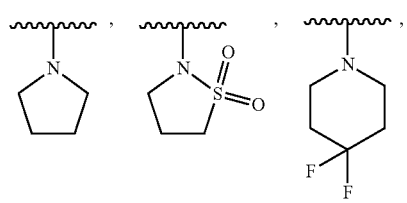

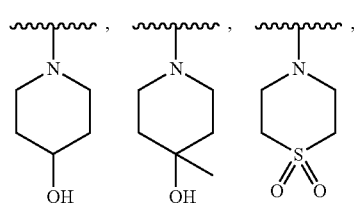

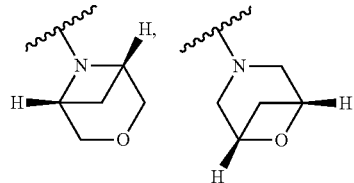

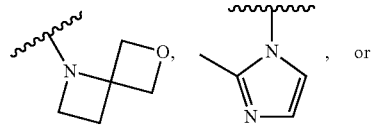

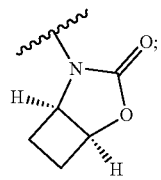

and
R³ is hydrogen or lower alkyl;
or a pharmaceutically acceptable salt thereof.

5. The compound of formula IB according to claim 4, which compound is:
3,3-dimethyl-6-(2-methylpyrimidin-5-yl)-1-(4-morpholinopyrimidin-2-yl)indolin-2-one, or a pharmaceutically acceptable salt thereof.

6. The compound of formula IC according to claim 1,

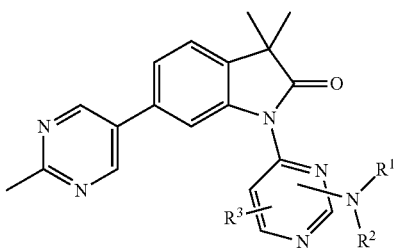

IC wherein
R¹ and R² are independently selected from hydrogen, C(O)-lower alkyl, cycloalkyl, —(CH₂)₂-lower alkoxy, lower alkyl or oxetanyl;
or R¹ and R² may form together with the N atom to which they are attach the group

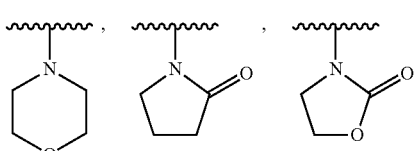

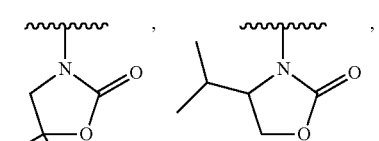

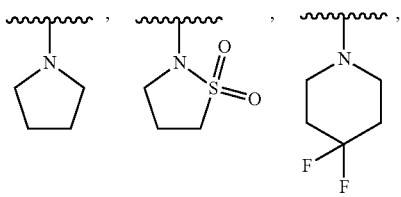

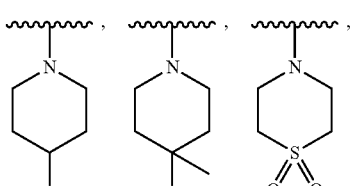

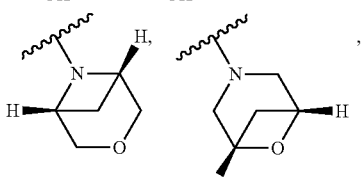

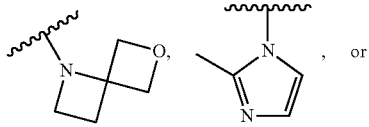

-continued

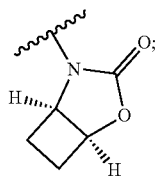

and
R³ is hydrogen or lower alkyl;
or a pharmaceutically acceptable salt thereof.
7. The compound of formula IC according to claim 6, which compound is:
3,3-dimethyl-6-(2-methylpyrimidin-5-yl)-1-(2-morpholinopyrimidin-4-yl)indolin-2-one, or a pharmaceutically acceptable salt thereof.
8. The compound of formula ID according to claim 1

ID

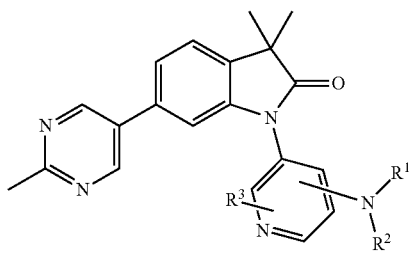

wherein
R¹ and R² are independently selected from hydrogen, C(O)-lower alkyl, cycloalkyl, —(CH₂)₂-lower alkoxy, lower alkyl or oxetanyl;
or R¹ and R² may form together with the N atom to which they are attach the group

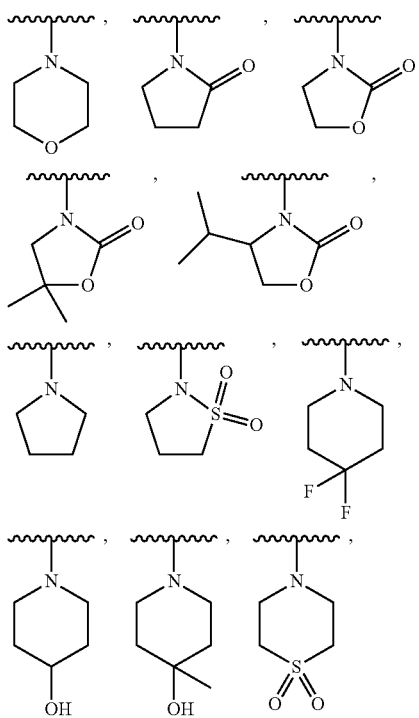

-continued

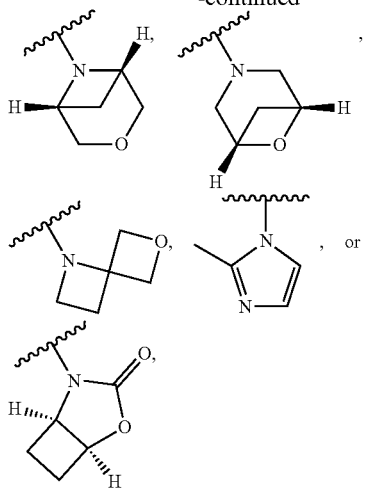

and
R³ is hydrogen or lower alkyl;
or a pharmaceutically acceptable salt thereof.
9. The compound of formula ID according to claim 8, which compounds are:
1-(5-aminopyridin-3-yl)-3,3-dimethyl-6-(2-methylpyrimidin-5-yl)indolin-2-one; or
3,3-dimethyl-6-(2-methylpyrimidin-5-yl)-1-(5-morpholinopyridin-3-yl)indolin-2-one, or a pharmaceutically acceptable salt thereof.
10. The compound of formula IE according to claim 1,

IE

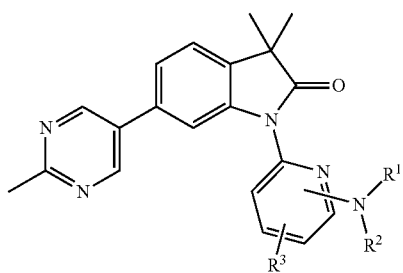

wherein
R¹ and R² are independently selected from hydrogen, C(O)-lower alkyl, cycloalkyl, —(CH₂)₂-lower alkoxy, lower alkyl or oxetanyl;
or R¹ and R² may form together with the N atom to which they are attach the group

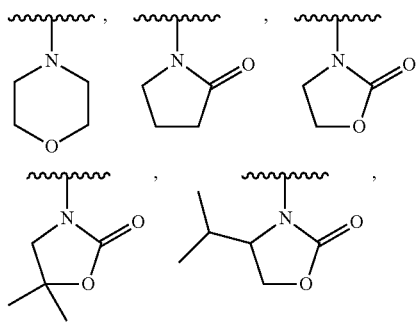

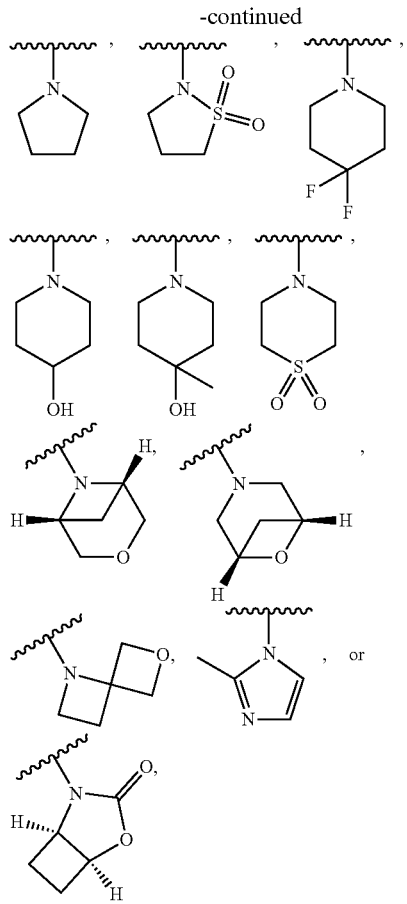

and
R³ is hydrogen or lower alkyl;
or a pharmaceutically acceptable salt thereof.

11. The compound of formula IE according to claim 10, which compounds are:
3,3-dimethyl-6-(2-methylpyrimidin-5-yl)-1-(6-morpholinopyridin-2-yl)indolin-2-one;
3-(6-(3,3-dimethyl-6-(2-methylpyrimidin-5-yl)-2-oxoindolin-1-yl)pyridin-2-yl)oxazolidin-2-one;
1-(6-amino-5-methylpyridin-2-yl)-3,3-dimethyl-6-(2-methylpyrimidin-5-yl)indolin-2-one;
N-(6-(3,3-dimethyl-6-(2-methylpyrimidin-5-yl)-2-oxoindolin-1-yl)-3-methylpyridin-2-yl)acetamide;
3,3-dimethyl-1-(5-methyl-6-morpholinopyridin-2-yl)-6-(2-methylpyrimidin-5-yl)indolin-2-one; or
3-(6-(3,3-dimethyl-6-(2-methylpyrimidin-5-yl)-2-oxoindolin-1-yl)-3-methylpyridin-2-yl)oxazolidin-2-one, or a pharmaceutically acceptable salt thereof.

12. The compound of formula IF according to claim 1,

IF

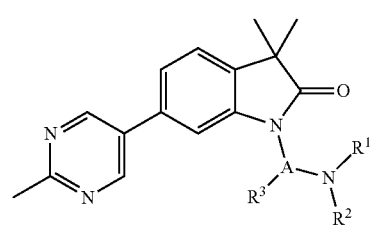

wherein
the amine group —NR¹R², wherein R² hydrogen, may form together with two neighboring carbon atoms from the group A as described in formula I an additional fused ring, selected from

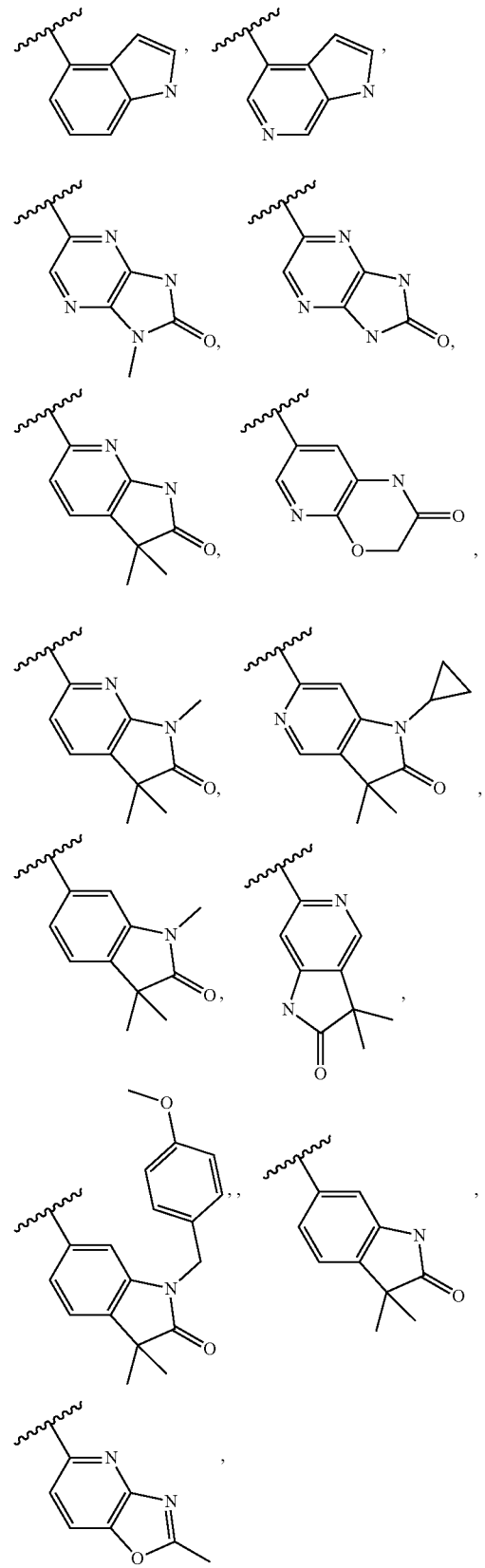

-continued

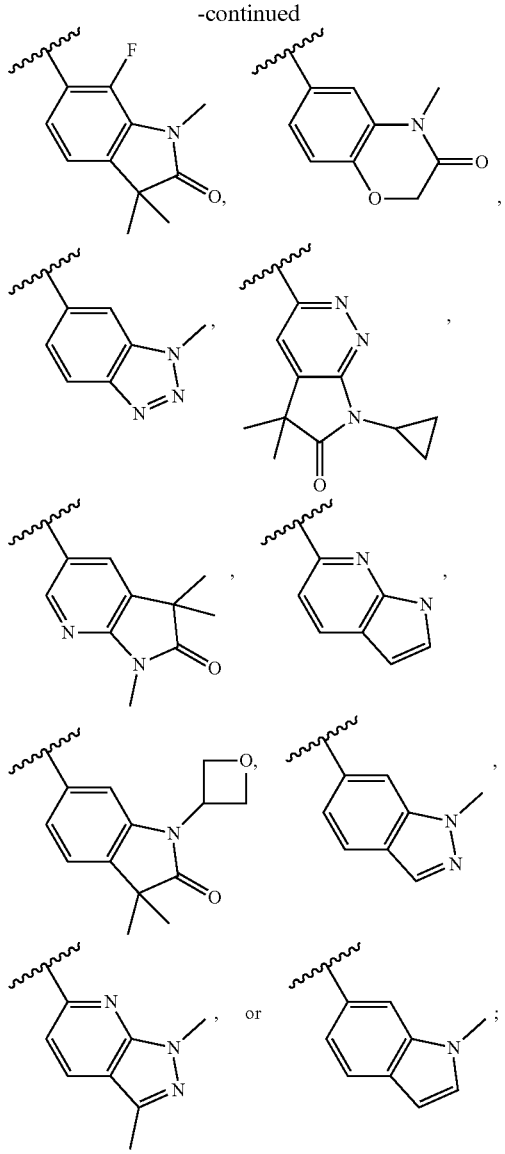

and
R³ is hydrogen;
or a pharmaceutically acceptable salt thereof.

13. The compound of formula IF according to claim 12, which compounds are:
  1-(1H-indol-4-yl)-3,3-dimethyl-6-(2-methylpyrimidin-5-yl)indolin-2-one;
  3,3-dimethyl-6-(2-methylpyrimidin-5-yl)-1-(1H-pyrrolo[2,3-c]pyridin-4-yl)indolin-2-one;
  5-(3,3-dimethyl-6-(2-methylpyrimidin-5-yl)-2-oxoindolin-1-yl)-1-methyl-1H-imidazo[4,5-b]pyrazin-2(3H)-one;
  5-(3,3-dimethyl-6-(2-methylpyrimidin-5-yl)-2-oxoindolin-1-yl)-1H-imidazo[4,5-b]pyrazin-2(3H)-one;
  6-(3,3-dimethyl-6-(2-methylpyrimidin-5-yl)-2-oxoindolin-1-yl)-3,3-dimethyl-1H-pyrrolo[2,3-b]pyridin-2(3H)-one;
  7-(3,3-dimethyl-6-(2-methylpyrimidin-5-yl)-2-oxoindolin-1-yl)-1H-pyrido[2,3-b][1,4]oxazin-2(3H)-one;
  6-(3,3-dimethyl-6-(2-methylpyrimidin-5-yl)-2-oxoindolin-1-yl)-1,3,3-trimethyl-1H-pyrrolo[2,3-b]pyridin-2(3H)-one;
  1-cyclopropyl-6-(3,3-dimethyl-6-(2-methylpyrimidin-5-yl)-2-oxoindolin-1-yl)-3,3-dimethyl-1H-pyrrolo[3,2-c]pyridin-2(3H)-one;
  1',3,3,3',3'-pentamethyl-6-(2-methylpyrimidin-5-yl)-[1,6'-biindoline]-2,2'-dione;
  1'-(4-methoxybenzyl)-3,3,3',3'-tetramethyl-6-(2-methylpyrimidin-5-yl)-[1,6'-biindoline]-2,2'-dione;
  6-(3,3-dimethyl-6-(2-methylpyrimidin-5-yl)-2-oxoindolin-1-yl)-3,3-dimethyl-1H-pyrrolo[3,2-c]pyridin-2(3H)-one;
  3,3,3',3'-tetramethyl-6-(2-methylpyrimidin-5-yl)-[1,6'-biindoline]-2,2'-dione;
  3,3-dimethyl-1-(2-methyloxazolo[4,5-b]pyridin-5-yl)-6-(2-methylpyrimidin-5-yl)indolin-2-one;
  7'-fluoro-1',3,3,3',3'-pentamethyl-6-(2-methylpyrimidin-5-yl)-[1,6'-biindoline]-2,2'-dione;
  6-(3,3-dimethyl-6-(2-methylpyrimidin-5-yl)-2-oxoindolin-1-yl)-4-methyl-2H-benzo[b][1,4]oxazin-3(4H)-one;
  3,3-dimethyl-1-(1-methyl-1H-benzo[d][1,2,3]triazol-6-yl)-6-(2-methylpyrimidin-5-yl)indolin-2-one;
  7-cyclopropyl-3-(3,3-dimethyl-6-(2-methylpyrimidin-5-yl)-2-oxoindolin-1-yl)-5,5-dimethyl-5H-pyrrolo[2,3-c]pyridazin-6(7H)-one;
  5-(3,3-dimethyl-6-(2-methylpyrimidin-5-yl)-2-oxoindolin-1-yl)-1,3,3-trimethyl-1H-pyrrolo[2,3-b]pyridin-2(3H)-one;
  3,3-dimethyl-6-(2-methylpyrimidin-5-yl)-1-(1H-pyrrolo[2,3-b]pyridin-6-yl)indolin-2-one;
  3,3,3',3'-tetramethyl-6-(2-methylpyrimidin-5-yl)-1'-(oxetan-3-yl)-[1,6'-biindoline]-2,2'-dione;
  3,3-dimethyl-1-(1-methyl-1H-indazol-6-yl)-6-(2-methylpyrimidin-5-yl)indolin-2-one;
  1-(1,3-dimethyl-1H-pyrazolo[3,4-b]pyridin-6-yl)-3,3-dimethyl-6-(2-methylpyrimidin-5-yl)indolin-2-one; or
  3,3-dimethyl-1-(1-methyl-1H-indol-6-yl)-6-(2-methylpyrimidin-5-yl)indolin-2-one, or a pharmaceutically acceptable salt thereof.

14. A combination of a compound of formula I according to claim 1 together with a known marketed antipsychotic, antidepressant, anxiolytic or mood stabilizer.

15. The combination according to claim 14, wherein the marketed antipsychotic drug is olanzapine, clozapine, risperidone, aripiprazole or ziprasidone.

16. The combination according to claim 14, wherein the marketed anti-depressive drug is citalopram, escitalopram, paroxetine, fluoxetine, sertraline duloxetine, milnacipran, venlafaxine, or mirtazapine.

17. The combination according to claim 14, wherein the marketed anxiolytic drug is alprazolam, chlordiazepoxide, clonazepam, diazepam, Estazolam, eszopiclone, zaleplon, zolpidem, pregabalin or gabapentin.

18. The combination according to claim 14, wherein the marketed mood stabilizer is carbamazepine, lamotrigine, lithium, and valproic acid.

19. A process for the preparation of a compound of formula I of claim 1, the process comprising:
  a) reacting a compound of formula

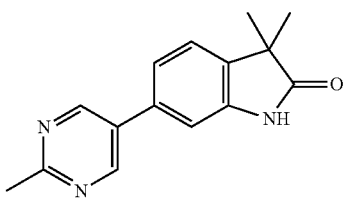

1 with a compound of formula

Y-A(R³)—NR¹R²    2 to make a compound of formula

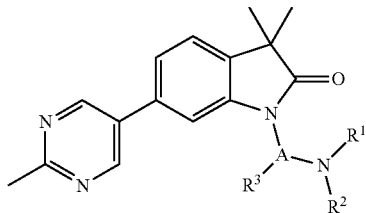

I wherein Y is Cl, Br or I and the other groups have the meaning as described in claim 1 and, if desired, converting the compound obtained into a pharmaceutically acceptable salt; or b) reacting a compound of formula 4

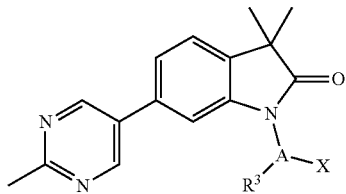

4 with $HNR^1R^2$ to make a compound of formula I

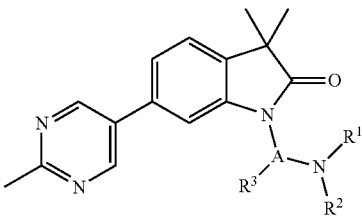

I wherein X is Cl, Br or I and the other groups have the meaning as described in claim 1 and, if desired, converting the compound obtained into a pharmaceutically acceptable salt.

20. A pharmaceutical composition comprising a compound in accordance with claim 1, or a pharmaceutically acceptable salt thereof, and a carrier.

\* \* \* \* \*